US012721666B2

(12) United States Patent
Tschida

(10) Patent No.: US 12,721,666 B2
(45) Date of Patent: Sep. 1, 2026

(54) SEGMENTAL VASCULAR ABLATION

(71) Applicant: Crossfire Medical Inc, Dover, DE (US)

(72) Inventor: Adam Tschida, Brooklyn Park, MN (US)

(73) Assignee: VERGE MEDICAL, INC., Campbell, CA (US)

(*) Notice: Subject to any disclaimer, the term of this patent is extended or adjusted under 35 U.S.C. 154(b) by 0 days.

(21) Appl. No.: 18/427,612

(22) Filed: Jan. 30, 2024

(65) Prior Publication Data

US 2024/0164824 A1 May 23, 2024

Related U.S. Application Data

(62) Division of application No. 18/364,357, filed on Aug. 2, 2023, now Pat. No. 11,980,409.

(Continued)

(51) Int. Cl.

*A61B 18/06* (2006.01)
*A61B 18/00* (2006.01)
*A61M 25/00* (2006.01)

(52) U.S. Cl.

CPC ......... *A61B 18/06* (2013.01); *A61M 25/0084* (2013.01); *A61B 2018/00577* (2013.01); *A61B 2018/00702* (2013.01)

(58) Field of Classification Search

CPC .......... A61B 2018/00577; A61B 5/287; A61B 2218/002; A61B 34/20; A61B 5/6852; A61B 2018/0212; A61B 2017/00243; A61B 2018/1467; A61B 2018/00702; A61B 18/14; A61B 2018/1435; A61N 7/022; A61N 1/05; A61M 25/0147;

(Continued)

(56) References Cited

U.S. PATENT DOCUMENTS 4,664,113 A 5/1987 Frisbie
5,497,847 A 3/1996 Ota (Continued)

FOREIGN PATENT DOCUMENTS

AU 2019257451 A1 11/2019
CN 101987033 B 10/2012

(Continued)

*Primary Examiner* — Scott J Medway
(74) *Attorney, Agent, or Firm* — Gallium Law; Jacob Panangat; Justin Schwechter

(57) ABSTRACT

The disclosure includes a controller and a sheath having an open proximal sheath end coupled to the controller, an open distal sheath end configured for insertion into a vascular system of a patient, and a working lumen extending through the sheath. The system may include a wire extending from the controller through the working lumen, the wire having a distal wire end configured to mechanically treat a vessel wall of a treatment segment, a length of the distal wire end defining a length of the treatment segment. The working lumen may be configured to slidably receive the wire and allow for a passage of a fluid about the wire therethrough to chemically treat the treatment segment. When the system receives a first input the distal wire end may mechanically treat the vessel wall. When the system receives a second input and/or a third input, the system may deliver the fluid.

19 Claims, 73 Drawing Sheets

Related U.S. Application Data

(60) Provisional application No. 63/476,156, filed on Dec. 19, 2022, provisional application No. 63/396,586, filed on Aug. 9, 2022, provisional application No. 63/396,176, filed on Aug. 8, 2022.

(58) Field of Classification Search
CPC .............. A61M 25/09; A61M 25/0082; A61M 25/0105; A61M 25/0158
See application file for complete search history.

(56) References Cited

U.S. PATENT DOCUMENTS

| | | | | |
|---|---|---|---|---|
| 5,792,155 | A | 8/1998 | Cleef | |
| 5,816,105 | A | 10/1998 | Adelstein | |
| 6,293,927 | B1 | 9/2001 | McGuckin, Jr. | |
| 6,486,872 | B2 | 11/2002 | Rosenberg | |
| 6,538,634 | B1 | 3/2003 | Chui | |
| 6,722,224 | B2 | 4/2004 | Nordstrom | |
| 6,926,725 | B2 | 8/2005 | Cooke | |
| 7,037,316 | B2 | 5/2006 | McGuckin, Jr. | |
| 7,249,951 | B2 | 7/2007 | Bevirt | |
| 7,507,246 | B2 | 3/2009 | McGuckin | |
| 7,763,010 | B2 | 7/2010 | Evans | |
| 7,819,887 | B2 | 10/2010 | McGuckin, Jr. | |
| 7,821,496 | B2 | 10/2010 | Rosenberg | |
| 7,862,575 | B2 | 1/2011 | Tal | |
| 7,967,834 | B2 | 6/2011 | Tal | |
| 8,062,317 | B2 | 11/2011 | Mcguckin, Jr. | |
| 8,414,543 | B2 | 4/2013 | Mcguckin, Jr. | |
| 8,430,934 | B2 | 4/2013 | Das | |
| 8,465,508 | B2 | 6/2013 | Tal | |
| 8,465,511 | B2 | 6/2013 | Mcguckin, Jr. | |
| 8,663,259 | B2 | 3/2014 | Levine | |
| 8,746,103 | B2 | 6/2014 | Apkarian | |
| 8,764,779 | B2 | 7/2014 | Levine | |
| 9,023,070 | B2 | 5/2015 | Levine | |
| 9,133,835 | B2 | 9/2015 | Wong | |
| 9,282,992 | B2 | 3/2016 | Levine | |
| 9,474,543 | B2 | 10/2016 | Mcguckin, Jr. | |
| 9,480,467 | B2 | 11/2016 | Marano | |
| 9,700,346 | B2 | 7/2017 | Levine | |
| 9,795,406 | B2 | 10/2017 | Levine | |
| 9,889,874 | B1 | 2/2018 | Clause | |
| 9,924,957 | B2 | 3/2018 | Mcguckin, Jr. | |
| 10,064,645 | B2 | 9/2018 | Levine | |
| 10,086,174 | B2 * | 10/2018 | Crall ..................... | A61M 25/10 |
| 10,117,671 | B2 | 11/2018 | Mcguckin, Jr. | |
| 10,195,317 | B2 | 2/2019 | Mallough | |
| 10,363,397 | B2 | 7/2019 | Kanemasa | |
| 10,463,388 | B2 | 11/2019 | Tal | |
| 10,517,630 | B2 | 12/2019 | Levine | |
| 10,799,247 | B2 | 10/2020 | Brandeis | |
| 10,840,652 | B2 | 11/2020 | Wagner | |
| 11,020,194 | B2 | 6/2021 | Yang | |
| 11,298,510 | B2 | 4/2022 | Rochon | |
| 11,389,792 | B2 | 7/2022 | Hill | |
| 11,547,437 | B2 * | 1/2023 | Zarembinski ..... | A61M 25/0084 |
| 2008/0154202 | A1 | 6/2008 | Nemoto | |
| 2010/0082012 | A1 * | 4/2010 | Hattangadi ........ | A61M 25/1011 604/509 |
| 2012/0130415 | A1 | 5/2012 | Tal et al. | |
| 2015/0005792 | A1 | 1/2015 | Ahn | |
| 2015/0272654 | A1 * | 10/2015 | Esch .................. | A61B 18/1492 606/34 |
| 2016/0242790 | A1 | 8/2016 | Brandeis | |
| 2019/0350757 | A1 | 11/2019 | Charles | |
| 2020/0113575 | A1 | 4/2020 | Wisnosky et al. | |
| 2020/0138475 | A1 | 5/2020 | Tal | |
| 2020/0178980 | A1 | 6/2020 | Hill et al. | |
| 2021/0290926 | A1 | 9/2021 | Scherich | |

FOREIGN PATENT DOCUMENTS

| | | | |
|---|---|---|---|
| CN | 105050648 | B | 8/2018 |
| CN | 212214365 | U | 12/2020 |
| CN | 212547025 | U | 2/2021 |
| CN | 213374644 | U | 6/2021 |
| CN | 110049739 | B | 3/2022 |
| DE | 202004016877 | U1 | 2/2005 |
| DE | 102004016895 | A1 | 10/2005 |
| DE | 102006039471 | B3 | 3/2008 |
| EP | 1953618 | B1 | 4/2018 |
| EP | 3178518 | B1 | 11/2018 |
| EP | 3911397 | A1 | 11/2021 |
| EP | 3474939 | B1 | 12/2021 |
| JP | 2003325661 | A | 11/2003 |
| JP | 4551423 | B2 | 9/2010 |
| JP | 5286612 | B2 | 9/2013 |
| JP | 2013017834 | A | 2/2014 |
| JP | 2015503951 | A | 2/2015 |
| JP | 6221300 | B2 | 11/2017 |
| JP | 2018034006 | A | 3/2018 |
| JP | 6934531 | B2 | 9/2021 |
| KR | 101539142 | B1 | 7/2015 |
| TW | 1629074 | B | 7/2018 |
| WO | 2007068050 | A1 | 6/2007 |
| WO | 2022198039 | A1 | 9/2022 |

* cited by examiner

SEGMENTAL VASCULAR ABLATION

CROSS-REFERENCE TO RELATED APPLICATIONS

The entire contents of the following application are incorporated by reference herein: U.S. Provisional Patent Application No. 63/396,176; filed Aug. 8, 2022; and entitled VASCULAR ABLATION.

The entire contents of the following application are incorporated by reference herein: U.S. Provisional Patent Application No. 63/396,586; filed Aug. 9, 2022; and entitled VASCULAR ABLATION.

The entire contents of the following application are incorporated by reference herein: U.S. Provisional Patent Application No. 63/476,156; filed Dec. 19, 2022; and entitled CATHETER WIRE CONTROLLER.

INTRODUCTION

Technical Field

The present disclosure relates to systems and methods for the treatment of varicose veins.

BACKGROUND

Mechanochemical ablation (MOCA) is a medical procedure used to treat varicose veins, which are enlarged and twisted veins that typically occur in the legs. This minimally invasive procedure aims to close off the affected veins by using mechanical and/or chemical ablation techniques.

During the procedure, a specialized catheter is inserted into the varicose vein through a small incision. The catheter has a rotating tip that mechanically agitates (or abrades, or ablates) the vein's inner lining, causing endothelial damage. Simultaneously, a drug, such as sclerosant, which acts as a chemical solution that irritates and closes the vein, is delivered through the catheter. This combination of mechanical agitation (or abrasion, or ablation) and chemical irritation induces the closure of the varicose vein, causing it to shrink and eventually be absorbed by the body.

Mechanochemical ablation is considered a safe and effective alternative to traditional surgical treatments for varicose veins, such as vein stripping or ligation, as well as currently available endovascular alternatives, such as radiofrequency ablation, laser ablation, or glue closure. It is typically performed as an outpatient procedure, and patients can often resume normal activities shortly after the treatment.

SUMMARY

Included in the present disclosure is an ablation system (e.g., see the ablation system 10 as shown in FIG. 1), including a controller (e.g., see the controller 20 as shown in FIG. 1). In some examples, the system includes a sheath (e.g., see the sheath 40 as shown in FIG. 2) including an open proximal sheath end, an open distal sheath end, and a working lumen extending from the open proximal sheath end to the open distal sheath end. According to some examples, the open proximal sheath end is coupled to the controller and the open distal sheath end is configured for insertion into a vascular system of a patient, the open distal sheath end located opposite the open proximal sheath end.

The ablation system may include a wire (e.g., see the wire 30 as shown in FIG. 2) extending from the controller through the open proximal sheath end through the working lumen to the open distal sheath end. In some examples, the wire has a proximal wire end (e.g., see the proximal wire end 1202 as shown in FIG. 12) and a distal wire end (e.g., see the distal wire end 1204 as shown in FIG. 12) opposite the proximal wire end, the distal wire end configured to mechanically treat a vessel wall of a treatment segment (e.g., see the treatment segment 55 as shown in FIG. 2), whereby a length of the distal wire end defines a length of the treatment segment.

According to some examples, the working lumen is configured to slidably receive the wire and allow for a passage of a fluid about the wire therethrough to chemically treat the treatment segment. When the system receives a first input the distal wire end may mechanically treat the vessel wall. In some examples, when the system receives a second input, the system delivers the fluid into the treatment segment. According to some examples, when the system receives a third input, the system delivers the fluid into a subsequent treatment segment.

Also included in the present disclosure is a method, including inserting a catheter (e.g., see the catheter 15 as shown in FIG. 1) into a vascular system of a patient. In some examples, the method includes moving the catheter to a first treatment segment (e.g., see the treatment segment 55 as shown in FIG. 2). According to some examples, the method includes actuating a motor (e.g., see the motor 610 as shown in FIG. 6A) and rotating at least a portion of the catheter in response to actuating the motor.

The method may include abrading the first treatment segment for a predetermined amount of time in response to rotating at least the portion of the catheter. In some examples, the method includes moving the catheter to a second treatment segment. According to some examples, the method includes abrading the second treatment segment for the predetermined amount of time in response to rotating at least the portion of the catheter.

The foregoing, and other features and advantages of the invention, will be apparent from the following, more particular description of the preferred embodiments of the invention, the accompanying drawings, and the claims.

BRIEF DESCRIPTION OF THE DRAWINGS

These and other features, aspects, and advantages are described below with reference to the drawings, which are intended to illustrate, but not to limit, the invention. In the drawings, like characters denote corresponding features consistently throughout similar embodiments.

COMPONENT INDEX

Figure 1:
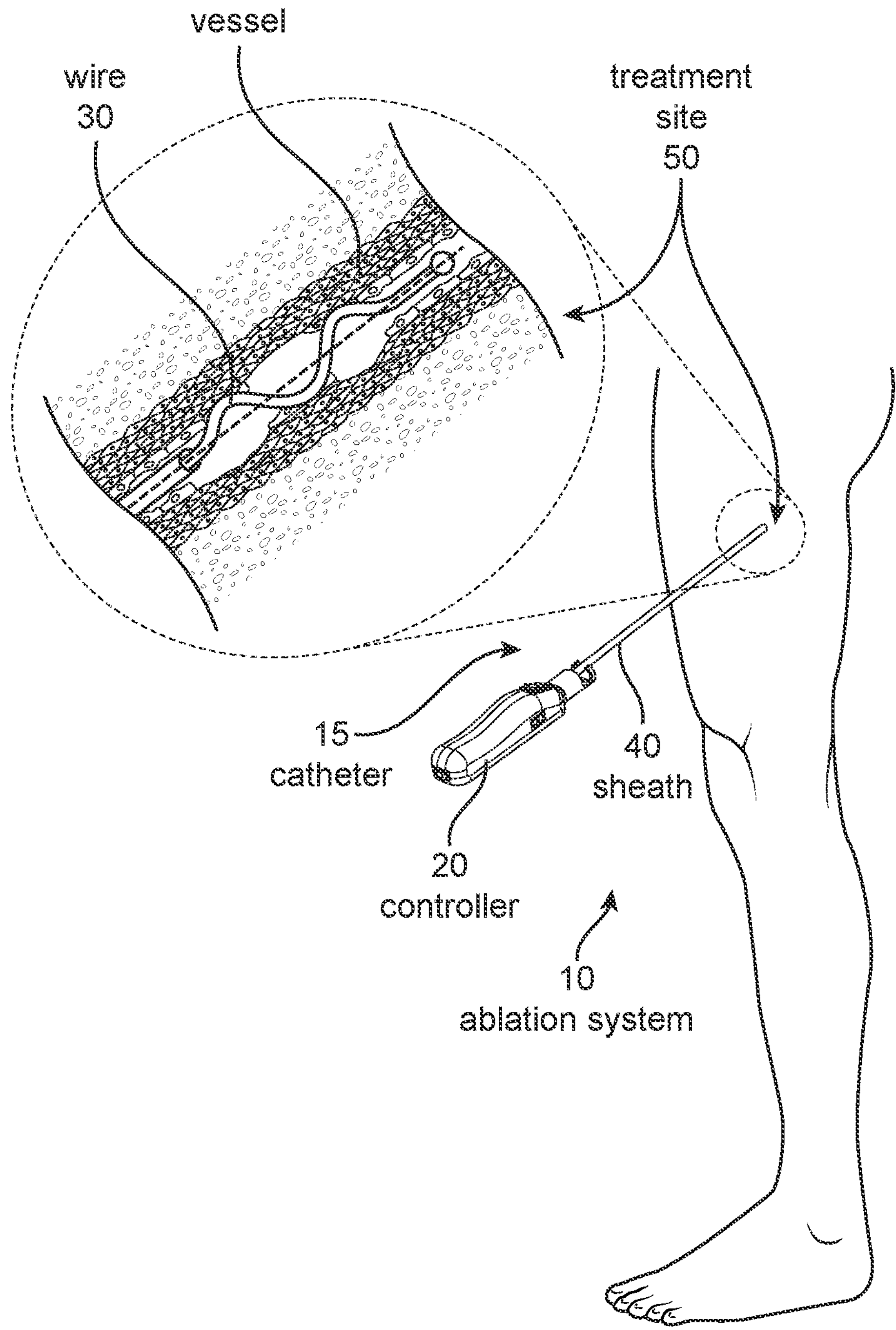
FIG. 1 illustrates a diagrammatic view of an ablation system as it may appear within a patient.

10—Ablation system
15—Catheter
20—Controller
30—Wire
40—Sheath
50—Treatment site
55—Treatment segment
60—Syringe
502—Proximal controller end
504—Distal controller end
506*a*—Switch
506*b*—Switch
508—Display
602—Slot
604—Inflation tuohy
606—Power supply
608—Actuator
610—Motor
702—Body
704—Saddle
706—T-fitting
708—Proximal body end
710—Distal body end

712—First direction
802—Body
804—T-fitting
806—Proximal body end
808—Distal body end
810—First direction
902—Body
904—T-fitting
906—Proximal body end
908—Distal body end
910—Pull tab
912—Light emitting diode (LED)
914—Actuator
916—First direction
1002—Sterile pack
1004—Slit
1102—Expandable foot
1104—Torque knob
1106—Arm
1202—Proximal wire end
1204—Distal wire end
1206—Aperture
1208—Central axis
1210—Weighted tip
1302—Circular cross-sectional profile
1304—Flat bar cross-sectional profile
1306—Triangular cross-sectional profile
1502—Thick diameter
1504—Thin diameter
1602—Triangular sinusoidal profile
1604—Triangular peak
1702—Stranded cable
1802—Helical hollow strand
1902—Spring-like construction
2002—Cage-like construction
2302—Sinusoidal crossing profile
2402—Spring-like crossing profile
2502—Three-dimensional crossing profile
2602—Proximal feature
2604—Balloon
2606—Offset balloon
2608—Cage
2610—Grooved solid
2612—Impeller
2614—Sponge-like solid
2616—Sinusoidal urge
2702—Distal feature
2704—Single blade impeller
2706—Cage
2708—Grooved solid
2710—Impeller
2712—Sponge-like solid
2802—Hemispherical tip
2804—Offset weighted tip
2806—Balloon tip
2902—Supplementary wire
2904—Heated wire
2906—Porous surface geometry
**3002*a***—Additional geometry
**3002*b***—Additional geometry
**3002*c***—Additional geometry
**3002*d***—Additional geometry
3102—Luer hub
3104—Luer
3202—Donut
3204—Distance marking
3206—Warning track
3302—Power supply
3304—Actuator
3306—Limit switch
3308—Motor
3310—LED
3312—Resistor
3400, 3402, 3304, 3406, 3408, 3410, and 3412—Method steps
3500, 3502, and 3504—Method steps
3600, 3602, and 3604—Method steps
3700, 3702, and 3704—Method steps
3800, 3802, and 3804—Method steps
3900, 3902, 3904, and 3906—Method steps
4000 and 4002—Method steps
4100, 4102, 4104, 4106, 4108, and 4110—Method steps
4200, 4202, 4204, 4206, and 4208—Method steps
4300, 4302, 4304, and 4306—Method steps
4400, 4402, and 4404—Method steps
4500, 4502, 4504, 4506, and 4508—Method steps
4600, 4602, and 4604—Method steps
4700, 4702, 4704, 4706, 4708, and 4710—Method steps
4800, 4802, and 4804—Method steps
4900, 4902, 4904, and 4906—Method steps
5000, 5002, 5004, 5006, 5008, 5010, and 5012—Method steps

DETAILED DESCRIPTION

The present disclosure describes systems and techniques for treating vascular disorders such as varicose veins. Some existing prior art systems include the use of highly complicated interventional devices (e.g., ablation catheters), which involve significant user training to enable correct and effective use due to the devices' requirements for the user to multitask while performing complicated dexterous techniques.

For instance, certain sclerotherapeutic catheters require the user (e.g., a clinician) to operate a first manual control (e.g., a syringe plunger) to infuse a chemical agent, such as a sclerosant, into a target vessel, while simultaneously operating a second, distinct manual control to longitudinally translate (e.g., distally advance and/or proximally withdraw) the catheter to disperse the chemical agent throughout the target vessel. In some such examples, the secondary control merely consists of the clinician manually pushing and/or pulling the catheter through the patient's vasculature. Such systems are not widely regarded to be user-friendly or patient-friendly.

Furthermore, some vascular treatment devices incorporate mechanical-based ablation features in addition to, or instead of, chemical-only-based ablation. In many cases, mechanical ablation improves the effectiveness of the treatment, but greatly complicates the operation of the device by not only incorporating yet another manual control to actuate a motion (e.g., rotation) of a mechanical agitator of the ablation device, but also requiring the clinician to consciously manage relative rates between all three aspects—i.e., a rate of longitudinal translation through the vessel, a rate of fluid infusion, and a rate of mechanical agitation.

In other words, many traditional sclerotherapy treatments and devices require the clinician to manually infuse a "steady" flow of sclerosant, manipulate a separate control (e.g., squeeze a trigger) to actuate an abrasive element to mechanically disturb the vessel wall, and also simultaneously manually withdraw the catheter at a consistent rate. The required cognitive load and skill of the user to simultaneously accomplish all of these steps is high, leading to a greater likelihood of errors due to mismatching the amount of mechanical ablation performed and the amount of sclerosant delivered to the target treatment site with an inconsistent withdrawal rate of the catheter. This not only creates a perception of a difficult-to-use device but also may lead to inferior or incomplete venous ablation, e.g. if an insufficient amount of sclerosant is delivered, or if an insufficient amount of mechanical abrasion is performed with a withdrawal speed that is too fast.

Additionally, the present disclosure describes systems and methods for controlling a catheter, perhaps a catheter including a wire. These controls include the unveiling of a wire from a lumen within a catheter and exposing said wire to treat a treatment site, as well as directional control of a catheter tip. Some existing solutions include the use of steerable catheter tips and electronic-based delivery/wire unveiling systems. The present disclosure permits manual control of wire unveiling, as well as distal catheter tip directional control.

FIG. 1 illustrates a diagrammatic view of an ablation system 10 as it may appear while a procedure is occurring on a patient's leg. A sheath 40 and a wire 30 are introduced to treatment site 50 via direct access to the vein being treated. Here, the wire 30 is shown as released from the sheath 40 prior to or during the procedure. The operator initiates the procedure from the controller 20.

Figure 2:
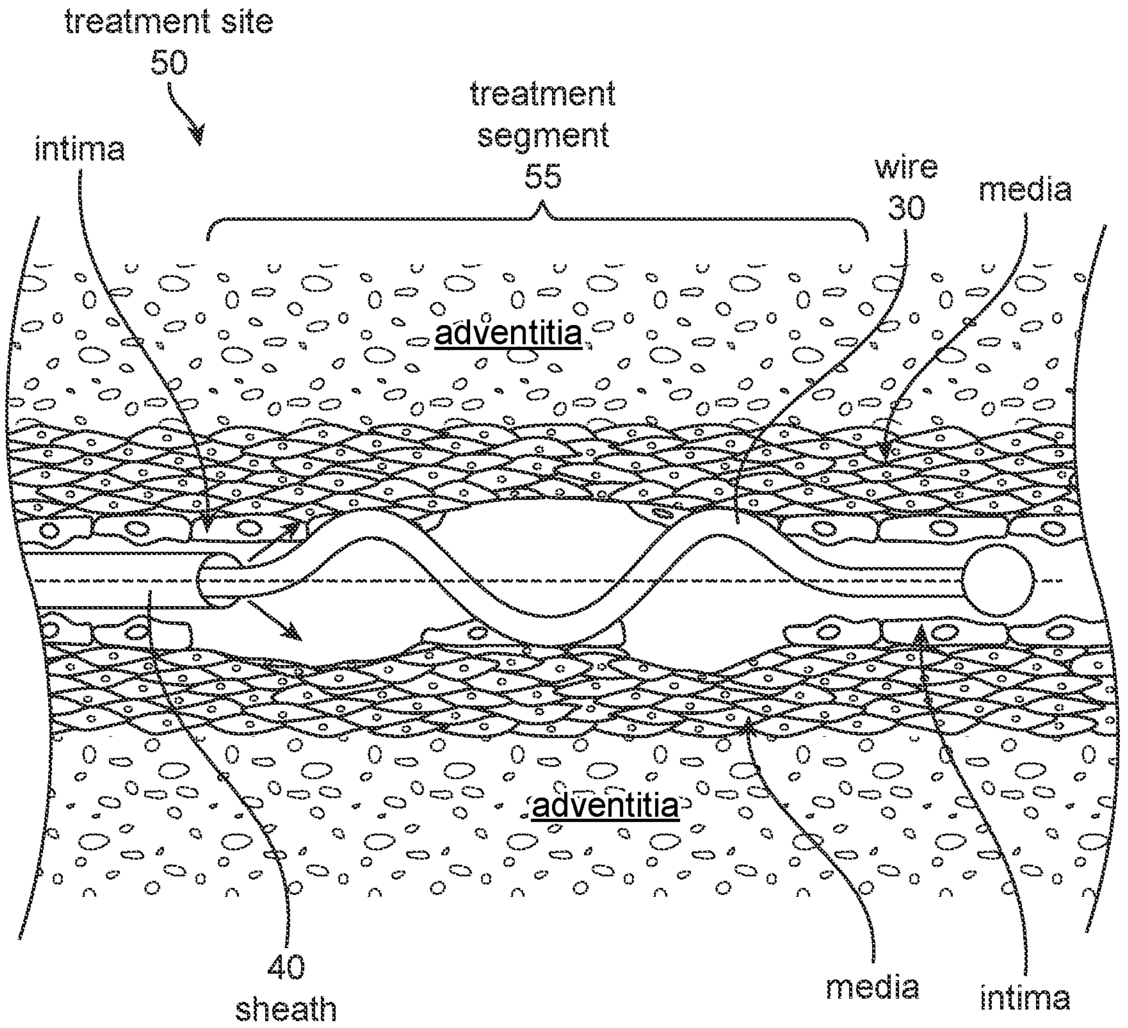
FIG. 2 illustrates a side view of an example wire within a vessel.
Figure 3:
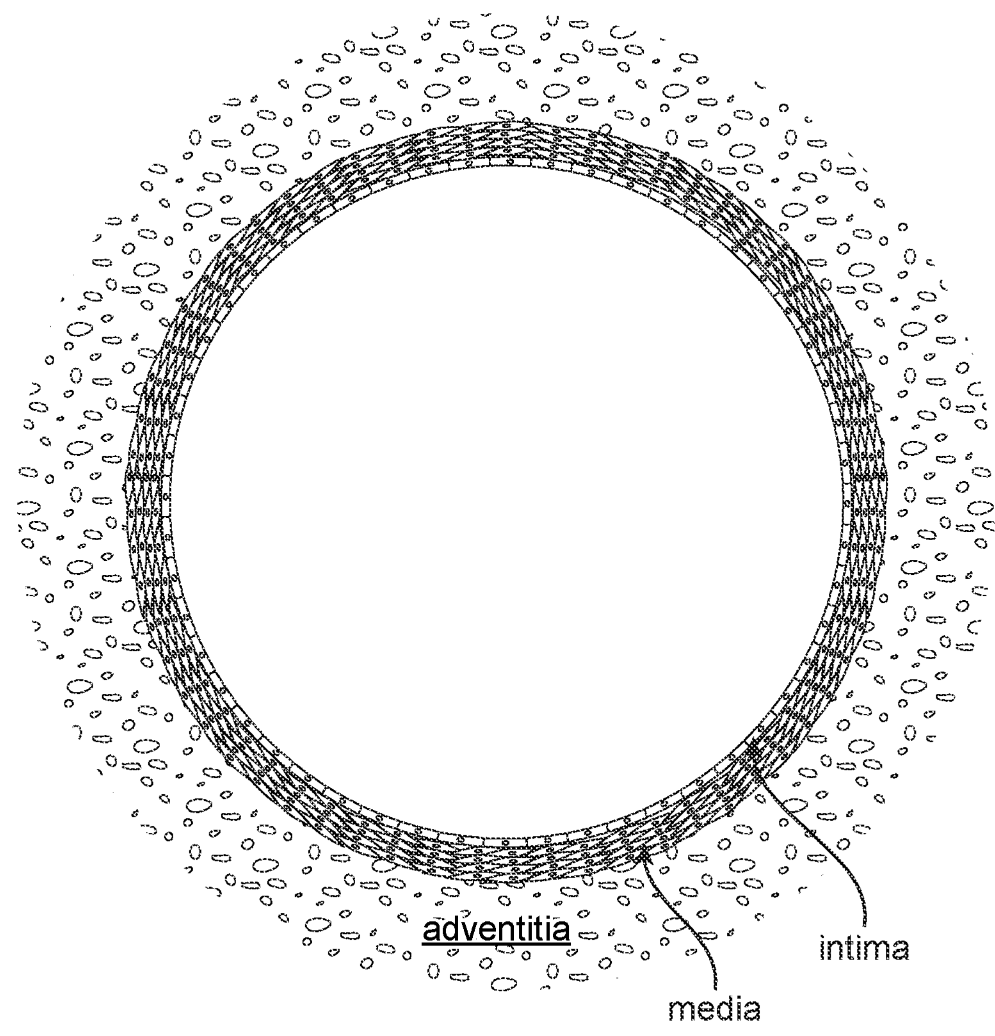
FIG. 3 illustrates a cross-sectional view of an example vessel.

FIG. 2 illustrates a side view of a wire 30 within a vessel, according to some examples. FIG. 3 illustrates a cross-sectional view of an example vessel, to better show the intima, media, and adventitia. As can be seen in FIG. 2, the wire 30 may extend through a working lumen of a sheath 40. This figure shows the wire 30 penetrating and/or disturbing the intima and making physical contact with the media at a treatment site 50. The intima in the locations affected by the rotating wire is thereby destroyed.

Because the length of the wire 30 exposed to the treatment site 50 is capable of making contact with a length of the vessel, rather than just a perimeter of the vessel, the treatment site 50 will often be called the treatment segment 55 throughout this disclosure. This ability to treat a treatment segment 55 rather than just a perimeter of the treatment site 50 enables to use of segmental mechanical or mechanochemical ablation. As an operator would now be able to treat a treatment segment 55 all at once, the need to withdraw a catheter 15 while at the same time injecting a drug into the treatment site 50 is rendered unnecessary. Thus, the operator may now focus on injecting the drug at a proper rate in isolation, and once the drug is injected, then moving the catheter 15 during periods of time during which the drug is not being administered. This may cut the difficulty of such a procedure exponentially, as the operator would no longer need to divide their attention between controlling multiple rates of administrating treatment (i.e., injection rate and catheter 15 withdrawal rate), but rather, just one rate of treatment administration at a time. Stated differently, this permits the procedure to be separated into the actions of injecting and withdrawing, while never requiring that both of these actions need to be performed at the same time. Additionally, throughout this disclosure, the term "drug" or "sclerosant" is used. It is understood that any fluid may be delivered in combination with any portion of this disclosure where such a fluid may be delivered.

Figure 4A:
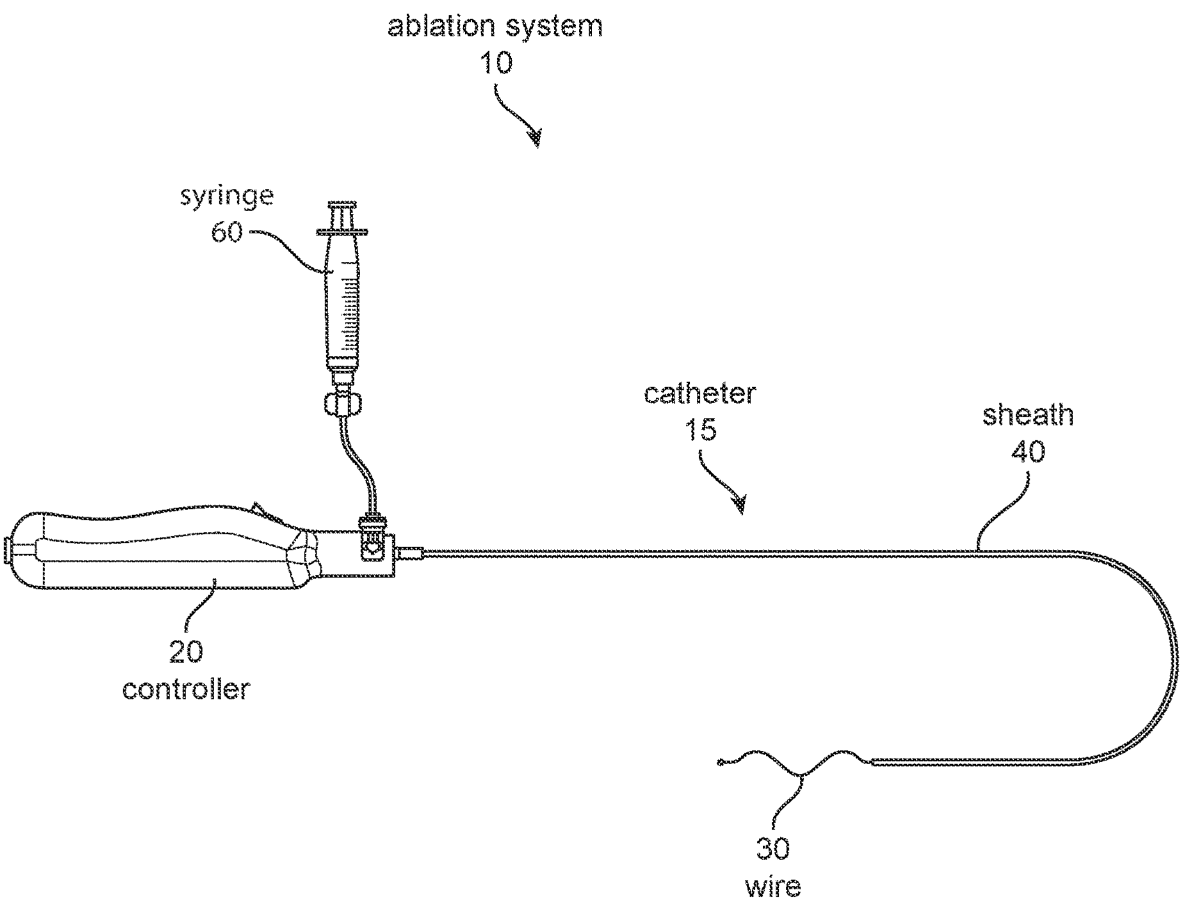
FIGS. 4A and 4B illustrate side views of an ablation system, according to some examples.
Figure 4B:
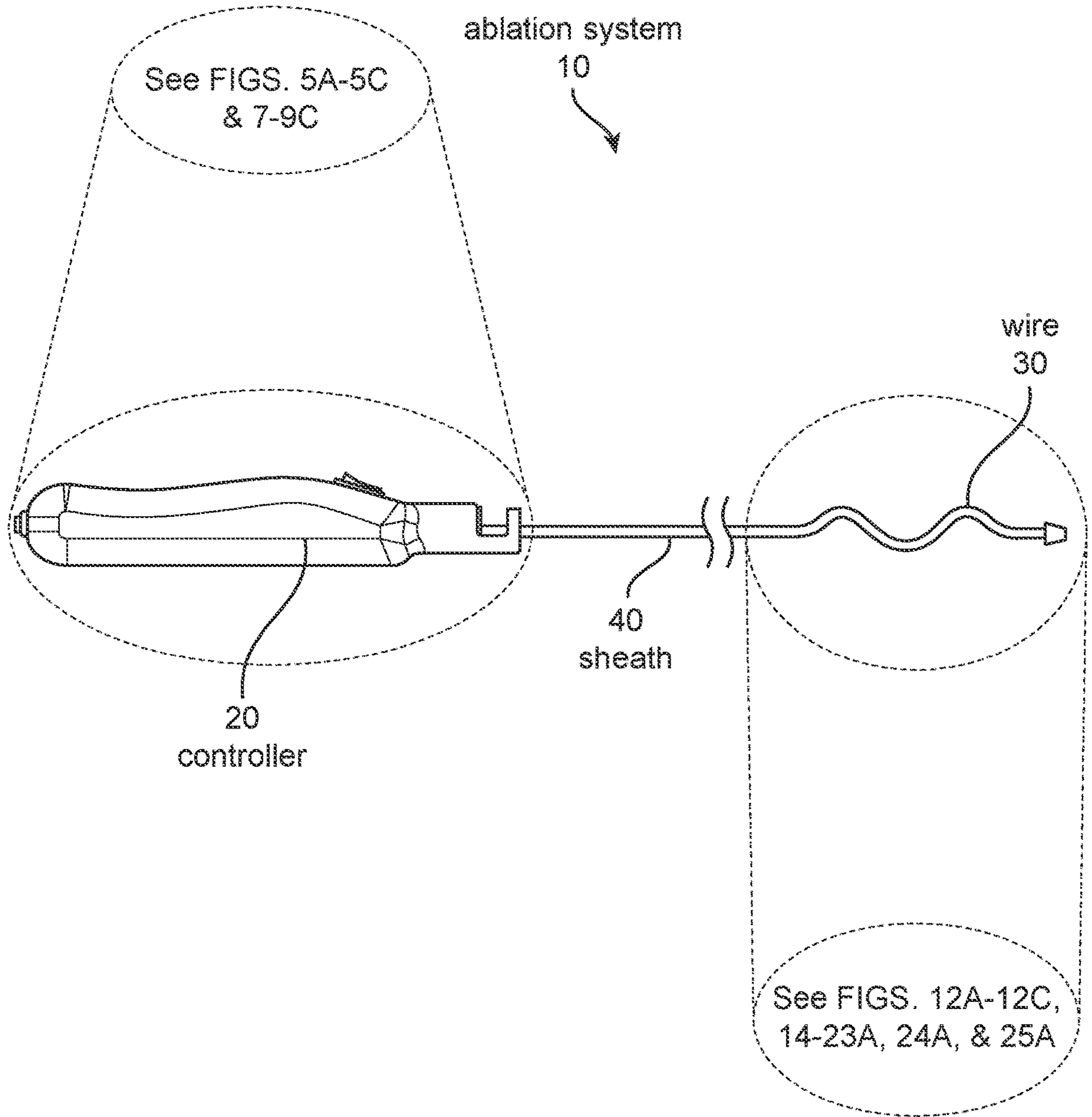

FIGS. 4A and 4B illustrate side views of an example of an ablation system 10. In some examples, the ablation system 10 includes a controller 20, which is shown and described in greater detail in FIGS. 5A, 5B, 5C, 7, 8, 9A, 9B, and 9C in various embodiments. The ablation system may also include a catheter 15, and in some examples, the catheter 15 includes a sheath 40 and a wire 30 extending through said sheath 40.

For the purposes of this disclosure, in some instances, the terms "catheter" and "sheath" are used interchangeably, and it is understood that the catheter may be more than just a sheath, such as examples including a wire. It is additionally understood that recitations of catheter could also include ablation systems without a sheath or a wire.

The sheath 40 may extend from the controller 20. In some examples, the wire 30 extends through a working lumen in the sheath 40. The wire 30 may be stored within the sheath 40 while the catheter 15 traverses a patient's vasculature until it reaches a treatment site 50, at which point the sheath 40 may be pulled back, or retracted, in order to unveil the wire 30. Various examples of the wire 30 are illustrated and discussed in greater detail in FIGS. 12A, 12B, 12C, 14, 15, 16, 17, 18, 19, 20, 21, 22A, 22B, 22C, 23A, 24A, and 25A. Also shown in FIG. 4A is a syringe 60 in fluid communication with the controller 20 at a distal end of the controller 20. The syringe 60 may provide a drug, such as sclerosant, through the catheter 15, the sheath 40, and/or the wire 30.

Figure 5A:
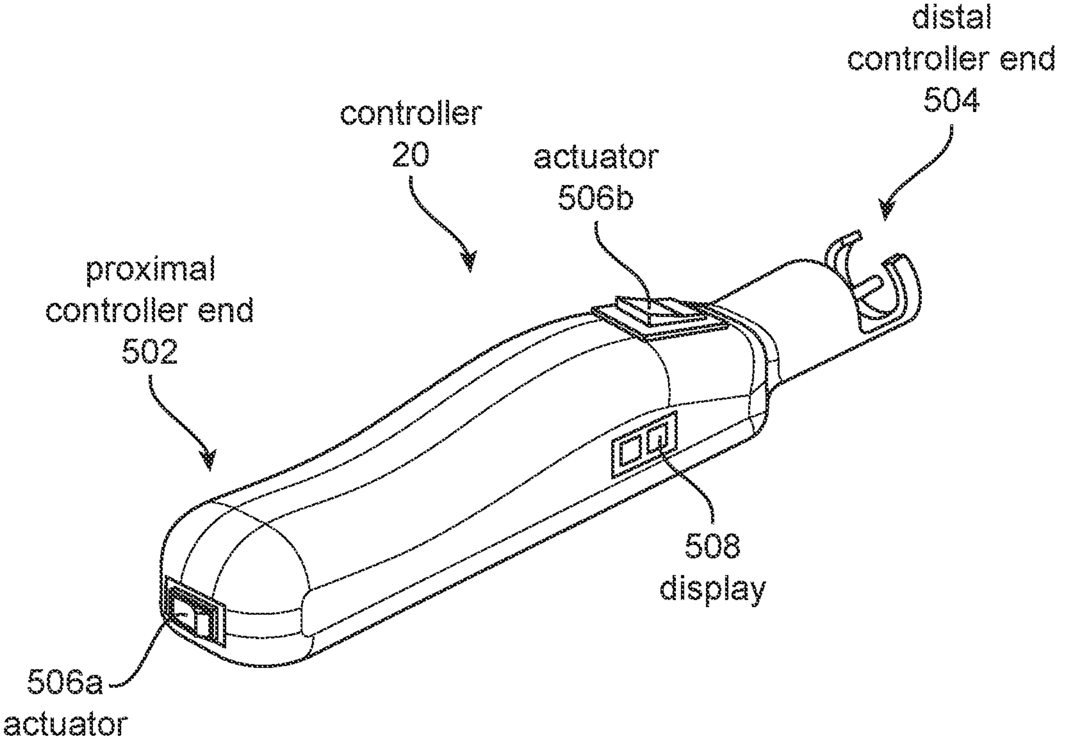
FIG. 5A illustrates a perspective view of an example controller.
Figure 5B:
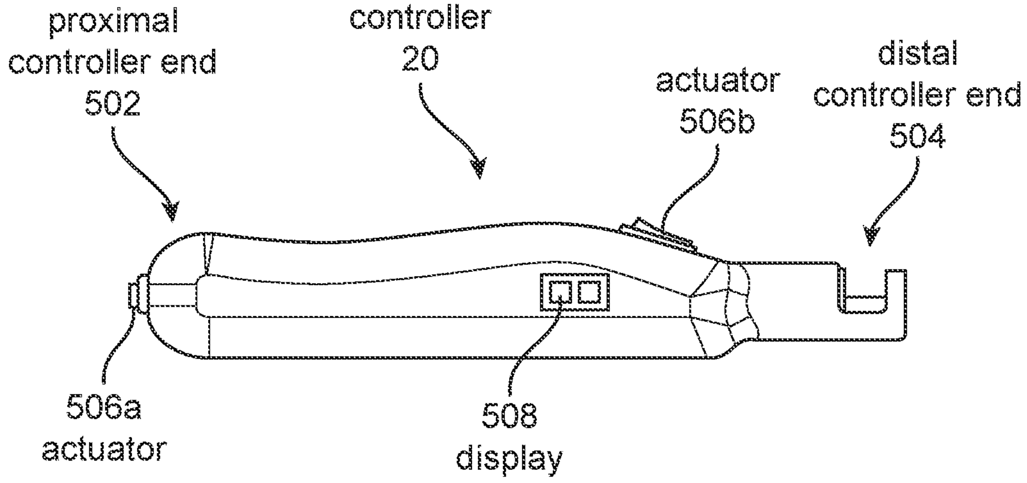
FIG. 5B illustrates a side view of the controller of FIG. 5A, according to some examples.
Figure 5C:
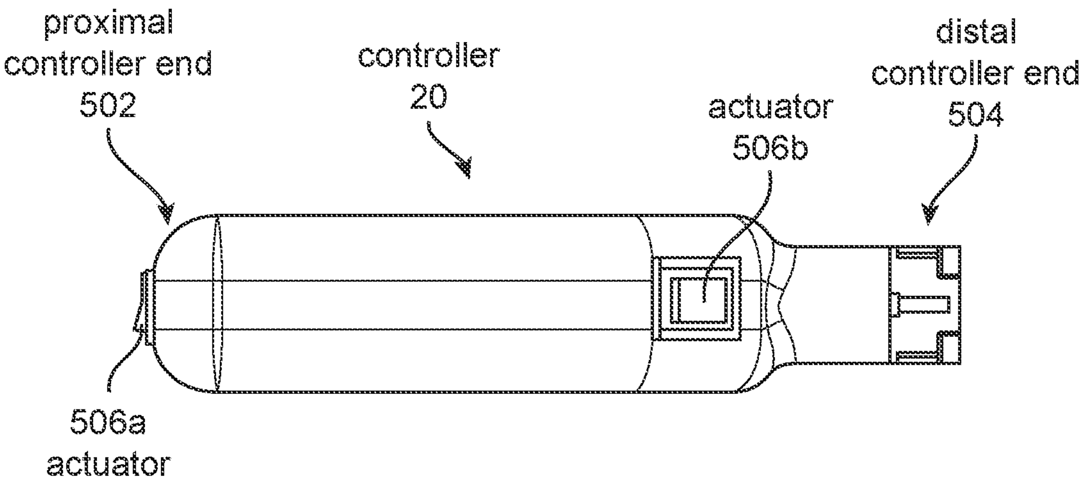
FIG. 5C illustrates a top view of the example controller of FIG. 5A.

FIG. 5A illustrates a perspective view of an example of a controller 20, and FIGS. 5B and 5C illustrate a side view and a top view, respectively, of the controller 20 of FIG. 5A. As can be seen in FIGS. 5A, 5B, and 5C, the controller 20 may include a proximal controller end 502 and a distal controller end 504 opposite the proximal controller end 502. The controller 20 may also include at least one actuator, as seen in actuator **506*a* and actuator 506*b*. As illustrated, multiple actuators may be implemented in or on a single controller 20**.

In FIGS. 5A, 5B, and 5C, actuator **506*a* is present at the base (proximal controller end 502) of the controller 20. Another actuator 506*b* is shown at the top of the controller 20 near the distal controller end 504. These actuators may operate as a sort of "and" gate, where both actuators must be activated (i.e., switched to an "on" position) in order for the controller 20 to turn on. This is useful as a safety precaution during transport of the controller 20 so that the controller 20** does not inadvertently turn on.

In some examples, either actuator **506*a* or actuator 506*b* may act as a power activation actuator, providing power to any internal circuitry, such as a motor. In such examples, the other actuator (i.e., actuator 506*b* if actuator 506*a* is the power activation actuator) may be a rotation activation actuator, thus telling the motor, in this example, to begin rotating. However, if desired, and as will be described and discussed in further detail in FIGS. 9A, 9B, and 9**C, the use of a single actuator would also work. The actuator may be any type of actuator, such as a button, a switch, a touch screen on a user interface, etc.

Also shown in FIGS. 5A and 5B is a display 508. The display 508 may provide information to the operator of the controller 20, such as the amount of time that has passed during a procedure, or the amount of time remaining in cases where the controller 20 is programmable to operate for a set duration.

Specifically, in light of mechanochemical ablation (or just mechanical ablation in instances where no drug is delivered), the display 508 may facilitate a segmental ablation technique. For example, once a catheter 15 has been inserted and located at a correct treatment site 50, once an operator has used an actuator to turn on a device, the display may count down the time until the treatment site has been abraded enough such that a drug should be delivered. Additionally, or alternatively, the display 508 may also countdown a time during which the drug should continue to be delivered, at the end of which the operator discontinues the injection of the drug.

In examples where the treatment site 50 includes a treatment segment 55, the display 508 may inform an operator of when the treatment segment 55 is done being treated, which would tell the operator is time to move the catheter 15 to the next, or a subsequent, treatment segment 55.

Figure 6A:
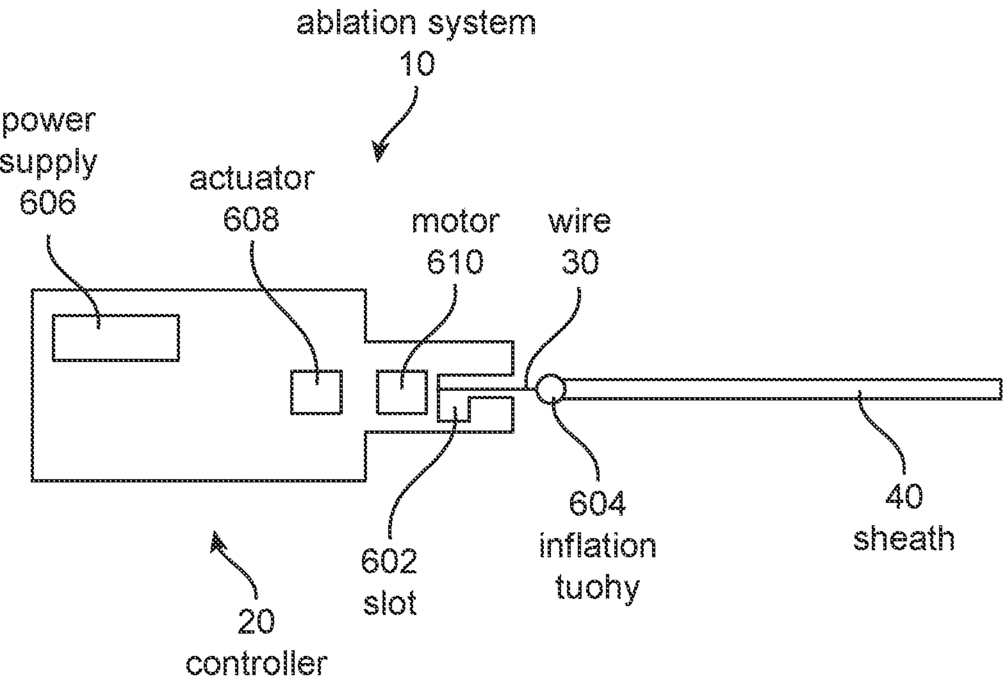
FIG. 6A illustrates a diagrammatic side view of an example ablation system.
Figure 6B:
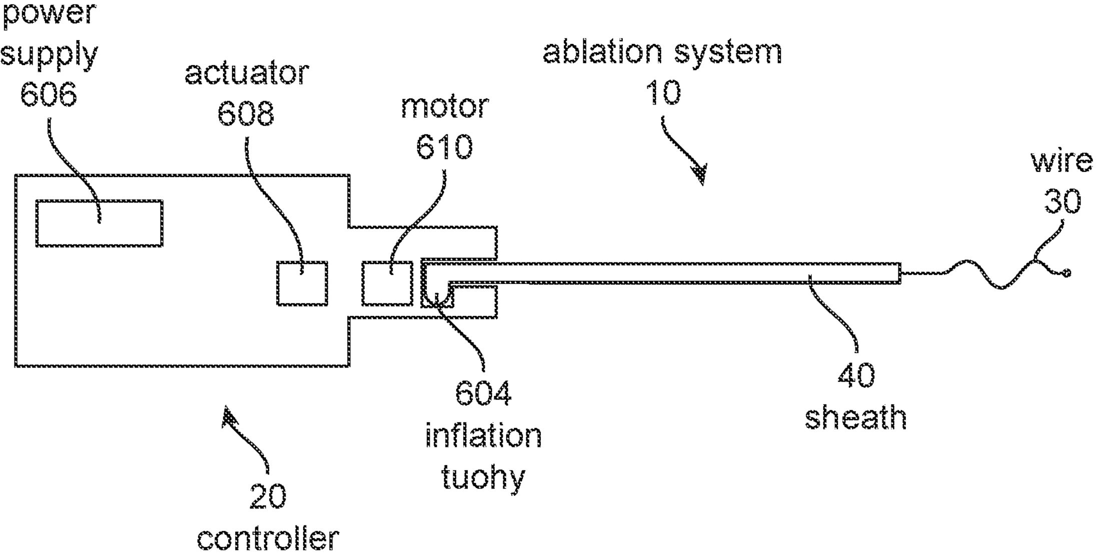
FIG. 6B illustrates a diagrammatic side view of the ablation system of FIG. 6A with the wire exposed.

FIG. 6A illustrates a diagrammatic side view showing the wire 30 enclosed in the sheath 40. FIG. 6B illustrates the diagrammatic side view of FIG. 6A, but with the wire 30 exposed from the sheath 40. As seen in both FIGS. 6A and 6B, the controller 20 may include a slot 602 in the distal controller end 504. At a proximal end of the sheath 40, an inflation tuohy 604 may be present. The wire 30 is delivered to a treatment site 50 while enclosed in the sheath 40 (in some examples). In other examples, the sheath 40 is detachable from the controller 20 and capable of being delivered to the treatment site 50 prior to the wire 30 being delivered to said treatment site 50.

Once the wire 30 reaches the treatment site 50, the wire 30 may be exposed from the sheath 40. In this regard, the sheath 40 may be retracted from the wire 30, whereby the sheath moves away from the treatment site 50 while leaving the wire 30 in place in the treatment site 50. The operator may perform this pull-back, or retractive, motion on the sheath 40 manually (as well be illustrated and discussed in FIGS. 7, 8, 9A, 9B, and 9C) and then rotates the sheath 40 in order to lock the inflation tuohy 604 in the slot 602. This locking of the inflation tuohy 604 in the slot 602 may prevent the sheath 40 from moving axially during a procedure.

As can also be seen in FIGS. 6A and 6B, the controller 20 may include a motor 610, such as an electric motor, which may be activated by an actuator 608. A power supply 606 is also included within the controller 20 (though the power supply 606 could be external to the controller 20, if desired). This power supply 606 permits the actuator 608 to connect power to the motor 610, thus effectuating rotation of the motor 610, and in turn effectuating rotation of the wire 30.

Throughout the present specification, the motor 610 may be described as coupling to, and effectuating rotation upon, the wire 30 and/or the catheter 15. These are used interchangeably through this specification, as either component may be what is coupled to the motor 610 and thereby rotates. Additionally, there may be intervening components between the motor 610 and the wire 30 and/or the catheter 15. For example, the wire 30 and/or the catheter 15 may couple, detachably or fixedly, to one or more hypotubes. In turn, these hypotubes may couple, again, either detachably or fixedly, to the motor 610.

It is understood that the diagrammatic side views of the controller 20 as shown in FIGS. 6A and 6B may be used in combination with any of the various controller 20 examples as shown and described previously in FIGS. 5A, 5B, 5C, as well as any of the various controller 20 as will be shown and described in FIGS. 7, 8, 9A, 9B, and 9C.

Figure 7:
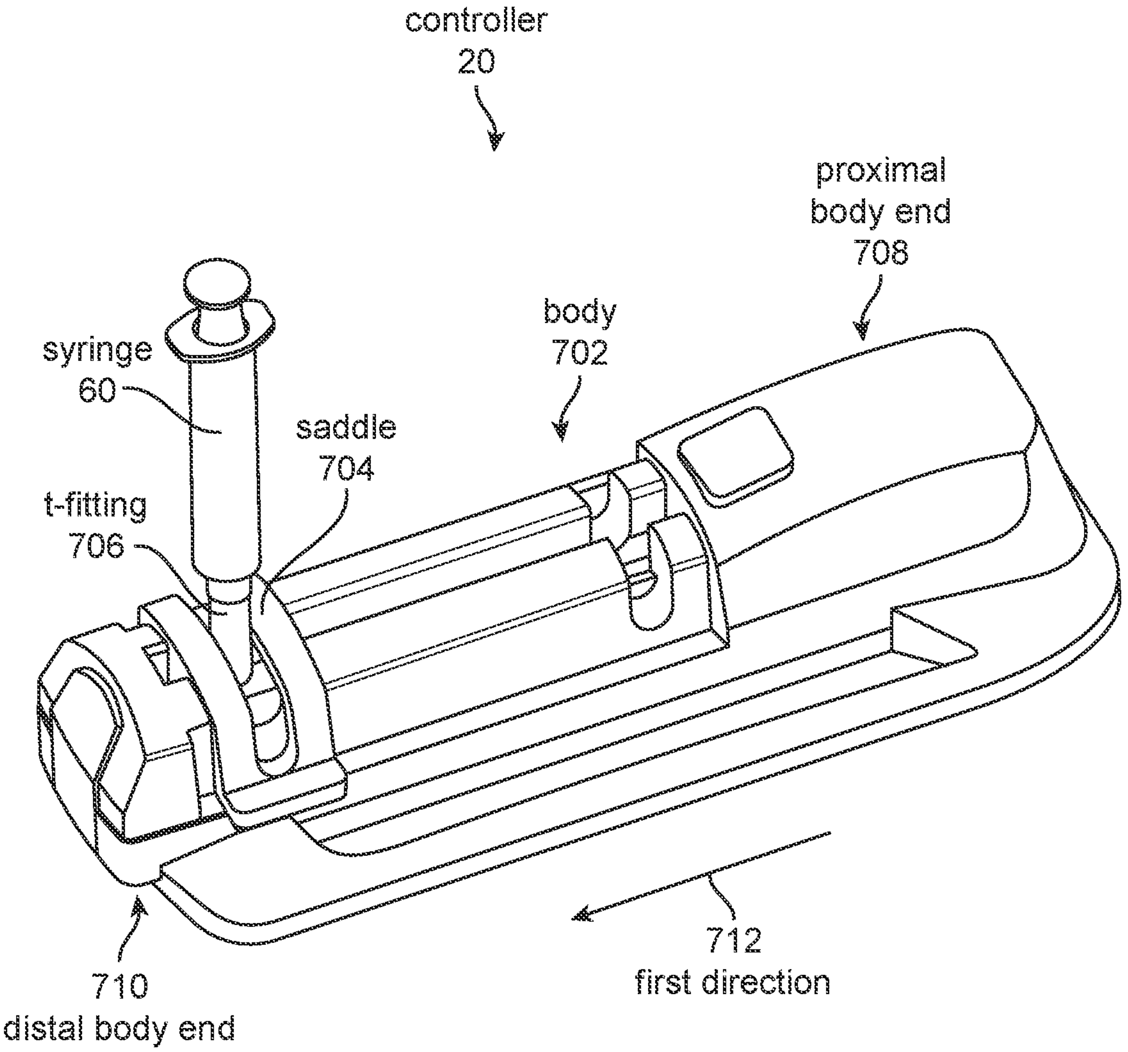
FIG. 7 illustrates a profile view of another example controller, according to some examples.

FIG. 7 illustrates a profile view of a controller 20, according to some examples. The controller 20 may include a proximal body end 708 and a distal body end 710 opposite the proximal body end 708. While not shown in FIG. 7, the controller 20 may removably couple to a catheter 15 at the distal body end 710.

As seen in FIG. 7, the controller 20 may include a flat, or at least partially flat, bottom portion, permitting the controller 20 to be placed on a tabletop or other working surface in order to facilitate the operation of said controller 20. While not shown in FIG. 7, but as seen and described in previous FIGS. 5A, 5B, and 5C, the controller 20 may be hand-held. This may make it such that the controller 20 is operated in a two-handed manner, wherein one hand would provide support for the controller 20, and the other hand would operate the controller 20. The controller 20 may also be removably coupled to any working surface not specifically described herein, i.e., the controller 20 does not need to be placed on a table or held in an operator's hand in order for the controller 20 to be operational.

As can also be seen in FIG. 7, the controller may include a body 702 and a saddle 704 slidably coupled to the body 702. The saddle 704 is capable of slidably moving in a first direction 712, as well as opposite this first direction 712. As shown in FIG. 7, the first direction 712 is considered the direction moving from the proximal body end 708 to the distal body end 710. A T-fitting 706 may be disposed within the body 106 of the controller 20 and at least partially surrounded by a center portion of the saddle 704. The T-fitting may be capable of slidably moving in the first direction 712, as well as opposite this first direction 712 in response to movements of the saddle 704. In examples of the controller 20 including a catheter 15 removably coupled to/through the distal body end 710, the catheter 15 may further be removably coupled to the T-fitting 706.

Such a catheter 15 may include a wire 30 for the purposes of abrading a vessel wall at a treatment site 50, as detailed in FIG. 2. In some procedures, it is desirable to keep the wire 30 contained within the catheter body, or a sheath 40, until said wire 30 has been delivered to the treatment site 50 in order to prevent premature abrasion of vessel walls, or stated another way, abrasion of vessel walls not intended for treatment. Once the catheter 15 reaches the desired treatment sire, the saddle 705 may move along the first direction 712 to expose or enclose the wire 30.

In other examples, the catheter 15 track or move to a treatment site 50 whereby the catheter exposes the wire 30. This may permit greater flexibility in designs where the wire 30 includes a shape that is larger than the sheath 40 opening. In some examples, once the wire 30 is enclosed by the sheath 40, the sheath 40 responds by expanding slightly in order to accept the wire 30 within its confines. This may limit the flexibility of the sheath 40, and therefore, exposing the wire 30 while tracking the catheter 15 to the desired treatment site 50 may permit greater flexibility in order to traverse a tortuous vasculature of a patient.

Throughout the specification, the catheter 15 is disclosed as including a wire 30. However, it is understood that the present specification is not limited to the use of a wire 30. The present specification also enables the use of a hypotube, a catheter shaft, or combinations thereof, and in combination with a wire 30.

As illustrated in the example controller 20 of FIG. 7, the saddle 704 is present at the distal body end 710. At this location, the wire 30 remains within a lumen of the sheath 40. As an operator moves the saddle 704 opposite the first direction 712 toward the proximal body end 708, the sheath 40 may be pulled back about the wire 30, exposing the wire 30. At this point, the wire 30 may be used to abrade the vessel wall.

The body 702 may include an actuator (such as actuator 506*a* or 506*b*, as described and discussed in FIGS. 5A, 5B, and 5C, actuator 608, as described and discussed in FIGS. 6A and 6B, and/or actuator 914 as will be discussed in further detail in FIGS. 9A, 9B, and 9C). In some examples, this actuator 506*a*, 506*b*, 608, and/or 914 controls circuitry and/or a motor (such as the motor 610 as described and discussed in FIGS. 6A and 6B, and/or the motor 3308 as will be discussed in further detail in FIG. 33) within the body 702. This actuator 506*a*, 506*b*, 608, and/or 914 may control the rotation of the wire 30, facilitating abrasion of the vessel wall. When this abrasion is completed, the operator may move the saddle 704 in the first direction 712, to push the sheath 40 forward again, thereby enclosing (or capturing, resheathing, etc.) the wire 30 within the sheath 40 once again, permitting safe removal of the catheter 15 from the vasculature of the patient.

FIG. 7 also shows a syringe 60 removably coupled to the T-fitting 706 through the saddle 704. This syringe 60 may be in fluid communication with the catheter 15 in examples where the catheter 15 is present. In some examples, the catheter 15 includes a fluid lumen (such as a working lumen through the sheath 40), permitting fluid from the syringe 60 to pass through the catheter 15 when the syringe 60 is depressed. This may be useful in procedures such as sclerotherapy, where a fluid drug, such as sclerosant, is recommended for delivery to a treatment site 50 either before, in tandem with, or after abrasion of the vessel wall.

The syringe 60 is depicted as extending perpendicular to the first direction 712. This is as an example only, and it is understood that the syringe 60 may be placed at any angle so as to provide the best ergonomics and/or comfort to the operator. In some examples, the syringe 60 acts as a type of handle for the operator, permitting easy control of the saddle 704 and the T-fitting 706 in moving in both the first direction 712 and opposite the first direction 712.

The saddle 704 and the T-fitting 706 may slide due to manual control of the syringe 60, but the T-fitting 706 may also be operated by direct control of the saddle 704, such as through an operator pushing on the saddle 704 with one of their hands while operating the depression of the syringe 60 with their other hand. As will be explored in FIGS. 9A, 9B, and 9C, the saddle 704 may further include pull tabs (such as the pull tabs 910 of FIGS. 9A, 9B, and 9C) to facilitate manual movement of the saddle 704. In these examples, the syringe 60 would move along with the T-fitting 706 but would not be the cause of such a movement.

Additionally, while not explicitly shown in FIG. 7, in some examples, the syringe 60 may not be removably coupled to the T-fitting 706. In such examples, an extrusion tube/infusion tube may connect the syringe 60 to a removably coupled catheter 15. This would permit the syringe 60 to not be coupled to the T-fitting 706 and, therefore, not be coupled to the controller 20. Instead, the syringe 60 would be coupled to flexible tubing, permitting greater freedom of movement of the syringe 60 separate from the controller 20 when desirable.

Also illustrated in FIG. 7 is a slot in the saddle 704 perpendicular to the first direction 712 and extending at least partially about the saddle 704. This slot may permit the syringe 60 to perform rotational movement about the body 702. In some examples, when an operator rotates the syringe 60 about the body 702, it creates a torque on a wire 30, perhaps a wire 30 in a removably coupled catheter 15, permitting manual control of a distal end of the wire 30. This may permit the operator to make fine movements of such a distal end of the wire 30 in the treatment site 50 in order to make better abrasive contact with the vessel walls and/or facilitate traversal of the tortuous vasculature of the patient.

While not illustrated in FIG. 7, the T-fitting 706 may include a luer (such as the luer 3104 as seen and described below in FIG. 31). This luer may be configured to detachably couple the syringe 60 to the T-fitting 706. In examples including such a luer, the luer may be configured to rotate about a direction perpendicular to the first direction 712. This rotation may include any angle of rotation, including full 360-degree circumferential rotation about the body 702.

Once a syringe 60 has been detachably coupled to the luer, this rotational movement would likely be limited in order to prevent over-rotation of the syringe 60. In this configuration, the syringe 60 may be configured to control the rotation of the luer. Similar to the above disclosure, the rotation of the luer may create torque on a wire 30, thereby permitting manual control of a distal end of the wire 30.

The luer may have an O-ring on a proximal side, facilitating the prevention of fluid leakage during the infusion This O-ring may also grip onto the wire 30 while simultaneously being attached to the catheter sheath 40 so that when the luer is rotating, the catheter sheath 40 also rotates, and the O-ring of the luer will attempt to rotate the wire 30 at the same time.

While not shown in FIG. 7, in some examples, the luer is not present within the device body. In such examples, the luer could be an off-the-shelf stopcock or three-way valve that accepts the catheter sheath 40. This would permit a user to fully remove the sheath 40 from the device while leaving the wire 30 in place. This may facilitate the use of the device in situations where another catheter sheath 40 is in situ—such as a guidewire catheter. A second catheter sheath 40 may not fit within the vasculature next to a preexisting catheter sheath 40, so by removing the catheter sheath 40 from the present device, the wire 30 could still be inserted into the treatment site 50.

Another advantage of being able to remove the sheath 40 is that the sheath 40 may be tracked to the treatment site first. Also, removing the catheter sheath 40 from the wire 30 may permit the sheath 40 to be tracked over an already placed guidewire. Once the catheter sheath 40 has been placed, the guidewire, if present, may be removed, permitting the device to be advanced further into the vasculature.

Figure 8:
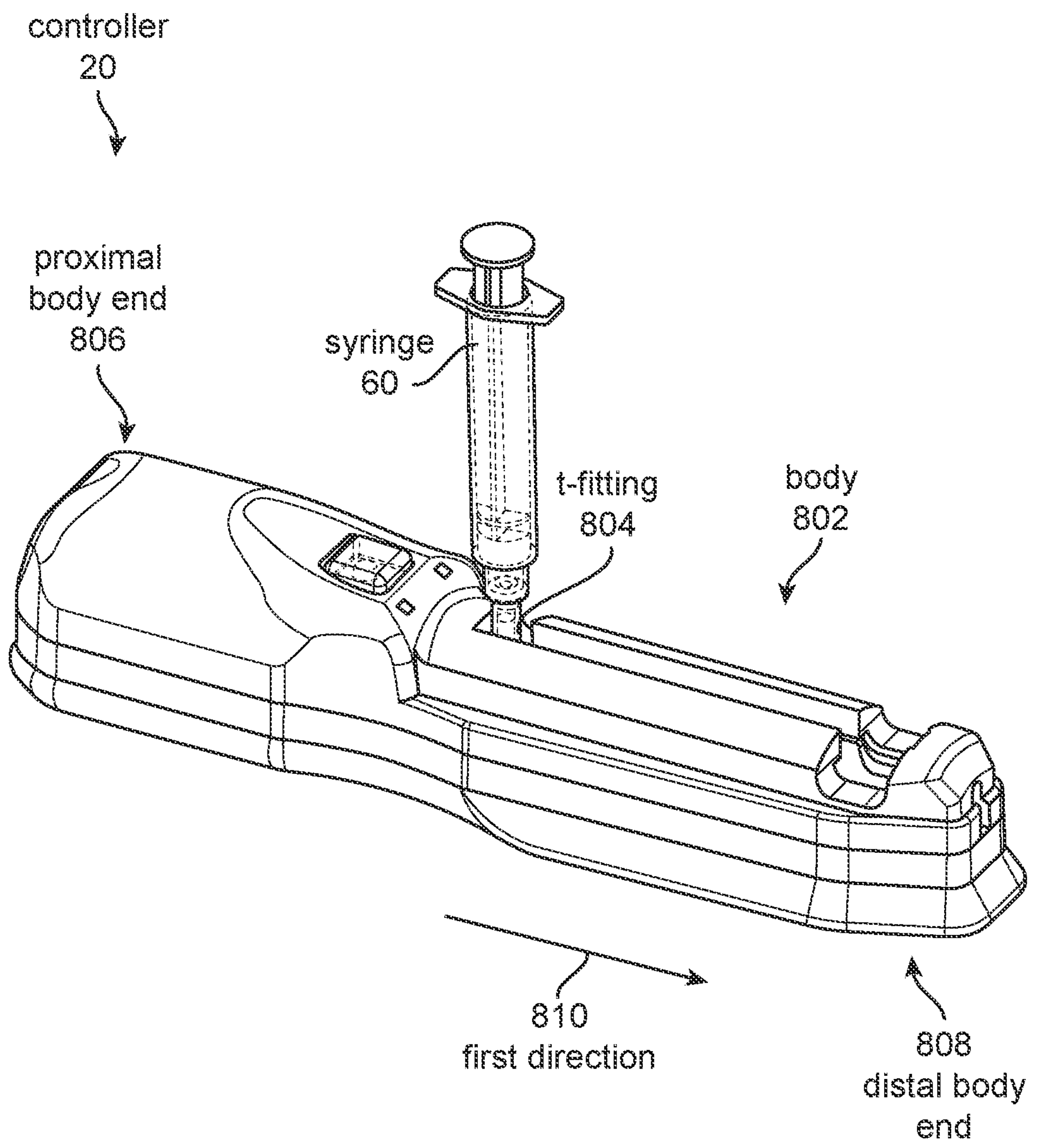
FIG. 8 illustrates a profile view of another example controller, according to some examples.

FIG. 8 illustrates a profile view of a controller 20, according to some examples. The example controller of FIG. 8 shares many similarities with the example controller of FIG. 7, much of which will be reiterated here. The controller 20 may include a proximal body end 806 and a distal body end 808 opposite the proximal body end 806. While not shown in FIG. 8, the controller 20 may removably couple to a catheter 20 at the distal body end 808.

As seen in FIG. 8, the controller 20 may include an at least partially flat bottom portion, permitting the controller 20 to be placed on a tabletop, or another working surface, in order to facilitate the use of said controller 20. While not shown in FIG. 8, but as described previously in FIGS. 5A, 5B, and 5C, the controller 20 may be hand-held, making use of the controller 20 a two-handed operation wherein one hand would provide support for the controller 20, and the other hand would operate the controller 20. The controller 20 may also be removably coupled to any other working surface not described herein, i.e., the controller 20 does not need to specifically be placed on a tabletop or held in an operator's hands in order for the controller 20 to be operational.

As can be seen in FIG. 8, the controller 20 may include a body 802. Dissimilar to the example controller 20 of FIG. 7, the example controller 20 of FIG. 8 does not include a saddle slidably coupled to the body 802. In this example, a T-fitting 804 may be disposed within the body 802 of the controller 20. The T-fitting 804 may be capable of slidably moving in a first direction 810, as well as opposite the first direction 810, wherein the first direction 810 is the direction of movement from the proximal body end 806 to the distal body end 808. In examples of the controller 20, including a catheter removably coupled to and/or through the distal body end 808, the catheter may further be removably coupled to the T-fitting 804.

Also illustrated in FIG. 8 is the T-fitting 804 present at a point nearest the proximal body end 806. At this location, the sheath 40 would be retracted about the wire 30, exposing the wire 30 to a treatment site 50. In some examples, the catheter may be delivered in this configuration, but it is likely that the wire 30 would be delivered to the treatment site 50 while still within the sheath 40 to avoid unintentional abrasion of vessel locations that are not the treatment site 50. After a treatment has been performed, the operator may move the T-fitting 804 along the first direction 810 in order to sheath the wire 30 once again, permitting the safe removal of the catheter from the vasculature of the patient.

FIG. 8 also shows a syringe 60 removably coupled to the T-fitting 804. The syringe 60 may also be in fluid communication with the catheter, if/when a catheter is present. In some examples, the catheter includes a fluid lumen, permitting fluid from the syringe 60 to pass through the catheter when the syringe 60 is depressed. As described previously, this is useful for procedures such as sclerotherapy, where a fluid drug, such as sclerosant, is recommended to be used either before, in tandem with, or after abrasion of the vessel wall.

The syringe 60 is shown as extending perpendicular to the first direction 810. This is by example only, and it is understood that the syringe 60 may be placed at any angle so as to provide the best ergonomics or comfort to the operator. In some examples, the syringe 60 acts as a type of handle for the operator, permitting easy control of the T-fitting 804 in slidably moving in both the first direction 810 and opposite the first direction 810.

Figure 9A:
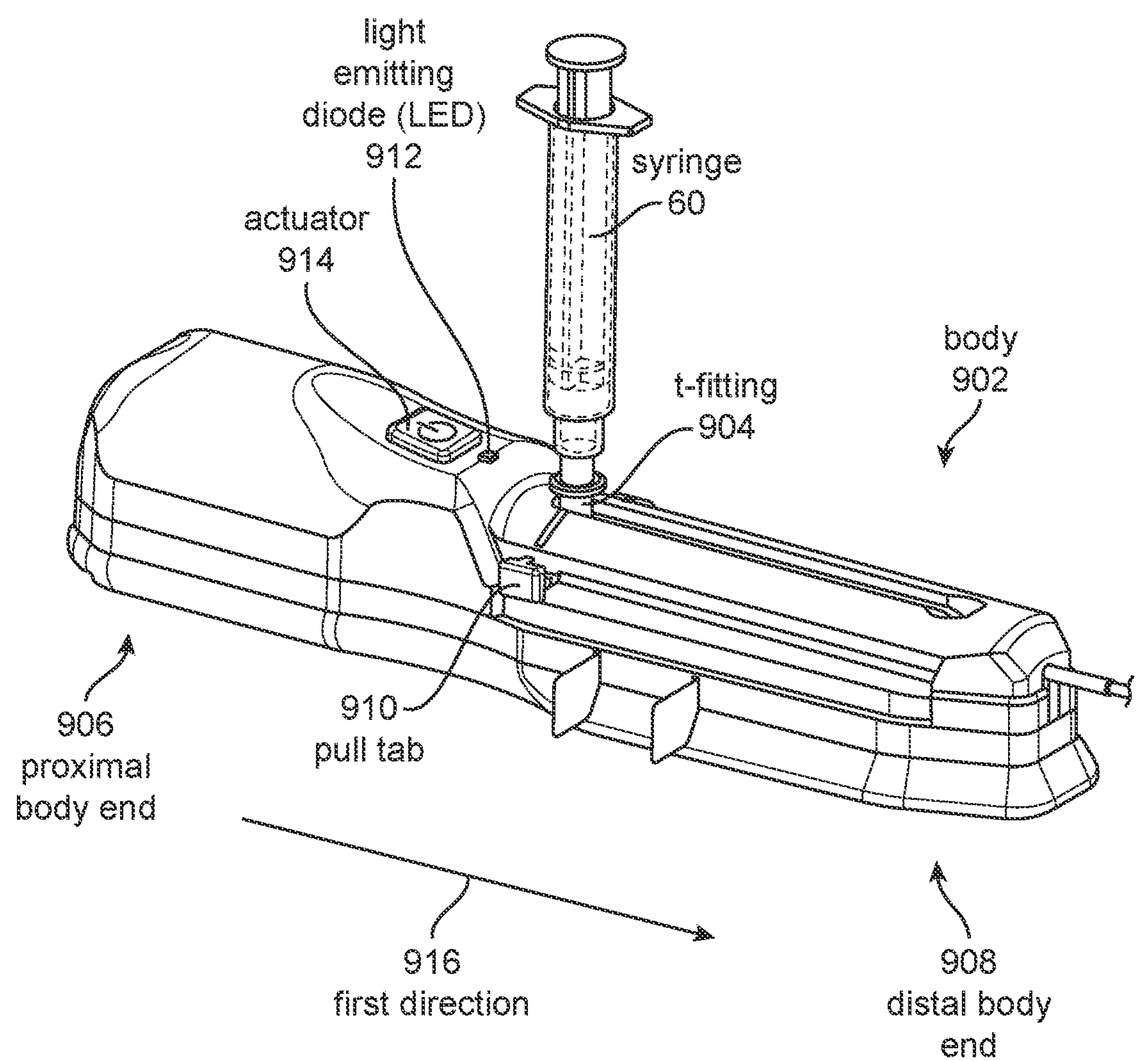
FIG. 9A illustrates a profile view of another example controller, according to some examples.

FIG. 9A illustrates a profile view of an additional example controller. FIG. 9B shows the controller 20 of FIG. 9A from a side view, and FIG. 9C shows the controller of 9A from a top view, without a syringe 60 present Similar to the controllers 20 of FIGS. 7 and 8, the controller 20 of FIGS. 9A, 9B, and 9C includes a body 902 having a proximal body end 906 and a distal body end 908 opposite the proximal body end 906. The beginning portion of a catheter 15, not labeled but shown, can be seen entering the body 902 through the distal body end 908.

A T-fitting 904 is illustrated, in this example, located at least partially within the body 902. The T-fitting 904, as described previously, may be or include a luer hub and luer for detachably receiving a syringe 60. This T-fitting may be coupled to a saddle, such as the saddle 704 of FIG. 7. The saddle in FIGS. 9A, 9B, and 9C, however, is mostly obscured by the body 902, as this saddle is located at least partially, if not mostly, within the body 902. Portions of the saddle stick out from the sides of the body 902, however, and these are shown as pull tab(s) 910. It is understood that the decision to use the term "pull tab(s)" is solely a lexicographical choice, and any other fitting term, such as "finger pad(s)" or equivalent may be substituted.

Similar to the disclosure of FIGS. 7 and 8, the controller 20 may be capable of maneuvering a sheath 40 about a wire 30. FIGS. 9A and 9B illustrate the syringe 60 and the T-fitting 904 located toward the proximal body end 906. FIG. 9C, while not illustrating a syringe 60, also shows the T-fitting 904 located toward the proximal body end 906. In all instances, this may indicate that the sheath 40 is fully retracted about the wire 30, exposing the wire 30. This is likely, but not necessarily, indicative that the catheter 15 is located at a treatment site 50 and the wire 30 has been exposed in order to provide a treatment.

Once a treatment has been completed, the syringe 60, and the T-fitting 904, may be pushed along the first direction 916, which runs from the proximal body end 906 to the distal body end 908. In FIG. 7, it was discussed how the saddle 704 itself could be manipulated by the operator in order to push and pull the syringe 60 and T-fitting 904. Similarly, in FIGS. 9A, 9B, and 9C, the pull tab(s) 910 may be manipulated, either instead of, or in addition to, the syringe 60 and the T-fitting 904. In this example, pushing the syringe 60, T-fitting 904, and/or pull tab(s) 910 causes the sheath 40 to extend about the wire 30, thereby enclosing or capturing the wire 30. In this configuration, the wire 30 may be in a less expanded state, allowing for easier, or safer, removal of the catheter 15 from the patient (or insertion into the patient, if this is occurring prior to the treatment being delivered).

In opposition to this pushing motion, once a catheter 15 has been delivered to a treatment site 50, the operator may then pull the syringe 60, the T-fitting 904, and/or the pull tab(s) 910 in order to retract the sheath 40. This retraction of the sheath 40 exposes the wire 30, and in instances when a distal end of the wire 30 includes a shaped profile, the wire 30 may expand into this shaped profile (or further expand into this shaped profile as the case may be) in order to make contact with the vessel walls, allowing for abrasion to occur during a treatment.

Figure 9B:
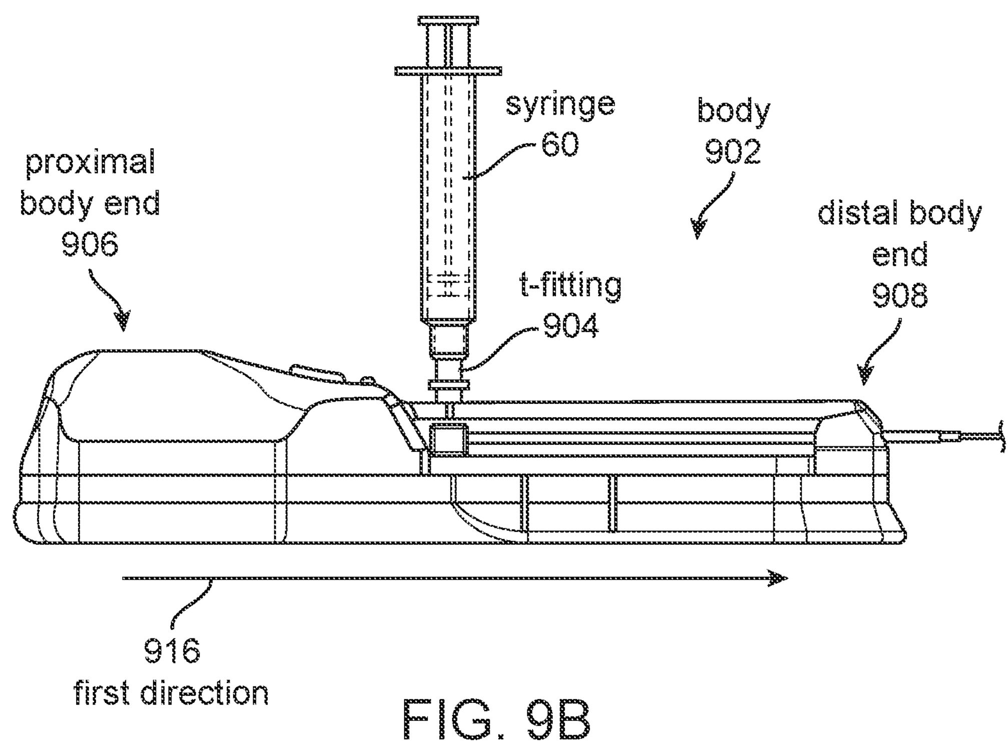
FIG. 9B illustrates a side view of the controller of FIG. 9A, according to some examples.
Figure 9C:
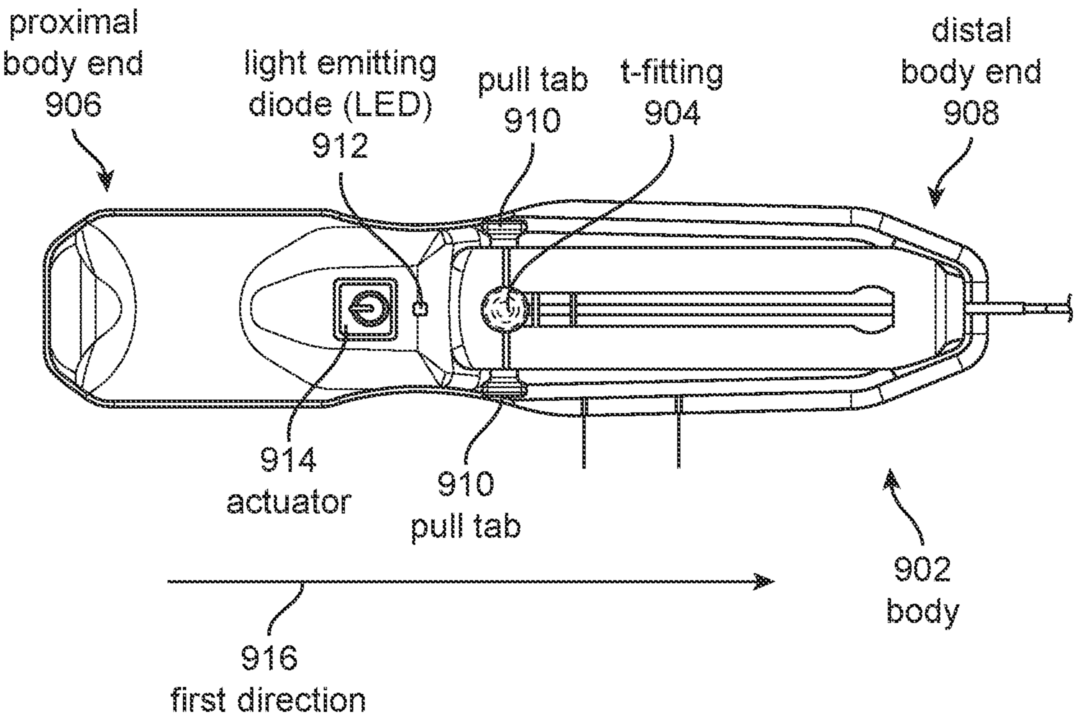
FIG. 9C illustrates a top view of the controller of FIG. 9A without a syringe, according to some examples.

Also included in FIGS. 9A, 9B, and 9C, (labeled in 9A and 9C) is a light emitting diode (LED) 912. The LED 912 may be used to convey an array of information to an operator. For example, the LED 912 may indicate that the device is receiving power or turned on. The LED 912 may indicate that the sheath 40 is fully retracted about the wire 30, indicating that the wire 30 is ready to be rotated in order to provide an abrasive treatment.

Throughout this disclosure, reference is made to segmental mechanical or mechanochemical ablation. The LED 912 may indicate treatment times to an operator in these or other instances. For example, perhaps the operator desires to provide a mechanical agitation of a treatment segment 55 for a set period of time prior to moving to a subsequent treatment segment 55. In these cases, the LED 912 may light up to indicate that the treatment time has passed, and it is time to move to the subsequent treatment segment 55. Or, perhaps, the LED 912 is constantly lit up, and the LED 912 turns off to indicate that this treatment time has passed.

In mechanochemical ablation, it is often desired to inject a drug, such as sclerosant at a specific rate. In these cases, the LED 912 may indicate, through lighting up or turning off, as the case may be, that the mechanical ablation has occurred for a desired amount of time, and it is time to begin injecting the drug into the treatment segment 55. Likewise, the LED 912 may indicate that the injection time has passed, and it is time to move the catheter 15 to a subsequent treatment segment 55.

While one LED 912 is shown in FIGS. 9A, 9B, and 9C, it is understood that multiple LEDs 912 may be present in the device, and could serve multiple different purposes. For example, while not explicitly labeled, FIG. 8 illustrates two LEDs on the body 802 proximal to the location of the syringe 60 and the T-fitting 804. These LEDs 912 may be labeled in order to prevent confusion for an operator.

Additionally, or alternatively, the controller 20 may include a display (such as the display 508 of FIGS. 5A, 5B, and 5C) or some kind of alarm, or other noise maker, for the purposes of indicating treatment times to an operator. In the case of an alarm or another noise maker, the operation would be similar to that of the LED 912—the alarm may sound to indicate the end of a mechanical ablation of a treatment segment 55, the end of an injection of a drug into the treatment segment 55, the time to move to a subsequent treatment segment 55, and/or the end of an overall treatment. The display may perform in much the same way while also indicating how much time is remaining in each of these steps.

Finally, also seen in FIGS. 9A, 9B, and 9C (only labeled in 9A and 9C) is an actuator 914. The actuator 914 may be any device capable of receiving input from an operator, such as a switch, a button, a lever, a touch screen, etc. The actuator 914 may serve one or multiple purposes, including but not limited to turning on and off the device and turning on and off a motor within the device. While one actuator 914 is shown in FIGS. 9A, 9B, and 9C, it is understood that multiple actuators 914 may be present on the device for different purposes, such as the actuators 506*a* and 506*b* of FIGS. 5A, 5B, and 5C.

Figure 10:
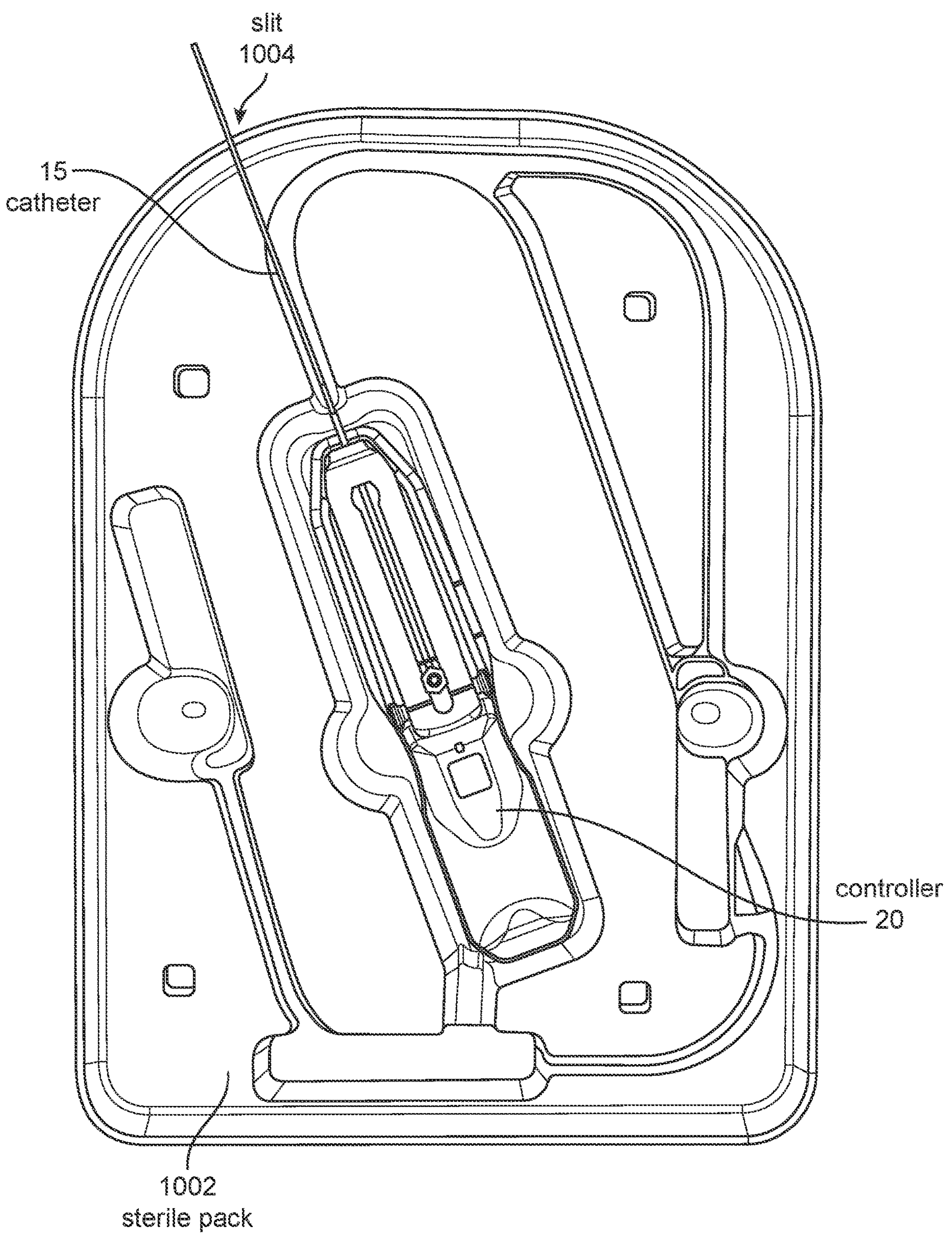
FIG. 10 illustrates a top view of a controller within a sterile pack, according to some examples.

FIG. 10 illustrates a top view of a device contained within a sterile pack 1002. It is understood that any controller 20, as shown and described in FIGS. 5A, 5B, 5C, 7, 8, 9A, 9B, and 9C, as well as other potential example controllers 20, may be operational in tandem with the disclosure of the sterile pack 1002. Likewise, it is understood that any combination of catheter 15, wire 30, and sheath 40, as shown and described in FIGS. 12A, 12B, 12C, 14, 15, 16, 17, 18, 19, 20, 21, 22A, 22B, 22C, 23A, 24A, and 25A, as well as other potential example wires 30, may be operational in tandem with the disclosure of the sterile pack 1002.

As seen in FIG. 10, a controller 20 may fit within a cavity, or recess, of the sterile pack 1002. Spaces are provided within the sterile pack 1002 for the catheter 15 to reside as well, but FIG. 10 is illustrating how the device may appear when in use rather than when in storage. A slit 1004 may be provided in the sterile pack 1002, through which the catheter 15 may fit. This may permit the controller 20 to be operated from within the sterile pack 1002 while the catheter 15 exits the sterile pack 1002 for insertion into the body of a patient.

While the component "slit 1004" is used throughout this disclosure, it is understood that any other equivalent vacancy in the sterile pack 1002, such as a channel or an opening may be used.

In some examples, the catheter 15 may be removable from the controller 20 to be placed through this slit 1004. In other examples, the slit 1004 slidably receives the catheter 15 while the catheter 15 is already coupled to the controller 20. In either case, the controller 20 may be operated from within the sterile pack 1002, permitting operators to perform a treatment while not necessitating a sterile drape.

In examples where the catheter 15 is not detachably coupled to the controller 20, the entire ablation system 10 may need to be sterilized in between treatments. However, in examples where the catheter 15 is detachably coupled to the controller 20, the catheter 15 may be sterilized separately without needing to sterilize the controller 20 in between treatments. By permitting the controller 20 to be reused, this may help to cut down on waste.

Additionally, the catheter 15 may be made to be disposable (this could mean the sheath 40 and/or the wire 30 are disposable in cases where the catheter 15 includes a sheath 40 and a wire 30). This may greatly cut down on costs and waste generation, as the controller 20 may be reused between treatments, and the catheter 15 may be thrown away after use. Additionally, the operator may not need to sterile drape, and the surface on which the controller 20 in the sterile pack 1002 is placed may not need to be fully sterilized (it could be simply wiped down), as the controller 20 would not make direct contact with these surfaces.

In any example where the catheter 15 is detachably coupled to the controller 20, the controller 20 may be packaged by itself within the sterile pack 1002, permitting the controller 20 to be sold separately from the catheter 15.

Additionally, whether or not the catheter 15 is detachably coupled to the controller 20, the sterile pack 1002 may be "chip-clipped" along a wall for quick and easy access. This would permit operators to gain quick access to the controller 20 without the need to sift through storage or cardboard boxes of devices and catheters in order to find the device that they need.

Figure 11:
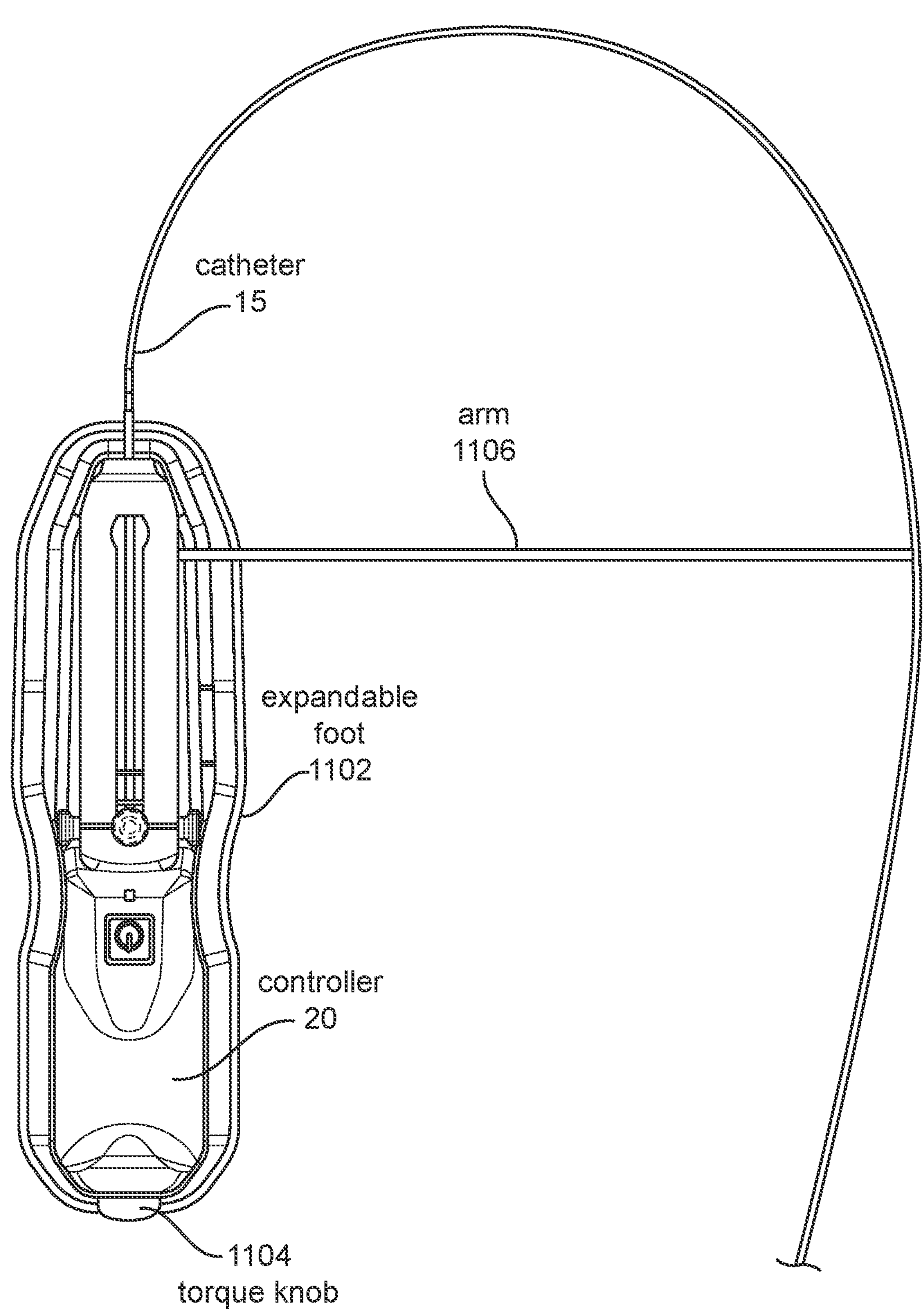
FIG. 11 illustrates a controller including additional features, according to some examples.

FIG. 11 illustrates a top view of an example ablation system 10. As seen in FIG. 11, the controller 20 may include an expandable foot 1102. This expandable foot 1102 may be webbed or otherwise constructed in order to permit an operator to control how wide the expandable foot 1102 is with regard to the base of the controller 20. Through expanding the expandable foot 1102, the controller 20 may be provided additional stability, preventing the controller 20 from tipping on its side due to an external force.

It is understood that the expandable foot 1102 as shown in FIG. 11 may be used in combination with any of the various controller 20 examples as shown and described previously in FIGS. 5A, 5B, 5C, 7, 8, 9A, 9B, and 9C as well as any additional controller not specifically illustrated herein.

This may prove particularly useful in examples where the motor is located under the T-fitting/saddle location, causing the controller 20 to be shorter in length but taller in height. This shorter length and taller height footprint may cause the controller 20 to have a higher center of gravity, making it more prone to tipping over, but the expandable foot 1102 may prevent this from happening. In such cases where the motor is located under the T-fitting/saddle location, gears could be used to create a gear ratio such that the rotation of the catheter 15 and/or wire 30 is controllable to be a desired rotation speed.

Also shown in FIG. 11 is a torque knob 1104. The torque knob 1104 may permit an operator to provide torque to the catheter 15 and/or the wire 30, thereby adjusting the direction of traverse of a distal end of the catheter 15 and/or the wire 30. This is similar to the slot in the saddle 704 of FIG. 7. However, instead of needing to rotate the syringe 60 about the body 702 as shown and described in FIG. 7, the torque knob 1104 may provide an easy method of controlling these distal ends of the catheter 15 and/or the wire 30 without adjusting the syringe 60 at all. Again, this newly created torque may permit the operator to make fine movements of the distal end of the catheter 15 and/or wire 30 in the treatment site 50 in order to make better abrasive contact with the vessel walls, and/or facilitate traversal of the torturous vasculature of the patient. Such a torque knob 1104 may work in conjunction with the controller as described through the use of a dual-shafted motor, or the example where the motor is beneath the T-fitting/saddle.

It is understood that the torque knob 1104 as shown in FIG. 11 may be used in combination with any of the various controller 20 examples as shown and described previously, in FIGS. 5A, 5B, 5C, 7, 8, 9A, 9B, and 9C, as well as any additional controller not specifically illustrated herein.

Finally, as shown in FIG. 11, the controller 20 may include an arm 1106. In examples where the controller 20 is positioned such that the catheter 15 and/or the wire 30 turns back upon itself prior to being inserted into a patient, the arm 1106 may facilitate the prevention of the catheter 15 and/or the wire 30 acquiring a kink, which may prove detrimental to any fluid delivery, such as that of a drug. The arm 1106 may further set a radius that the catheter 15 is kept away from the controller 20. Additionally, or alternatively, the arm 1106 may act as a catheter clamp, keeping the catheter 15 in place during a treatment. The arm 1106 may further prevent the device from being run while in an aggressive radius, which may have negative effects on the performance of the device. The arm 1106 may also prevent the ablation system 10 from becoming twisted (i.e., while the motor is running, the ablation system 10 may twist on itself, and the arm 1106 may prevent this).

It is understood that the arm 1106 as shown in FIG. 11 may be used in combination with any of the various controller 20 examples as shown and described previously in FIGS. 5A, 5B, 5C, 7, 8, 9A, 9B, and 9C, as well as any additional controller not specifically illustrated herein.

Figure 12A:
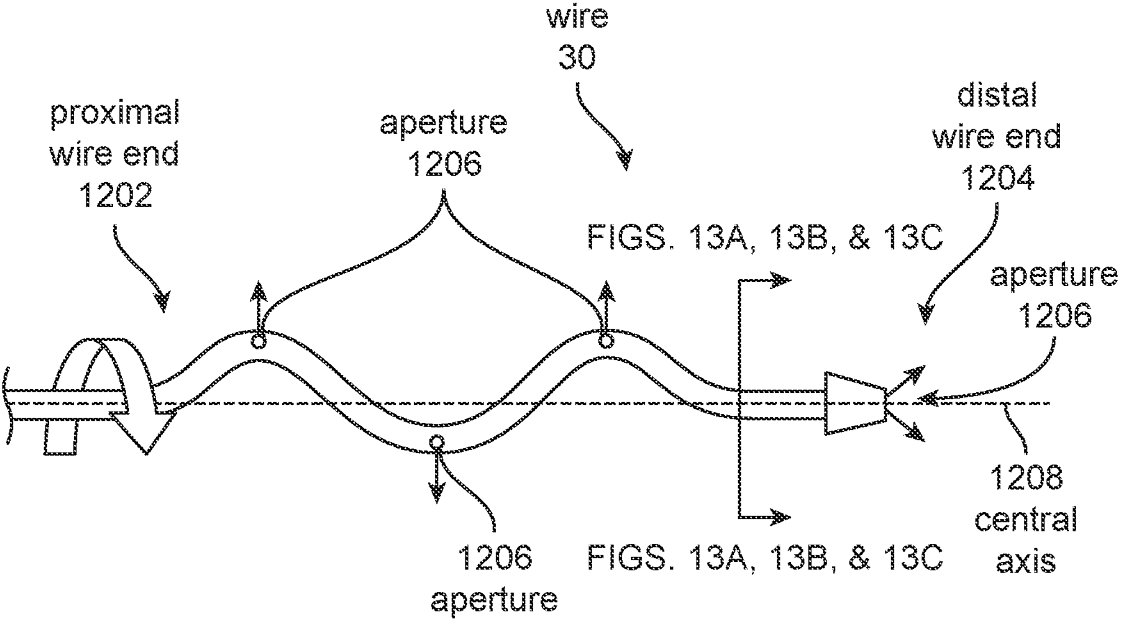
FIGS. 12A, 12B, and 12C illustrate side views of example wires.
Figure 12B:
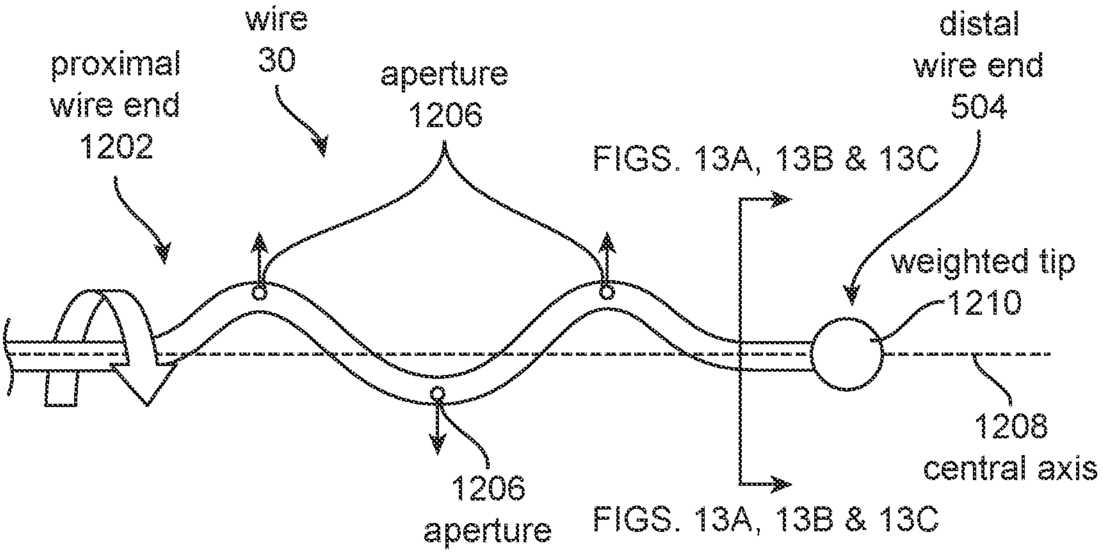
Figure 12C:
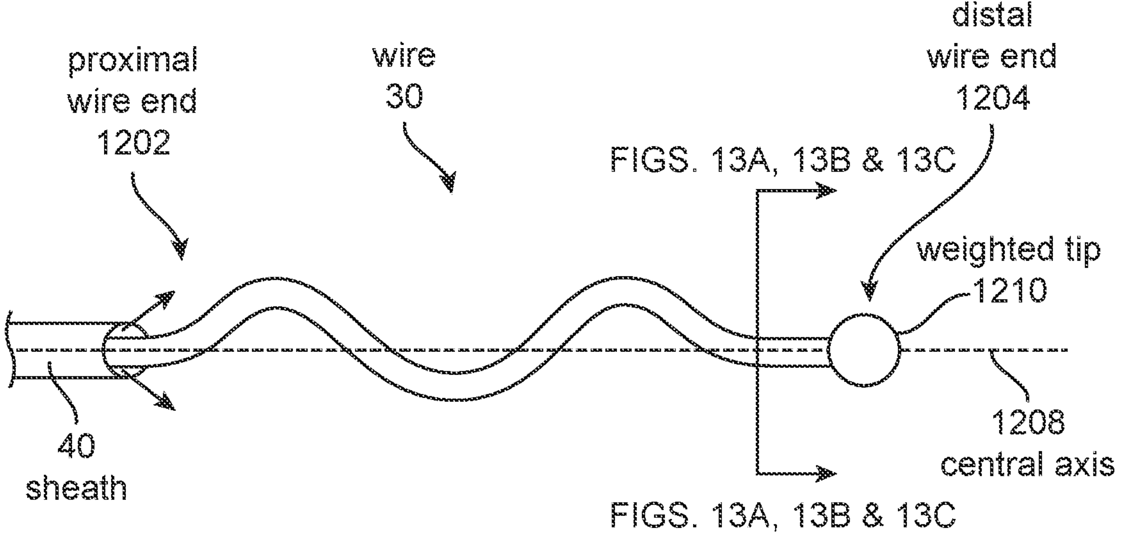

FIGS. 12A, 12B, and 12C illustrate example side views of a wire 30. Specifically, FIGS. 12A, 12B, and 12C illustrate different examples of components for releasing a drug, such as sclerosant, in an ablation system 10 featuring a wire 30. The wire 30 may include a proximal wire end 1202, and a distal wire end 1204 opposite the proximal wire end 1202. The proximal wire end 1202 points generally to an area proximal any feature of the distal wire end 1204. Because FIGS. 12A, 12B, and 12C (as well as FIGS. 14, 15, 16, 17, 18, 19, 20, 21, 22A, 22B, 22C, 23A, 24A, and 25A as shown and described below) only show a distalmost portion of the wire, it is not possible to show the proximal wire end 1202 at the location where it begins near any present controller 20. For this reason, throughout this disclosure, the proximal wire end 1202 is understood to refer to the wire 30 proximal to the portion of the wire intended to abrade (or ablate, or agitate) the vessel walls.

As shown in FIGS. 12A, 12B, and 12C, the wire 30 may include a sinusoidal shape. This sinusoidal shape permits the wire 30 to make contact with the walls of a vessel into which the wire 30 has been inserted. In some examples, the wire 30 is made from Nitinol (such as Nitinol #1 ASTM F2063) or a similar material that may return to its shape after compression, such as the compression the wire 30 may experience when stored within the sheath 40.

Any of the examples described and shown herein are also operational within a stent. In such examples, the wire 30 would make contact with both the stent and the tissue. Additionally, many of the examples shown and described in the present disclosure include either three or four peaks. It is understood that the number of peaks present in the figures and described in the disclosure is for example only, and any number of peaks in a sinusoidally shaped wire may be present as desired, and a greater number of peaks could mean a greater treatment segment 55 length, or simply a greater number of contact points along such a treatment segment 55.

Additionally, any dimensions regarding the spacing or amplitude of the wire 30 are also by example only, and it is understood that different size wires may prove useful for different-sized vasculature or treatment segments 55. For example, the wire 30 may have an amplitude of approximately 12 millimeters. In this example, because the wire 30 is at least partially compressible, the wire 30 is operable in vasculature that has a smaller diameter than the amplitude of the wire 30. In such an example wire 30 having an amplitude of approximately 12 millimeters, the working range, or range of vessel diameters, the wire 30 may be capable of treating would be from about 4 millimeters to about 12 millimeters.

In instances where the diameter of the vessel being treated is smaller than the amplitude of the wire 30, the wire 30 will be under compression, causing the peaks of the sinusoidal shape to stretch out, lengthening the contact made with the vessel walls and, in turn, effectively increasing the length of the treatment segment 55. The wire 30 could treat larger diameter vessels as well in this example, but it would be unable to make continuous contact with the vessel walls. Thus, a larger amplitude wire 30 may be desired for such an application.

In a procedure such as sclerotherapy, it may be desirable to either damage or penetrate the intima of a vessel, and to only damage the media of the vessel. Traditional wires in the prior art make contact with the vessel wall at the distal tip, resulting in this point of contact being abrupt and sharp. This comes with the possible issue of penetrating the media in addition to the intima, which may cause the wire to enter the surrounding adventitia. The solutions to this problem currently include rotating the wire in the reverse direction with the hope that the wire will untangle itself from the vessel to the point where the wire may be safely removed. Another solution includes pulling, often quite hard, on the wire to forcefully remove the wire from the patient. This solution may cause pain or discomfort for the patient, or could even result in stripping the vein entirely.

With a sinusoidal shape, such as that of the examples in FIGS. 12A, 12B, and 12C, the point of contact is much blunter, or more obtuse, than traditional wires 30. This makes the likelihood of penetrating the media and entering the adventitia much less likely, and thus increases the safety and efficacy of sclerotherapy procedures.

An additional issue with current sclerotherapy treatments is the multitude of functions the operator must keep track of simultaneously. For example, in many prior art devices, a treatment may include pulling the wire back through the vessel that is being treated at a rate of about 1 to 2 millimeters per second. At the same time, the operator must be injecting a drug, such as sclerosant, from a manually operated syringe at a rate of about 0.1 to 0.2 milliliters per centimeter. Already, the operator must have one eye on two separate gauges of measurement—the distance wire is being withdrawn, and the distance a plunger of the syringe has been depressed. Because the retraction rate of the catheter is time-dependent, the operator must also keep track of the time passing in some way—often by counting mentally, which is both prone to error, as well as another item that may distract the operator from the procedure. Treatments are often close to 40 centimeters long, which means that these treatments can take anywhere from 200 to 400 seconds based on the parameters suggested above.

In many prior art devices, the distal tip of the wire is the only point of contact between the wire and the vessel wall. Thus there is no "treatment segment" involved in these prior art devices as described in the current specification. This is the root cause for procedures to necessitate an operator to withdraw the wire at a specific rate while a drug is injected at a separate, distinct, and specific rate. The present disclosure seeks to remedy this deficiency of the prior art by eliminating the need to withdraw the catheter while injecting the drug at the same time.

Through the use of a sinusoidal-shaped wire 30 (or other wire shaped and configured to contact a length of a vessel wall), which treats a length of the vein at once, methods may be constructed for segmental treatment, rather than continuous treatment. In these methods, the wire 30 is provided to the distal-most portion of the treatment site 50 and then activated for a predetermined amount of time. With the present invention, the operator only needs to worry about the quantity of the drug being injected, which, because it is no longer dependent on the distance the wire 30 has been retracted, can be much more variable without causing adverse effects. Once a prescribed amount of the drug has been delivered to the treatment segment 55, the operator may then withdraw the catheter 15 to a subsequent treatment segment 55, either at a specified rate or at any rate the operator desires, while not having to inject any more of the drug until the catheter 15 has reached this subsequent treatment segment 55.

The display 508 as described in FIGS. 5A and 5B can also take an additional burden off of the operator as they would no longer need to mentally count the time. Similarly, the LED 912 as described in FIGS. 9A and 9C may serve a similar purpose. Any such indicator, be it the display 508, the LED 912, or some other method of providing information to an operator, such as via noise from an alarm, can permit the operator to no longer keep track of the passage of time themselves, allowing them to give their full attention to smaller details of the procedure.

In some examples, the syringe may even be replaced by an Archimedes screw to deliver a set amount of drug per rotation of the wire 30. Additional features may include a torque limiter, which may indicate if the wire 30 is rotating through an unintended medium, such as if the wire 30 has penetrated into the adventitia. A clutch may also be included. Should some parameter such as the torque pass a certain threshold, the clutch may automatically stop the wire 30 from rotating. If the wire 30 has penetrated into the adventitia, this automatic stoppage of the rotation of the wire 30 may help to prevent the vessel from tangling upon itself.

FIG. 12A illustrates a wire 30 having at least one aperture 1206. As shown in FIG. 12A, the wire 30 may be a hypotube having multiple apertures 1206 along the length of its body, as well as a nozzle-type tip at the distal wire end 1204 which includes an additional aperture 1206. The apertures 1206 are present to deliver a drug, such as sclerosant, to a treatment site 50 during a procedure. An arrow is present at the proximal wire end 1202 to show the rotation of the wire 30 during a procedure. The wire 30 may rotate in either direction during a procedure, and this rotation permits the peaks of the sinusoidal shape to make full peripheral contact with the vessel walls, improving abrasion during the procedure. In some examples, but not all examples, the wire 30 only rotates in a single direction. Also shown is a central axis 1208, about which the wire 30 rotates.

FIG. 12B illustrates a wire 30 having at least one aperture 1206, similar to those shown in FIG. 12A. However, dissimilar to the example of FIG. 12A, FIG. 12B includes a weighted tip 1210 at the distal wire end 1204. An arrow shows a possible direction of rotation about a central axis 1208, but the inclusion of a weighted tip 1210 creates a gyroscopic effect, which can facilitate keeping the wire 30 centered within the vessel, ensuring consistent contact with the walls of the vessel.

FIG. 12C illustrates a wire 30 with a weighted tip 1210, but no apertures 1206 are present in this example. The sheath 40 is shown and acts as a fluid lumen while the wire 30 is exposed. In this example, a drug, such as sclerosant, may be delivered to the treatment site 50 through the sheath, and contact the vessel walls proximal to the rotation of the wire 30 along the length of treatment.

Figure 13A:
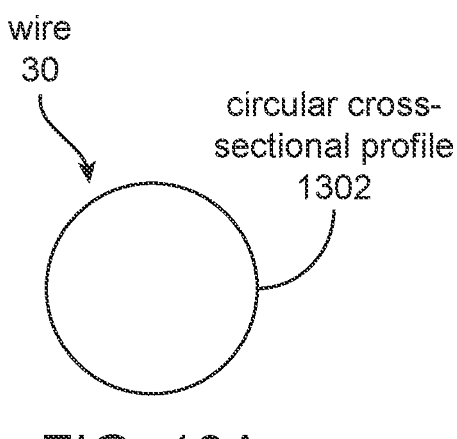
FIGS. 13A, 13B, and 13C illustrate example cross-sectional views of a wire.
Figure 13B:
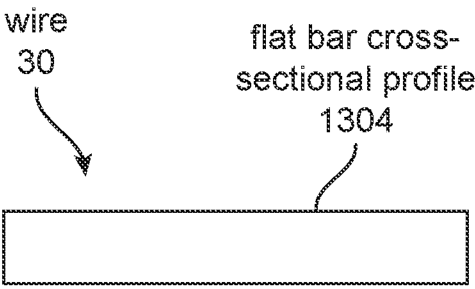
Figure 13C:
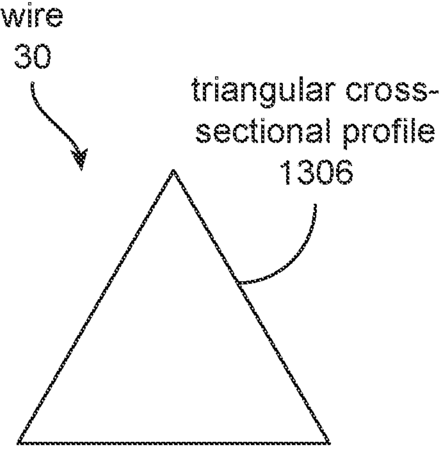

FIGS. 13A, 13B, and 13C illustrate a few possible cross-sectional profiles of a wire 30. Specifically, FIG. 13A illustrates a circular cross-sectional profile 1302 of a wire 30, FIG. 13B illustrates a rectangular, or flat bar cross-sectional profile 1304 of a wire 30, and FIG. 13C illustrates a triangular cross-sectional profile 1306 of a wire 30.

It is understood that the various cross-sectional profiles as shown in FIGS. 13A, 13B, and 13C may be used in combination with any of the various wire 30 examples as shown and described previously in FIGS. 12A, 12B, 12C, as well as in combination with any of the various wire 30 examples as will be shown and described in FIGS. 14, 15, 16, 17, 18, 19, 20, 21, 22A, 22B, 22C, 23A, 24A, and 25A, or any additional wire not specifically illustrated herein.

A circular cross-sectional profile 1302, as shown in FIG. 13A, is the most traditional shape for a wire. Its rounded profile may cause damage, but the lack of sharp edges reduces the likelihood of penetration through the media and into the adventitia. If greater abrasion is desired, the circular cross-sectional profile 1302 may have an applied surface roughness.

The flat bar cross-sectional profile 1304 of FIG. 13B and triangular cross-sectional profile 1306 of FIG. 13C have sharper edges than the circular cross-sectional profile 1302 of FIG. 13A. These sharp edges may abrade vessel walls more quickly than the circular cross-sectional profile 1302 can, but with an increased chance of penetrating the media, rather than just damaging it.

Figure 14:
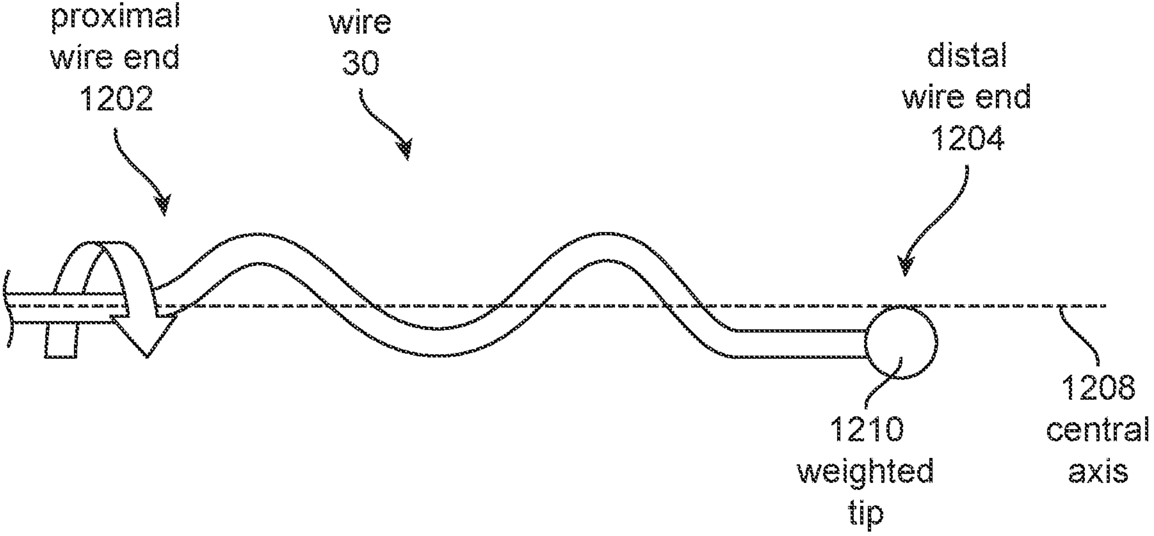
FIG. 14 illustrates a side view of an example off-axis wire.

FIG. 14 illustrates a side view of an example wire 30 that terminates at a point that does not fall along the central axis 1208. A weighted tip 1210 is included in this example, and, because of the off-axis location of the weighted tip 1210, the opposite of, or at least an opposing effect to, a gyroscopic effect is achieved. The weighted tip 1210 causes the wire 30 to rotate more erratically, causing the peaks of the sinusoidal shaped wire 30, as well as the weighted tip 1210, to make harsher, if less frequent, contact with the vessel walls. In some examples, no weighted tip 1210 is included, but the wire 30 still terminates off-axis from the central axis 1208.

Figure 15:
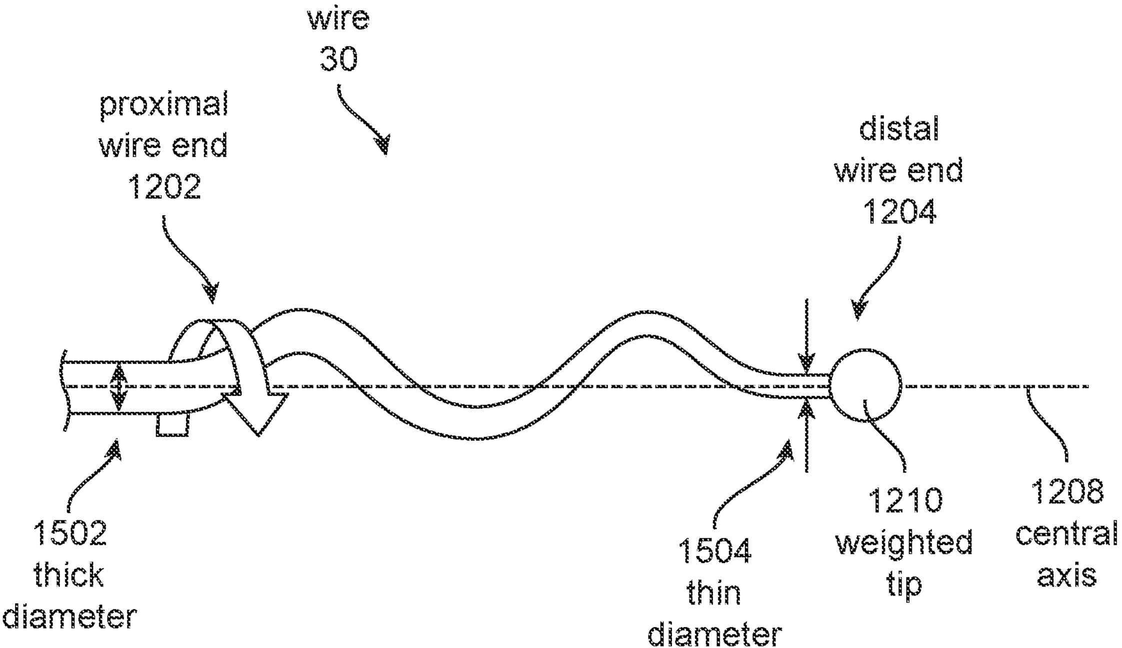
FIG. 15 illustrates a side view of a varying thickness wire, according to some examples.

FIG. 15 illustrates a side view of a wire 30 having a variable thickness. In the example shown, the proximal wire end 1202 has a thick diameter 1502, and the distal wire end 1204 has a thin diameter 1504. The thick diameter 1502 is greater than the thin diameter 1504. The thick diameter 1502 portion of the wire 30, because of its thickness, may be more rigid than the thin diameter 1504 portion of the wire 30. This can allow the thick diameter 1502 portion of the wire 30 to "kick" off of the vessel walls, causing the thin diameter 1504 portion of the wire 30 to make increased contact with the vessel walls. The thick diameter 1502 portion of the wire 30 may also permit increased surface roughness to be applied, which can improve the abrasion abilities of the wire 30. Additionally, because of the greater profile size of a thick diameter 1502 portion of the wire 30, better contact with the vessel walls can be made.

While FIG. 15 shows the thick diameter 1502 at the proximal wire end 1202 and the thin diameter 1504 at the distal wire end 1204, these positions are exemplary only. Any portion of the wire 30 may include a thick diameter 1502 or a thin diameter 1504 based on the needs of the user, and thus different effects may be achieved.

Figure 16:
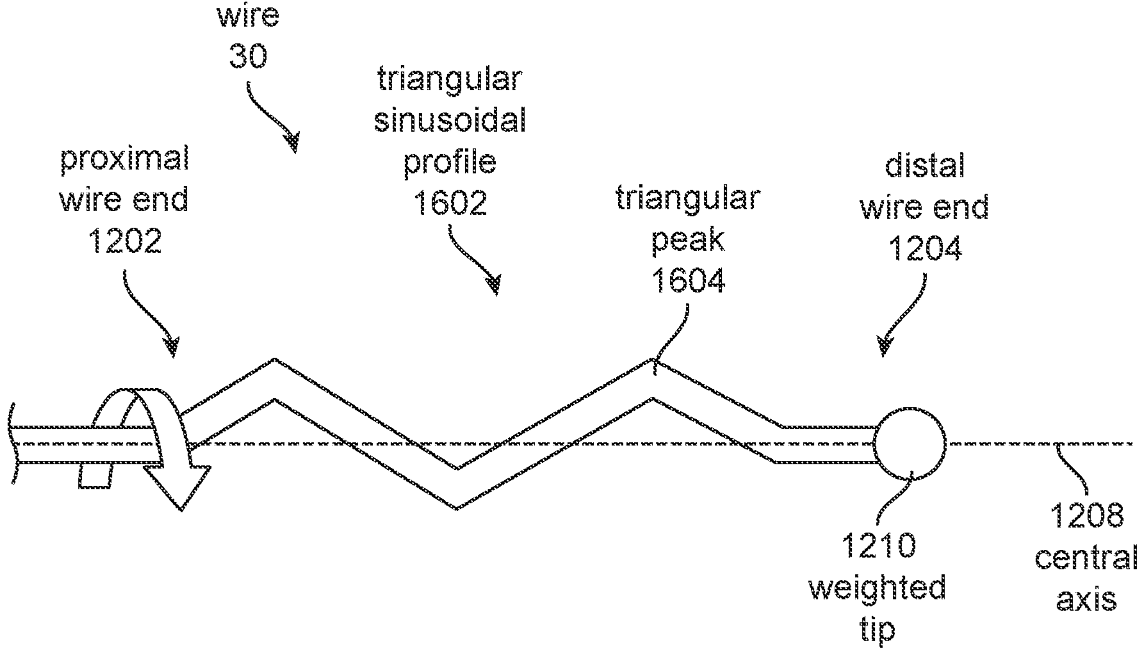
FIG. 16 illustrates a side view of an example wire having an angular profile.

FIG. 16 illustrates a side view of an additional example wire 30 forming a triangular sinusoidal profile 1602. In fact, any type of shaped sine wave may be used as desired by the user. A triangular sinusoidal profile 1602 creates sharper points of contact with the vessel walls (as seen in FIG. 2), which may improve the abrasion against these sections. These sharper points, or triangular peaks 1604, may scratch or cut into the intima and/or media, thus further damaging the vessel wall than simple abrasion might.

Figure 17:
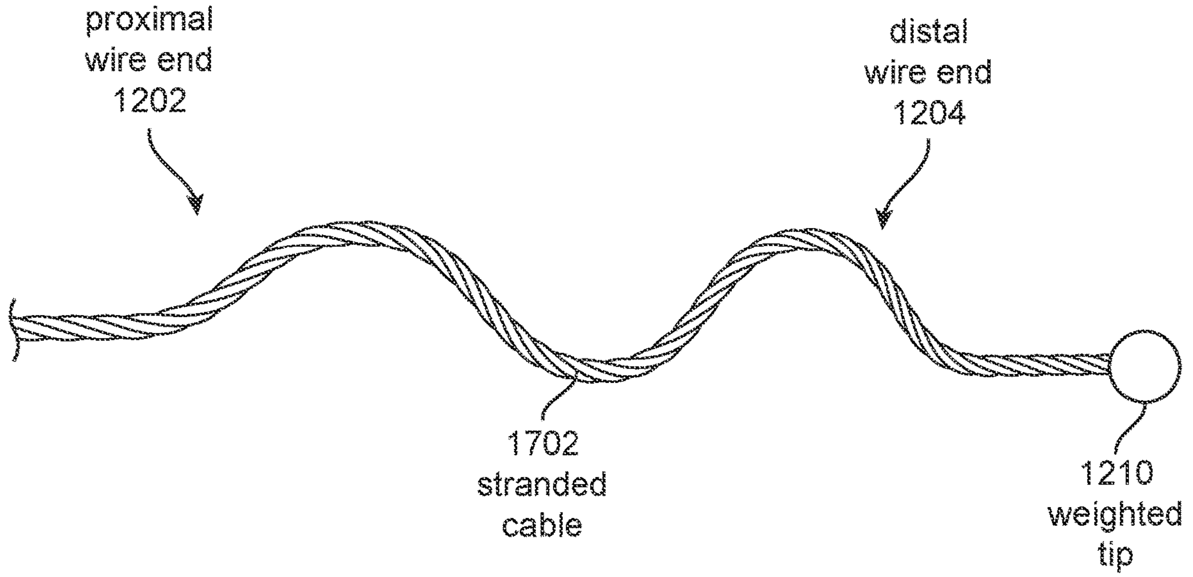
FIG. 17 illustrates a side view of a wire including a stranded cable construction, according to some examples.

FIG. 17 illustrates a side view of an example wire 30, including a stranded cable 1702 construction. The surface of the stranded cable 1702 may be rougher than that of a monofilament wire or cable because of the increased number of ridges about the perimeter. This increased roughness may permit the stranded cable 1702 to make more aggressive contact with the walls of a vessel within a treatment site 50. Additionally, the strands of the stranded cable 1702 may be loosened or tightened, permitting the operator to "dial in" or set the radius desired for a treatment. For example, a looser stranded cable 1702 would have a greater radius, and thus the overall wire 30 diameter would increase. Contra, a tighter stranded cable 1702 would have a smaller radius, thus decreasing the diameter of the overall wire 30.

Figure 18:
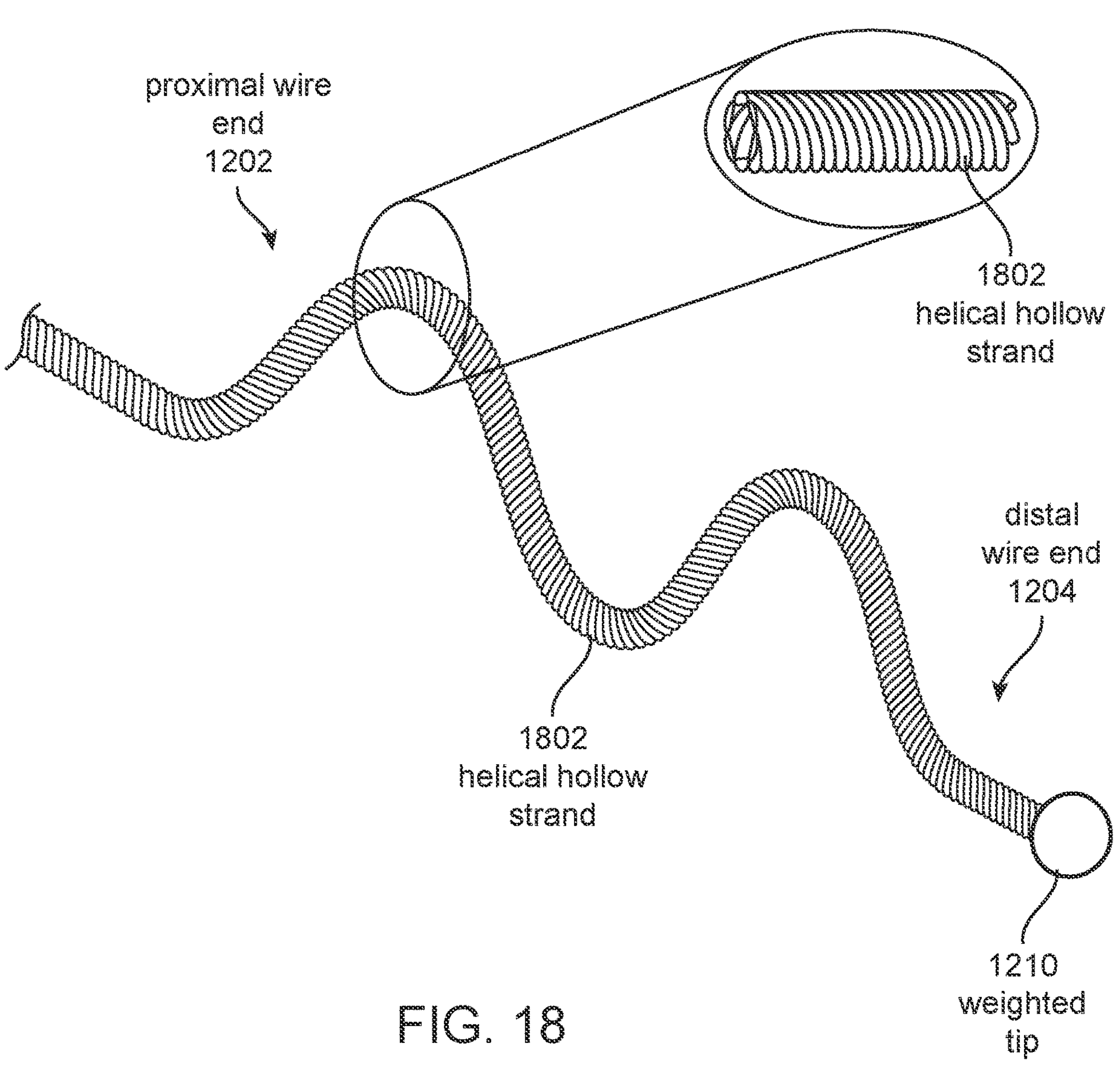
FIG. 18 illustrates a perspective and inset view of an example wire including a helical hollow strand construction.

FIG. 18 illustrates a side view of an example wire 30, including a helical hollow strand 1802 construction. Similar to the stranded cable 1702 of FIG. 17, the helical hollow strand 1802 may be rougher than that of a monofilament wire or cable because of the increased number of ridges about the perimeter. Once again, this increased roughness may permit the helical hollow strand 1802 to make more aggressive contact with the walls of a vessel within a treatment site 50. The helical nature of the helical hollow strand 1802 makes it a candidate for a type of wire 50 that includes a lumen, perhaps for delivering a drug.

Additionally, or alternatively, while not shown in FIG. 18, a pull string could be threaded through the hollow portion of the helical hollow strand 1802 and pulled such that the helical hollow strand 1802 forms a differently shaped profile, such as a sinusoidal-shaped profile. In addition to allowing the helical hollow strand 1802 to be delivered to a treatment site 50 in a lower profile (maybe even completely straightened out), such a pull string may allow the peak-to-peak distance or peak amplitude of a sinusoidal profile helical hollow strand 1802. This may prove useful in situations where the peak size or peak-to-peak distance can be optimized for a specific treatment segment 55.

In addition, a drug delivered through the hollow portion of the helical hollow strand 1802 may not need to be delivered to the distalmost end of the helical hollow strand 1802. Instead, the drug may be delivered as a weeping agent through the individual coils.

Finally, while also not specifically illustrated in FIG. 18, there could be a second helical hollow strand 1802 wrapped around the first helical hollow strand 1802—with the coils either perpetuating in the same direction or contrasting with one another. In such an example, an oscillating motion may be formed by the helical hollow strands 1802 without necessitating the opening of the coils.

Figure 19:
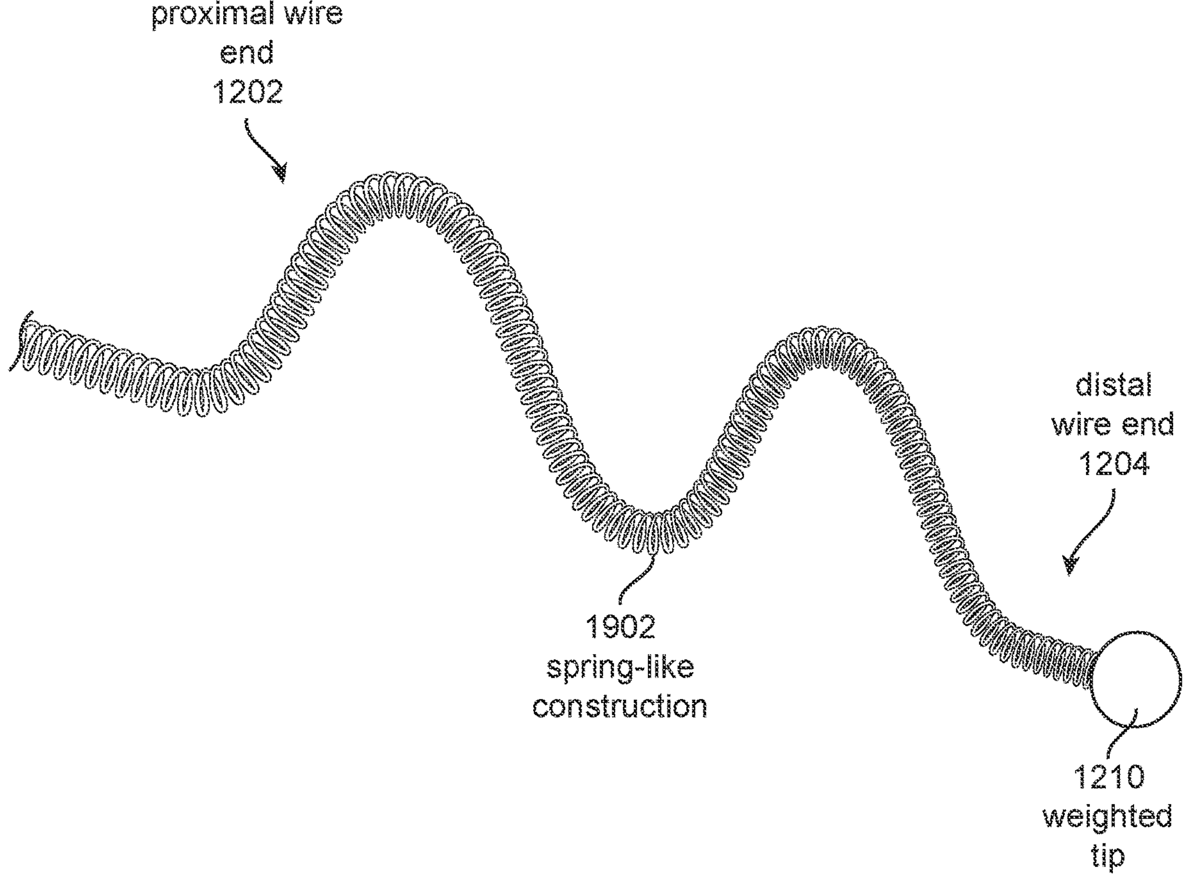
FIG. 19 illustrates a perspective view of an example wire including a spring-like construction.

FIG. 19 illustrates a side view of an example wire 30 including a spring-like construction 1902. In a straightened form, the spring-like construction 1902 may appear as a three-dimensional sinusoid, or helix. However, the spring-like construction 1902 is not limited to this, as is shown in FIG. 19, and said spring-like construction 1902 may itself form a sinusoidally shaped profile. The benefits of this are similar to those discussed in the stranded cable 1702 of FIG. 17 and the helical hollow strand 1802 of FIG. 18 in that the spring-like construction 1902 includes further ridges about the wire 30 perimeter, which may increase the roughness of the wire 30. Once again, this increased roughness may permit the spring-like construction 1902 to make more aggressive contact with the wall of the vessel in the treatment segment 55.

Figure 20:
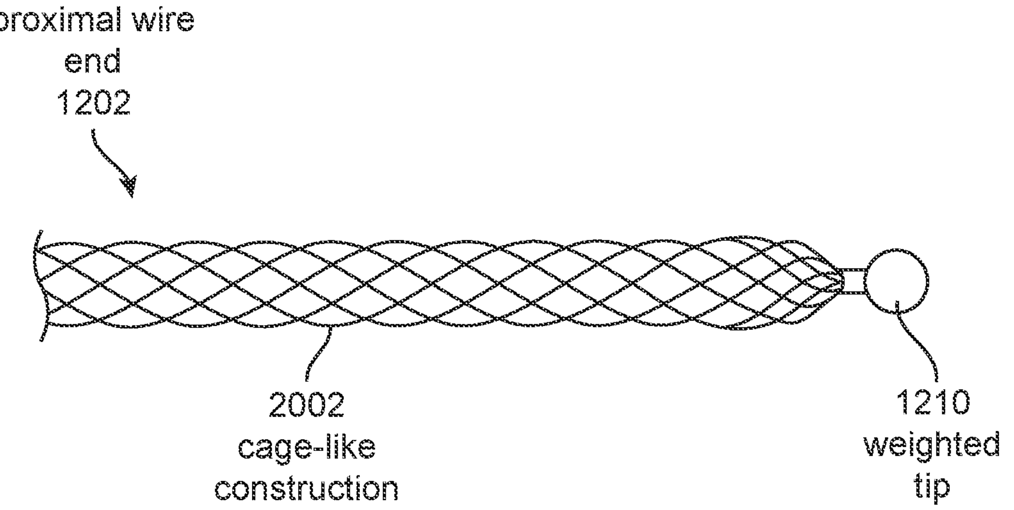
FIG. 20 illustrates a side view of a wire including a cage-like construction, according to some examples.

FIG. 20 illustrates a side view of an example wire 30, including a cage-like construction 2002. The cage-like construction 2002 includes multiple individual components, such as strands of wire, helically winding about one another, similar to the stranded cable 1702 of FIG. 17 and the helical hollow strand 1802 of FIG. 18. However, in the cage-like construction 2002, the individual strands may include gaps, or spaces, between one another. The individual strands of the cage-like construction 2002 may permit the wire 30 to make contact with the wall of a vessel in a treatment segment 55 multiple times per rotation, thus increasing the abrasive properties of the wire 30. While not shown in FIG. 20, the cage-like construction could also be modified in the shape of its profile, such as a sinusoidally shaped profile, if desired. The cage-like construction 2002 will be revisited as a concept as both a proximal feature 2602 in FIG. 26C as well as a distal feature 2702 in FIG. 27B.

Figure 21:
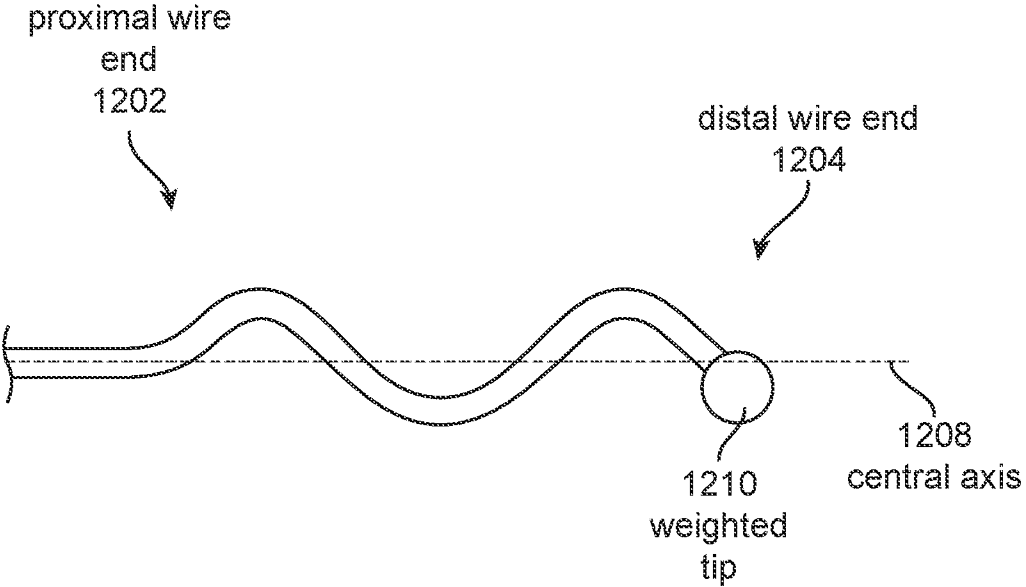
FIG. 21 illustrates a side view of an additional wire terminating off-axis, according to some examples.

FIG. 21 illustrates a side view of an example wire 30 that terminates at a point that does not fall along the central axis 1208, similar to that of FIG. 14. Also similar to FIG. 14, the wire 30 of FIG. 21 may include a weighted tip 1210, and because of the off-axis termination point of this weighted tip 1210, an opposing effect to a gyroscopic effect is caused. The weighted tip 1210 may cause the wire 30 to rotate more erratically, causing the peaks of the sinusoidal-shaped wire 30, as well as the weighted tip 1210, to make more aggressive contact with the vessel walls. In some examples, no weighted tip 1210 is included, but the wire 30 still terminates off-axis from the central axis 1208.

Dissimilar to the example of FIG. 14, the wire 30 of FIG. 21 continues the path of the sinusoidal profile of the wire 30. Advantages in this example may include a less erratic path of the distalmost tip of the wire 30 than the example of FIG. 14. Additionally, fewer bends in the wire 30 are required to construct the example in FIG. 21, which may cut down on manufacturing costs. The weighted tip 1210 is shown to terminate at a point such that it is even with one of the peaks of the sinusoidal profile of the wire 30. This is not strictly necessary, and the termination point of the weighted tip 1210 may be positioned as desired by the user (though a termination point along the central axis 1208 may cause the gyroscopic effect to be employed again).

Figure 22A:
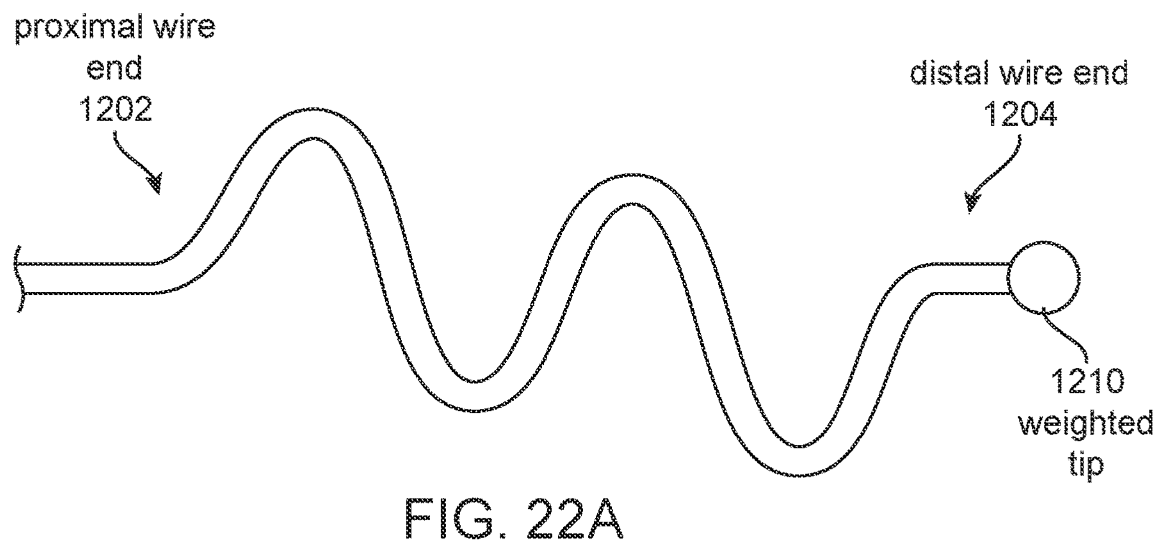
FIGS. 22A, 22B, and 22C illustrate various examples of wires including non-uniform amplitude profiles.
Figure 22B:
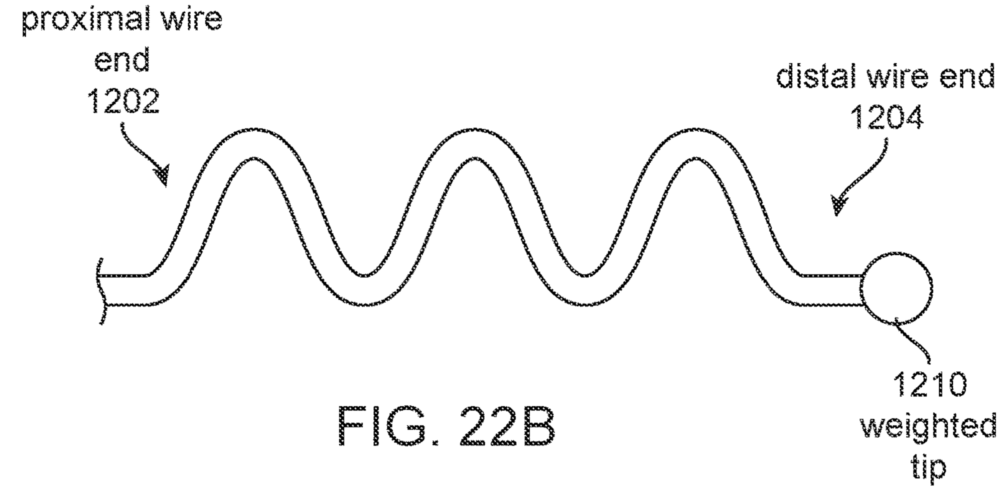
Figure 22C:
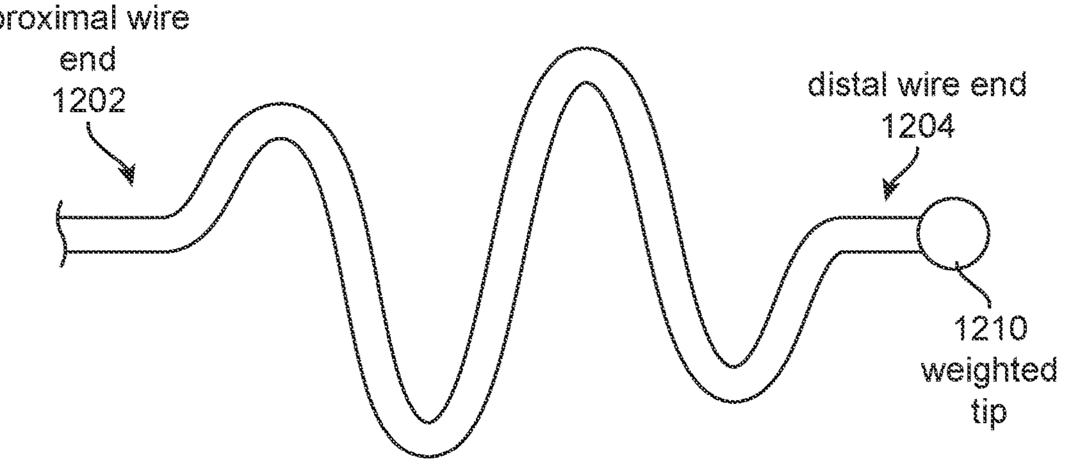

FIGS. 22A, 22B, and 22C illustrate various side views of example non-uniform amplitude wires 30. Specifically, FIG. 22A shows an example wire 30 having a first peak and a fourth peak that are greater in amplitude than the second peak and the third peak. FIG. 22B illustrates an example wire 30 having three peaks on one side of the central axis 1208 (not shown in this figure). FIG. 22C shows an example wire 30 having a first peak and a fourth peak that are smaller in amplitude than the second peak and the third peak. FIGS. 22A, 22B, and 22C are examples only and non-exhaustive—any formation of non-uniform amplitude wire 30 as desired may be used.

It is understood that any of the example non-uniform amplitude wires 30 as shown and described in FIGS. 22A, 22B, and 22C may be used in combination with any of the various wire 30 examples as shown and described previously in FIGS. 12A, 12B, 12C, 14, 15, 16, 17, 18, 19, 20, 21, 22A, 22B, 22C, 23A, 24A, and 25A, or any additional wire not specifically illustrated herein.

The benefits of such non-uniform amplitude wires include drug dispersion effects and treatment segment abrasion effects. For example, the wire 30 of FIG. 22A may cause a spraying effect of a drug in the middle section due to the lower amplitude peaks there. Contrastingly, the example wire 30 of FIG. 22C may cause the spraying effect to be away from the middle section, due to the higher amplitude peaks located there. Additionally, the one-sided peaks as displayed in FIG. 22B may cause a different course of abrasion due to the damage occurring along one side of the vessel all at once, rather than being dispersed about the perimeter.

Figure 23A:
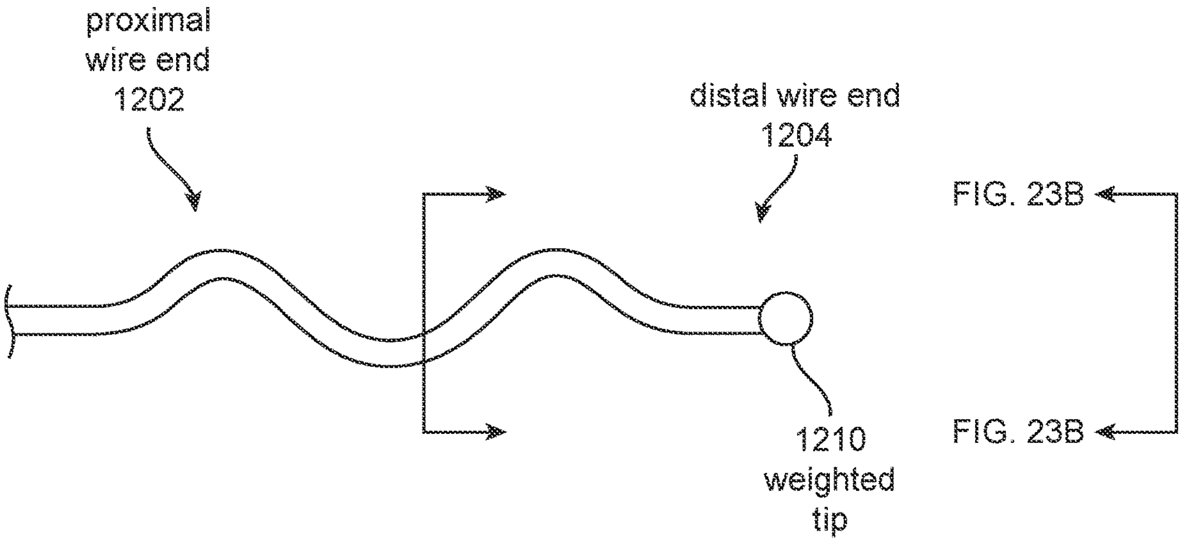
FIG. 23A illustrates an example wire including a sinusoidal profile.
Figure 23B:
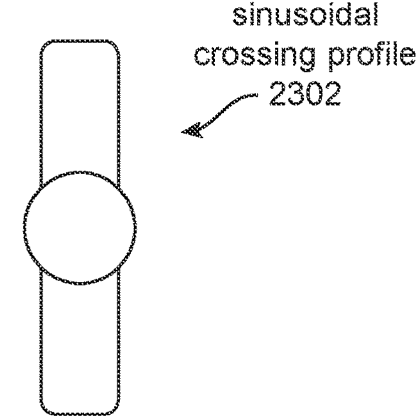
FIG. 23B illustrates a front view of the wire of FIG. 23A, according to some examples.

FIG. 23A illustrates an example wire 30 having a sinusoidal profile in two dimensions. This is one possible profile shape for a wire 30 that includes peaks for abrading a treatment segment 55 rather than just a point about a treatment site 50. FIG. 23B illustrates a front view of the example wire 30 of FIG. 23A. As seen in FIG. 23B, a sinusoidal profile wire 30 existing in two dimensions will have a sinusoidal crossing profile 2302 that resembles a rectangle. When rotated, the sinusoidal crossing profile 2302 is approximately the shape that would be abrading the walls of the vessel within the treatment segment 55.

While the shape of example wires 30 has been shown to be various interpretations of a sinusoidal profile, additional shaped profiles may be realized by the present disclosure. Additionally, the preceding wires 30 have been shown as lying on a two-dimensional plane. As FIGS. 24A and 25A will show, any of the preceding disclosure and figures (i.e., FIGS. 12A, 12B, 12C, 14, 15, 16, 17, 18, 19, 20, 21, 22, and 23A) may also exist in a three-dimensional plane, such as a helix (or spring-shape) or variations where the peaks alternate rotationally about the central axis 1208.

Figure 24A:
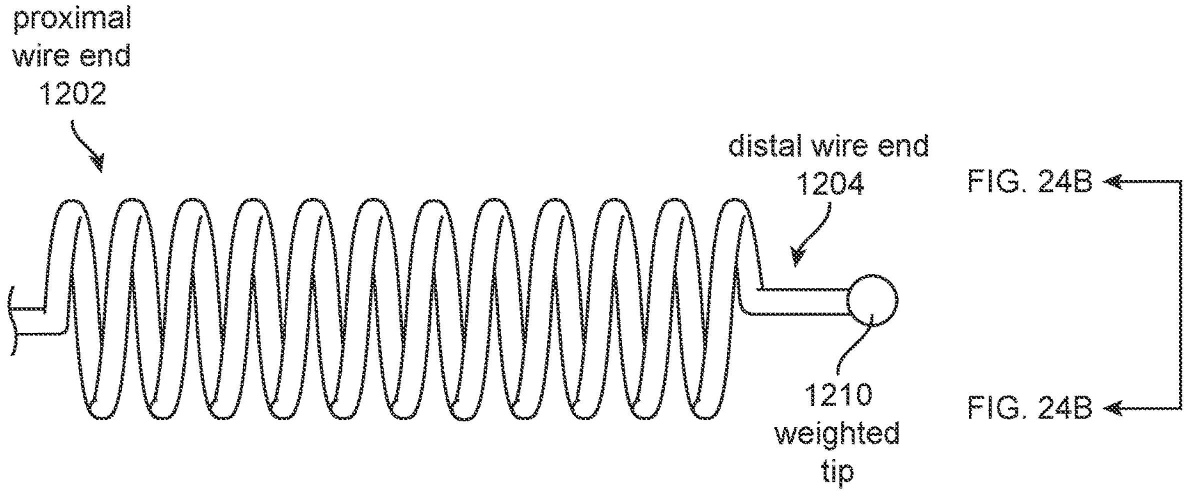
FIG. 24A illustrates an example wire including a spring-like profile.
Figure 24B:
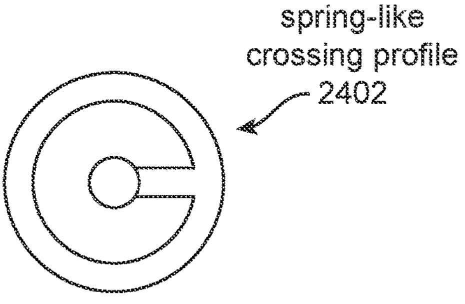
FIG. 24B illustrates a front view of the wire of FIG. 24A, according to some examples.

FIG. 24A illustrates one such three-dimensional example wire 30. The wire 30 of FIG. 24A is similar to the spring-like construction 1902 of FIG. 19, but in FIG. 24A the wire 30 does not present an additional sinusoidally-shaped profile in two dimensions. Rather, the wire 30 is a sinusoid existing in three dimensions, thus forming a helical or spring-like shape. FIG. 24B illustrates a front view of the example wire of FIG. 24A. As seen in FIG. 24B, a helical-shaped wire 30 will have a spring-like crossing profile 2402 that resembles a circle. When rotated, the spring-like crossing profile 2402 is approximately the shape that would be abrading the walls of the vessel within the treatment segment 55.

Figure 25A:
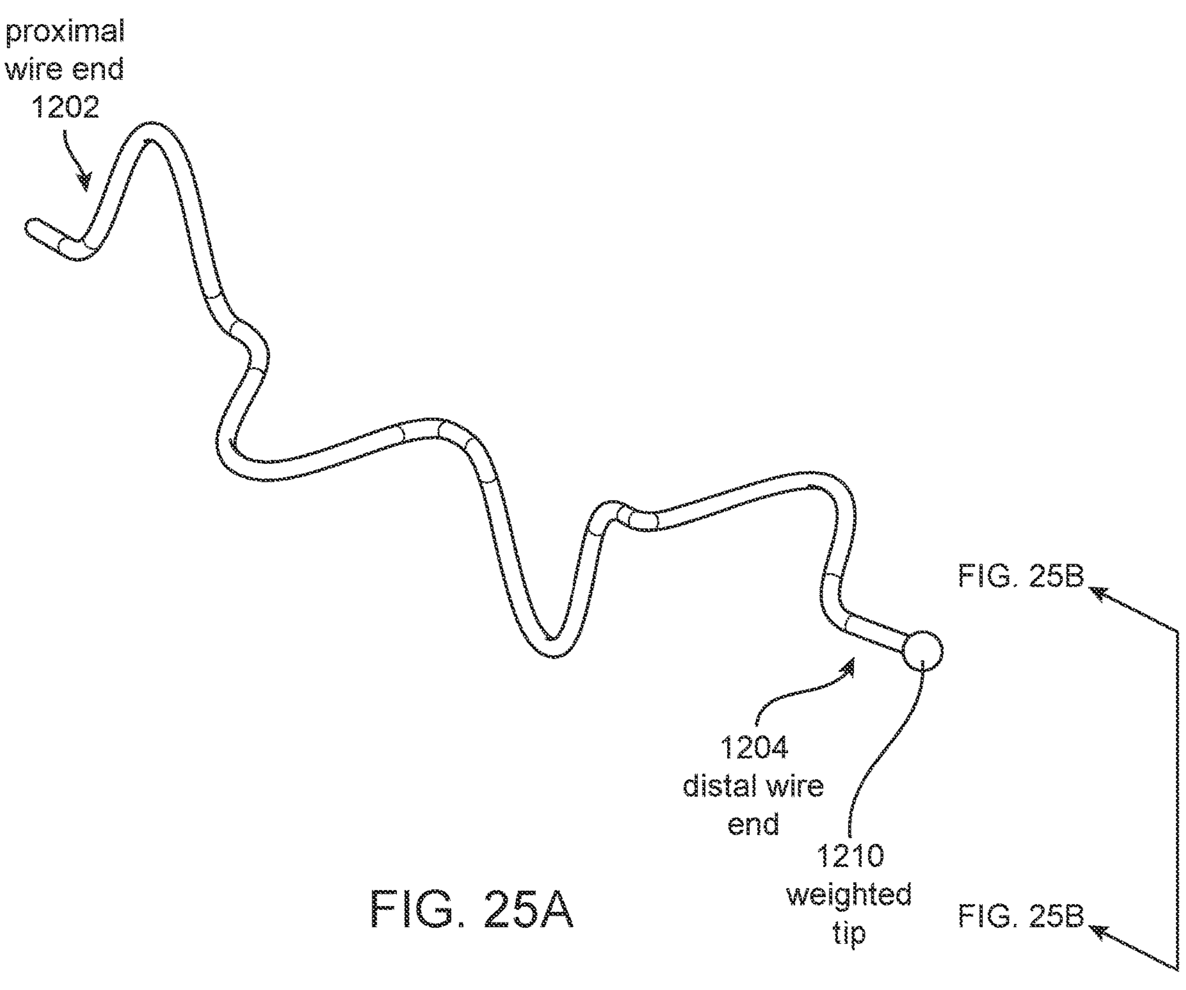
FIG. 25A illustrates an example wire including a profile extending into a third dimension.

FIG. 25A illustrates an example wire 30 where a sinusoidal profile is maneuvered in three-dimensional space after each peak occurs. The possibilities of such a configuration are neigh endless, so FIG. 25A represents just one such example configuration for the purposes of discussion.

In FIG. 25A, every time the wire hits a peak along a sinusoid and returns to the central axis 1208 (not shown), the sinusoid shape rotates clockwise by approximately ninety degrees. Once again, this angle is by example only, and any angle could be selected. Additionally, the decision to rotate clockwise when moving proximal to distal along the wire 30 is also by example only. Counter-clockwise or combinations of clockwise and counter-clockwise rotation may also be implemented. Because FIG. 25A includes four peaks, once the fourth peak has been reached, a full rotation in three-dimensional space will have occurred. Once again, the decision to use four peaks in this example is non-limiting, and any number of peaks along the wire may be included. Likewise, a full rotation in three-dimensional space is also not strictly required.

Figure 25B:
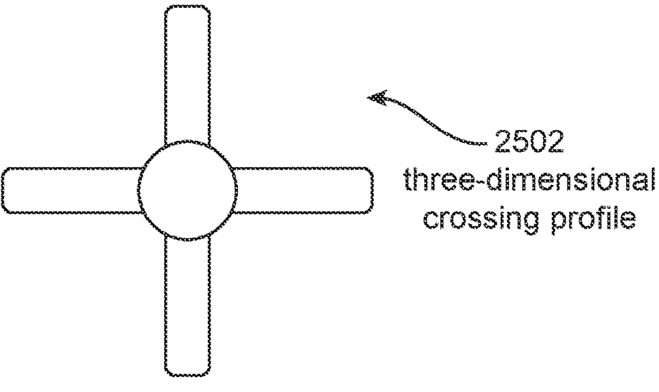
FIG. 25B illustrates a front view of the wire of FIG. 25A, according to some examples.

FIG. 25B illustrates a front view of the example wire of FIG. 25A. Because four peaks were included in the example wire 30 of FIG. 25A, and because the rotation was approximately ninety degrees after every peak, the three-dimensional crossing profile 2502 appears as a cross, or plus sign. In this example, the three-dimensional crossing profile 2502 is approximately the shape that would be abrading the walls of the vessel within the treatment segment 55 when the wire 30 is rotated. This three-dimensional crossing profile 2502 may be influenced in shape by the number of rotations, and the degree of rotation, of the wire 30 after each peak occurs.

Finally, the location at which the rotation occurs is not strictly necessary either. For example, the wire 30 may be rotated in three-dimensional space at each peak instead of at the base of each peak, as shown in FIGS. 25A and 25B. The rotation may also occur at any point between the peak and the base of the peak. Additionally, any combinations of these rotation points may be used—for example, the first rotation happening at the base after the first peak occurs and the next rotation happening at the second peak.

FIGS. 26A, 26B, 26C, 26D, 26E, 26F, 26G, and 26H illustrate side views of example proximal features 2602 for the wire 30. In the cases of FIGS. 26A, 26B, 26C, 26D, 26E, 26F, and 26G, the proximal features 2602 may be capable of at least partially occluding the vessel proximal to the area of treatment. This occlusion, or flow arrest, may help to prevent blood from entering the area of treatment. While blood entering the treatment site 50 is not debilitating to the procedure, there is a chance that too much blood will dilute the drug, or sclerosant, thus lowering its efficacy and the effectiveness of the treatment as a whole. This occlusion, or flow arrest, may also help to stop or slow the blood flow, allowing the sclerosant to dwell in the treatment site 50 longer, increasing the efficacy of the sclerosant. This occlusion may further help to prevent the drug from leaving the treatment site 50 in the proximal direction.

It is understood that any of the proximal features 2602 as shown in FIGS. 26A, 26B, 26C, 26D, 26E, 26F, 26G, and 26H may be used in combination with any of the various wire 30 examples as shown and described previously in FIGS. 12A, 12B, 12C, 14, 15, 16, 17, 18, 19, 20, 21, 22A, 22B, 22C, 23A, 24A, and 25A, as well as any additional wire not specifically illustrated herein.

Figure 26A:
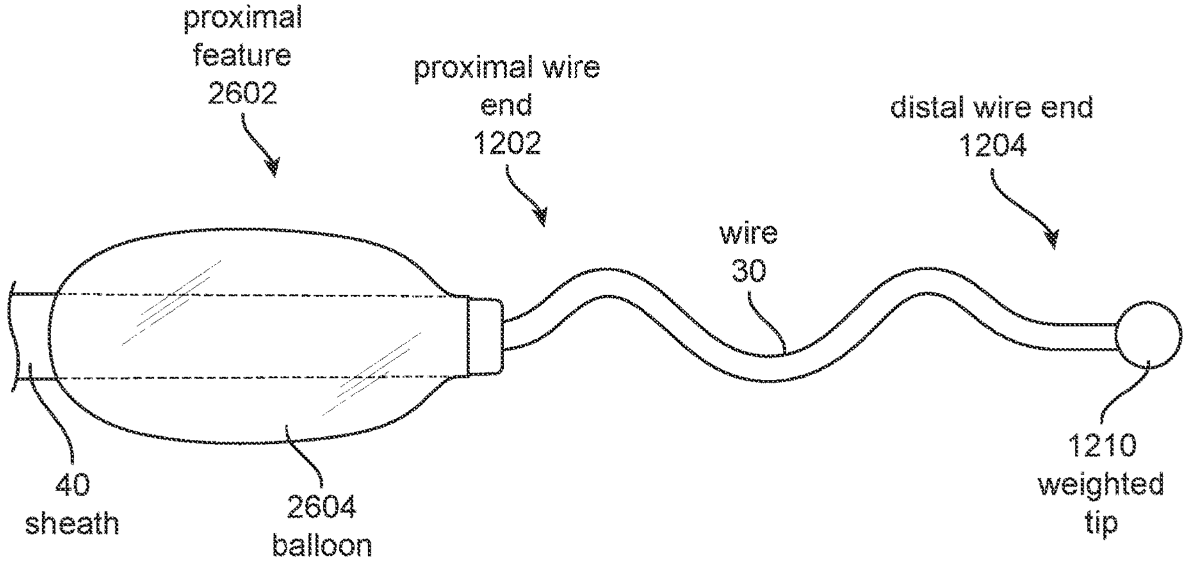
FIGS. 26A, 26B, 26C, 26D, 26E, 26F, 26G, and 26H illustrate side views of example proximal features for a wire and/or sheath.

With respect to FIG. 26A, a balloon 2604 may be proximal to the exposed portion of the wire 30 and reside upon the sheath 40. After the wire 30 is deployed from the sheath 40, the balloon 2604 may be inflated via an inflation lumen, perhaps a working lumen in the sheath 40, to occlude the vessel. In some examples, the balloon 2604 may include a weeping balloon, and a drug, such as sclerosant, may be delivered through the micropores of the weeping balloon.

Figure 26B:
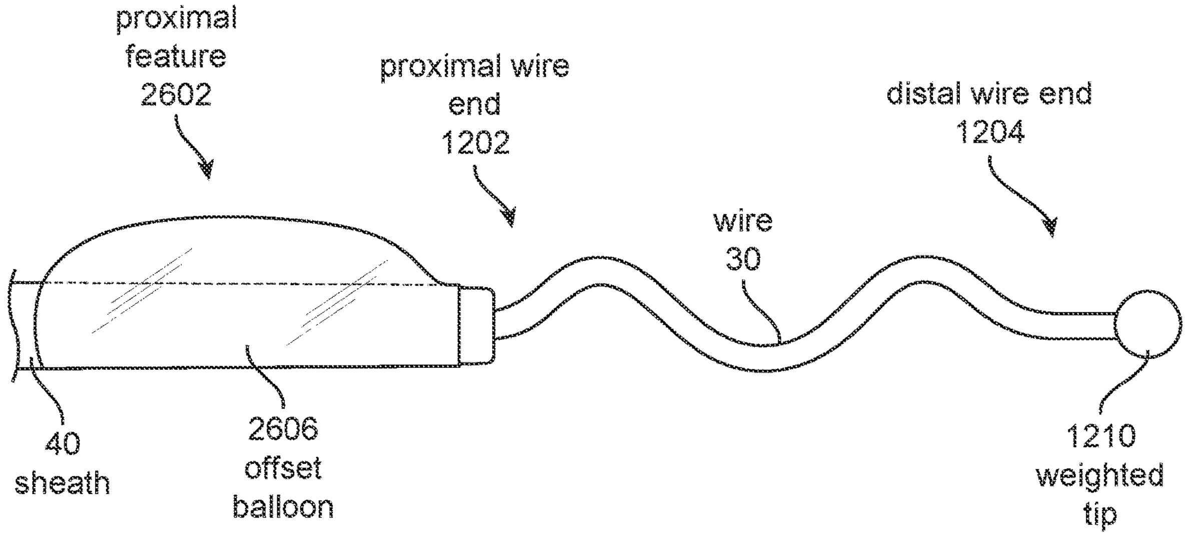

FIG. 26B is similar to FIG. 26A, in that an offset balloon 2606 may reside upon the sheath 40 proximal to the exposed portion of the wire 30. Again, after the wire 30 is deployed from the sheath 40, the offset balloon 2606 may be inflated via an inflation lumen, perhaps a working lumen in the sheath 40, to occlude the vessel. Also similarly, the offset balloon 2606 may include a weeping balloon, and a drug, such as sclerosant, may be delivered through the micropores of the weeping balloon. However, dissimilar to the balloon 2604 of FIG. 26A, the offset balloon 2606 of FIG. 26B may be biased toward one side of the sheath 40. In such examples, the offset balloon 2606 may offload the wire 30 while in an inflated state, thereby causing the wire 30 to make more aggressive contact with the wall of the vessel.

Figure 26C:
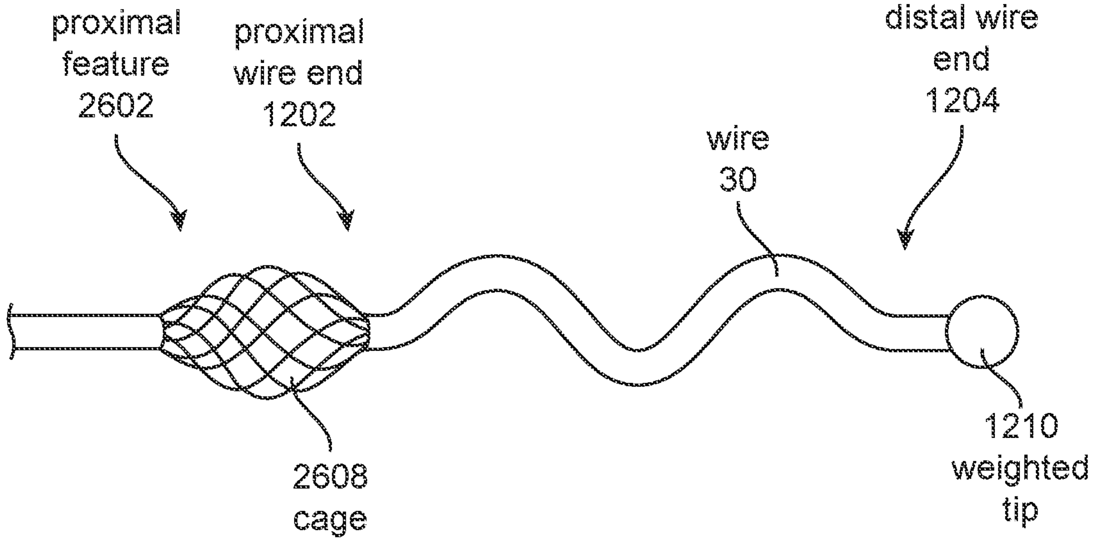
Figure 26D:
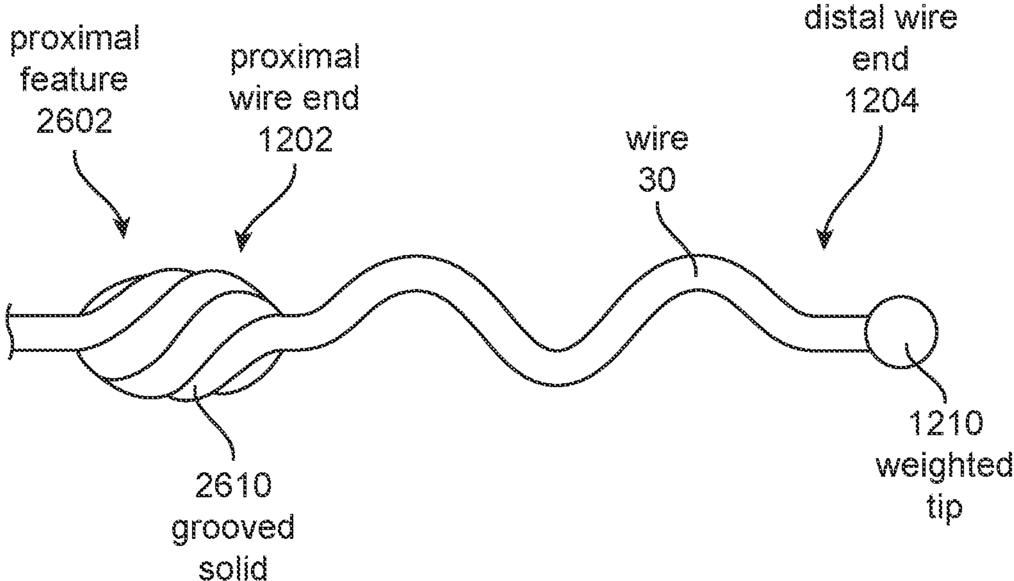

FIGS. 26C and 26D depict hollow and solid variations of a spiral-type occlusion element. Specifically, FIG. 26C illustrates a cage 2608, which, when released from the sheath 40, expands to approximately the same diameter as the vessel. In this example, the cage 2608 is made from a material, such as Nitinol, which permits expansion and contraction of the cage 2608. The cage 2608, when rotating, may act as a three-dimensional impeller, which will at least partially impede the progress of blood into the treatment site 50 and/or the outflow of a drug from said treatment site 50. In some examples, the cage 2608 is made from a material that does not permit compression, and as such, it is sized to fit within the sheath 40.

FIG. 26D illustrates a grooved solid 2610, which acts in a similar manner to the cage of FIG. 26C. The grooved solid 2610, however, may be smaller in diameter than the cage 2608, as it cannot compress as far and must still fit within the sheath 40 when it is not in its released state. The solid nature of the grooved solid 2610 prevents any blood from entering the treatment site 50 through the grooved solid 2610, as well as any potential outflow of a drug from said treatment site 50, and the grooves in the grooved solid 2610 perform an impelling action to prevent at least some blood from going around the grooved solid 2610 and into the treatment site 50.

Figure 26E:
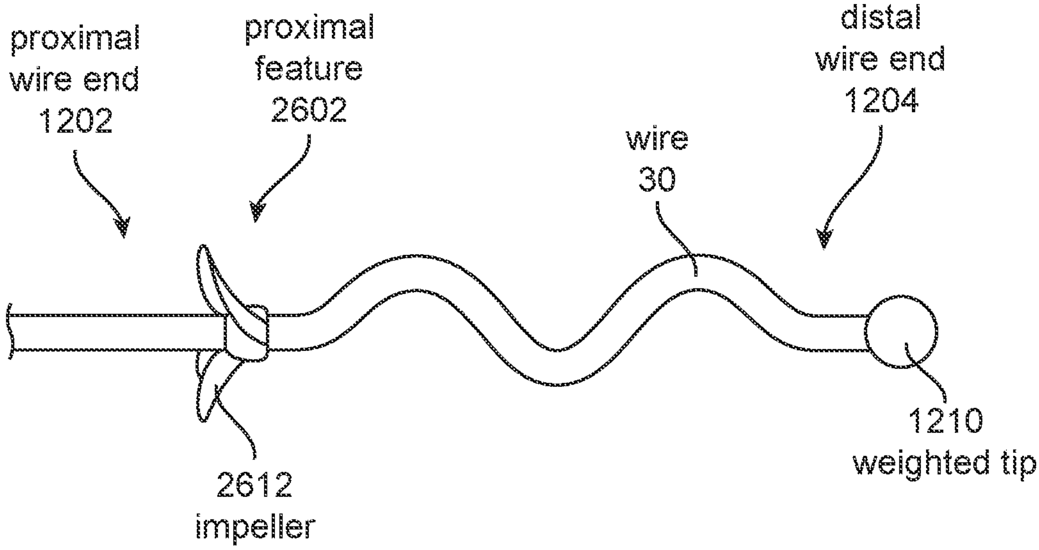

FIG. 26E shows an impeller 2612 having three blades. The number of blades is not important, and as many blades as desired may be used. The impeller 2612 may be made from a material, such as Nitinol, which permits expansion and contraction of the impeller 2612. In this example, the impeller 2612 may be sized larger than the sheath 40 diameter. The impeller 2612 may then expand to approximately the same diameter as the vessel when released from the sheath 40. In other examples, the impeller 2612 is made from a material that does not expand and contract very much, and as such, the impeller 2612 would be sized to fit within the sheath 40 when in its retracted state. When the wire 30 rotates, the impeller 2612 would also rotate, thus impeding the progress of blood to the treatment site 50.

Figure 26F:
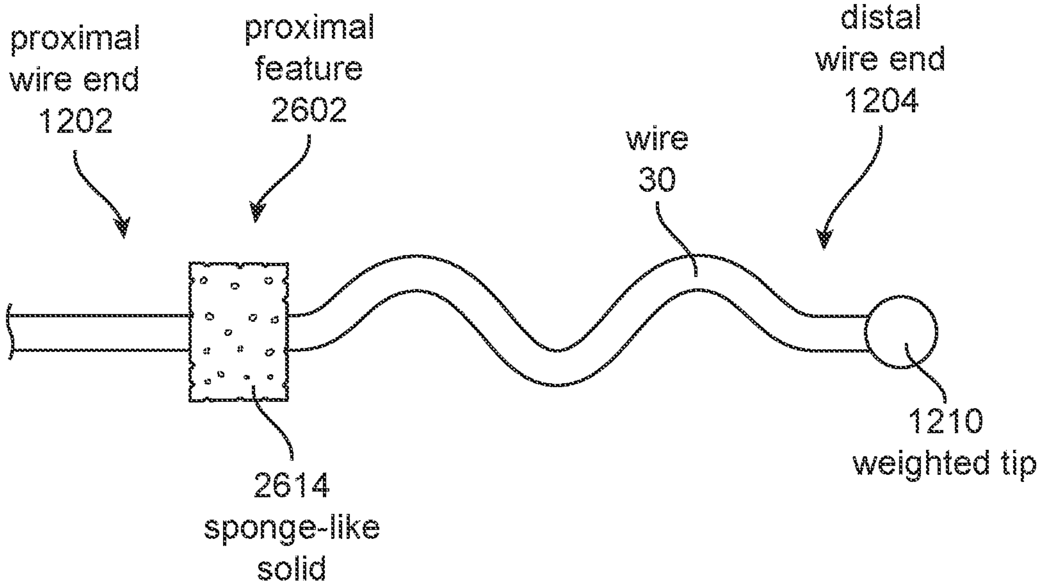
Figure 26G:
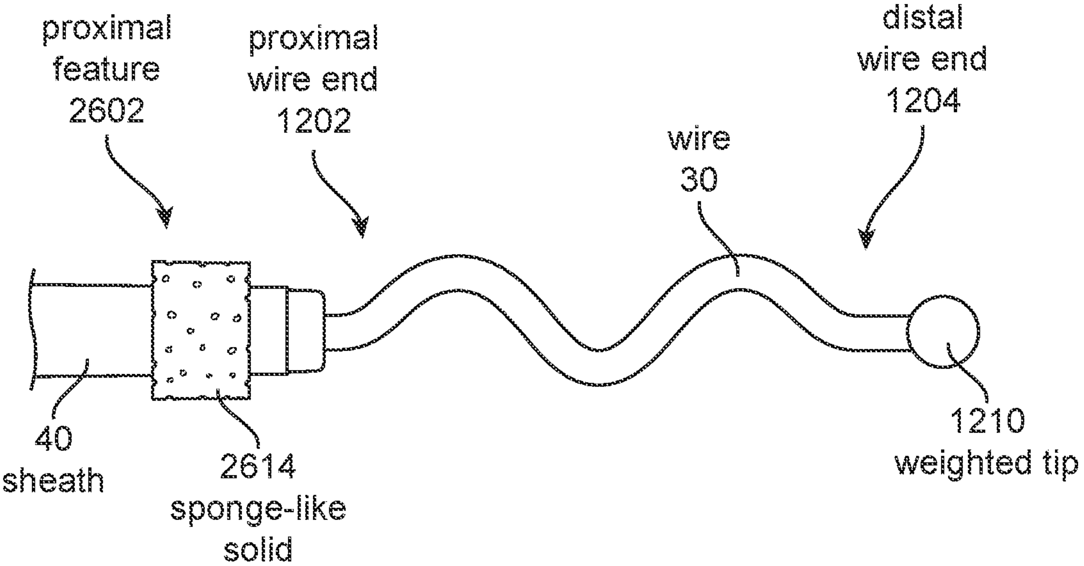

FIGS. 26F and 26G show a sponge-like solid 2614 as the proximal feature 2602. Specifically, in FIG. 26F, the sponge-like solid 2614 resides on the wire 30. The sponge-like solid 2614 may easily compress within the sheath 40 when in its retracted configuration and can expand to occlude the vessel proximal to the treatment site 50 when released from the sheath 40.

Similarly, in FIG. 26G, the sponge-like solid 2614 acts as the proximal feature 2602, but in this case, the sponge-like solid 2614 resides on the sheath 40. The sponge-like solid 2614 may easily compress within the vasculature of the patient, and once delivered be permitted to expand in order to occlude the vessel proximal to the treatment site 50. In both FIGS. 26F and 26G, the sponge-like solid 2614 may prevent blood from entering the treatment site 50 during treatment, and/or prevent a drug, such as sclerosant, from leaving the treatment site 50 during treatment.

Figure 26H:
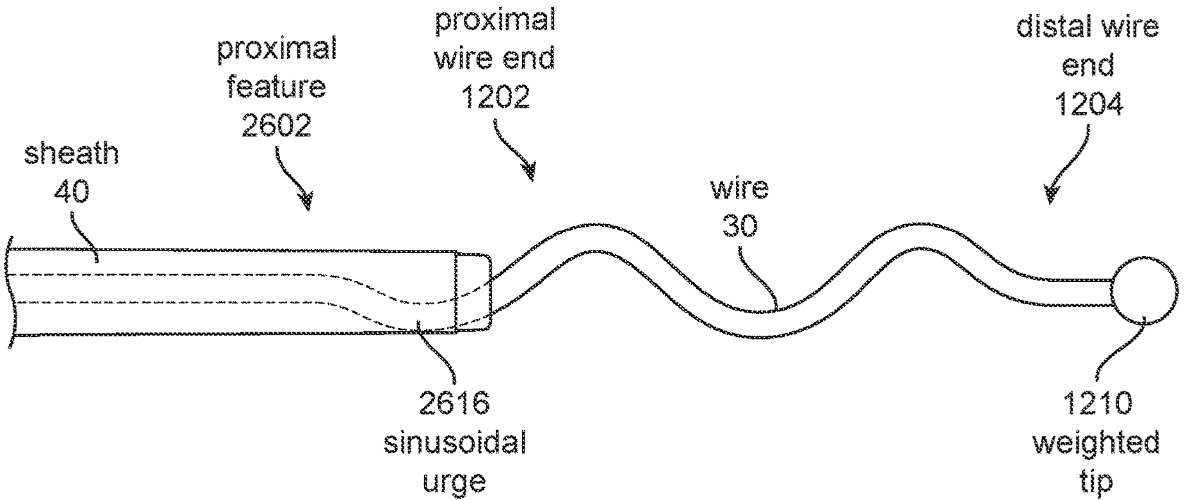

FIG. 26H illustrates a sinusoidal urge 2616 in the wire 30 proximal to the distal wire end 1204 within the sheath 40. This sinusoidal urge 2616 may still exist within the sheath 40 when the sheath 40 is fully retracted about the wire 30. The sinusoidal urge 2616 is not intended to occlude blood flow, but rather, may offload the wire 30 in order to cause the wire 30 to make more aggressive contact with the wall of the vessel.

FIGS. 27A, 27B, 27C, 27D, and 27E illustrate side views of various potential distal features 2702 for a wire. In all cases, the distal features 2702 at least partially occlude the vessel distal to the area of treatment. This occlusion, or flow arrest, may help to prevent a drug, such as sclerosant, from traveling too far into a vessel, such as into a junction with another, more major vessel that it is not desirable to treat. This occlusion, or flow arrest, may also prevent any blood from traversing into the treatment site 50 from the distal side, which could potentially dilute the drug being delivered.

It is understood that any of the distal features 2702 as shown in FIGS. 27A, 27B, 27C, 27D, and 27E may be used in combination with any of the various wire 30 examples as shown and described previously in FIGS. 12A, 12B, 12C, 14, 15, 16, 17, 18, 19, 20, 21, 22A, 22B, 22C, 23A, 24A, and 25A, as well as any additional wire not specifically illustrated herein.

Figure 27A:
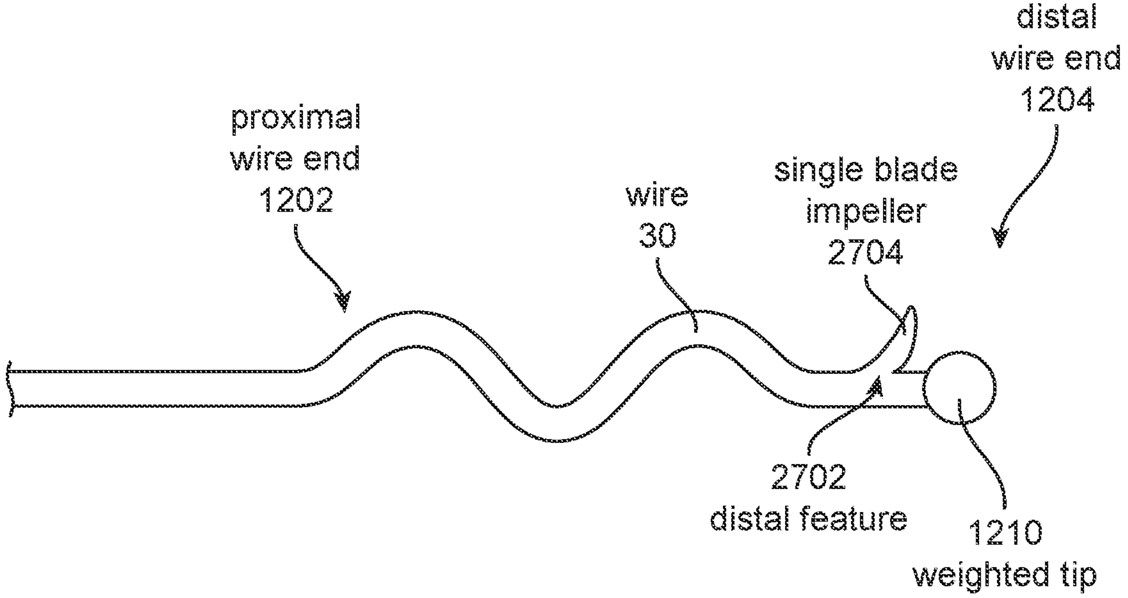
FIGS. 27A, 27B, 27C, 27D, and 27E illustrate side views of example distal features for a wire.

With respect to FIG. 27A, a single blade impeller 2704 may be distal to the wire 30. As the wire 30 is released from the sheath 40, the single blade impeller 2704 may expand to be approximately the same length as the radius of the vessel. In these examples, the single blade impeller 2704 is made from a material, such as Nitinol, that allows this expansion and contraction of the single blade impeller 2704.

In other examples, the single blade impeller 2704 may be sized to fit within the sheath 40 while in its fully expanded configuration, and made of a material that is more rigid, and does not permit as much expansion or contraction. When the wire 30 rotates, the single blade impeller 2704 rotates as well, impeding the progress of a drug, such as sclerosant, out of the treatment site 50. Because the single blade impeller 2704 cannot be symmetrical about the wire 30 (as you cannot have symmetry around a circle with only one component), the single blade impeller 2704 may not be able to be used with a gyroscopic effect. Similar to the off-axis terminating wire 30 of FIGS. 14 and 21, the single blade impeller 2704 may cause the wire 30 to move eccentrically, creating more aggressive contact with the vessel walls.

Figure 27B:
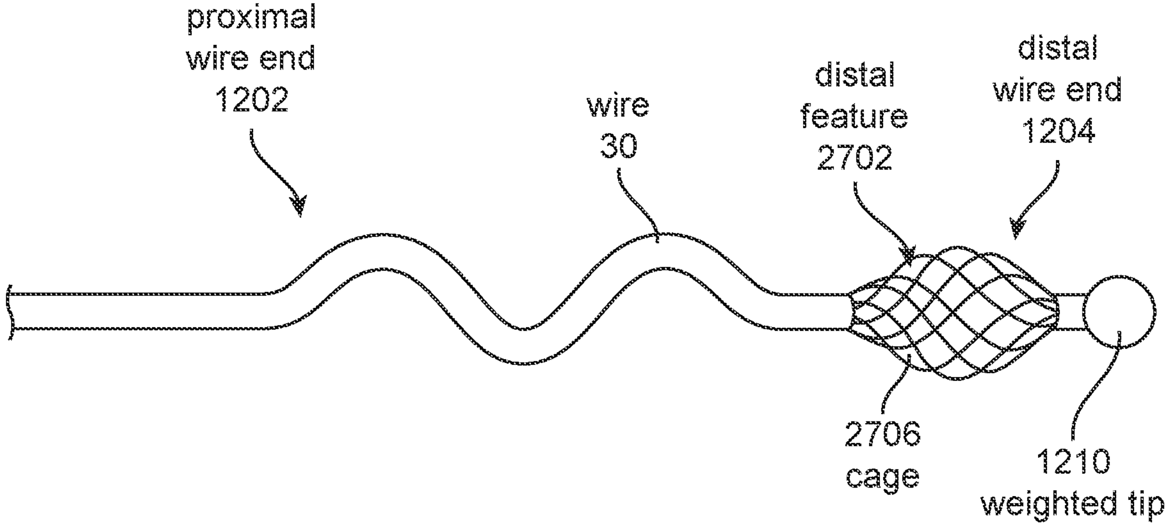
Figure 27C:
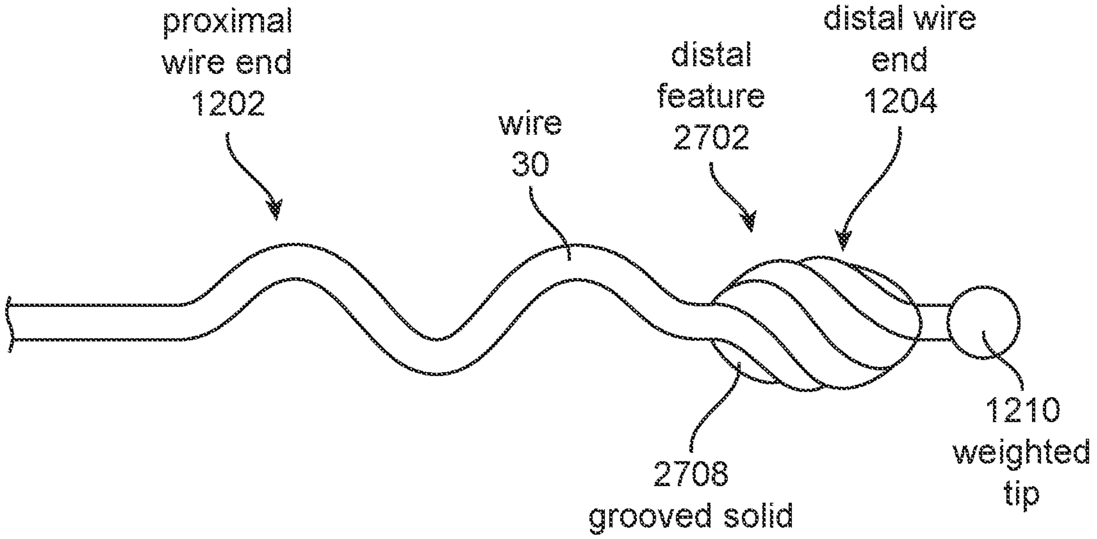

FIGS. 27B and 27C depict hollow and solid variations of a spiral-type occlusion element at the distal wire end 1204. Specifically, 27B illustrates a cage 2706 which, when released from the sheath 40, expands to approximately the same diameter as the vessel. In this example, the cage 2706 is made from a material, such as Nitinol, which permits expansion and contraction of the cage 2706. The cage 2706, when rotating, may act as a three-dimensional impeller, which will at least partially impede the progress of a drug, such as sclerosant, out of the treatment site 50 while also preventing unintended inflow of blood into said treatment site 50. In some examples, the cage 2706 is made from a material that does not permit compression, and as such, it is sized to fit within the sheath 40.

FIG. 27C illustrates a grooved solid 2708, which acts in a similar manner to the cage 2706 of FIG. 27B. The grooved solid 2708, however, is smaller in diameter than the cage 1006, as it cannot compress as far, and must still fit within the sheath 40 when it is not in its released state. The solid nature of the grooved solid 2708 prevents any of a delivered drug, such as sclerosant, from exiting the treatment site 50 through the grooved solid 2708, and the grooves in the grooved solid 2708 perform an impelling action to prevent at least some of the drug from going around the grooved solid 2708 and out of the treatment site 50. Similar to FIG. 27B, the grooved solid 2708 may also prevent any unintended inflow of blood into the treatment site 50 from the distal side.

Figure 27D:
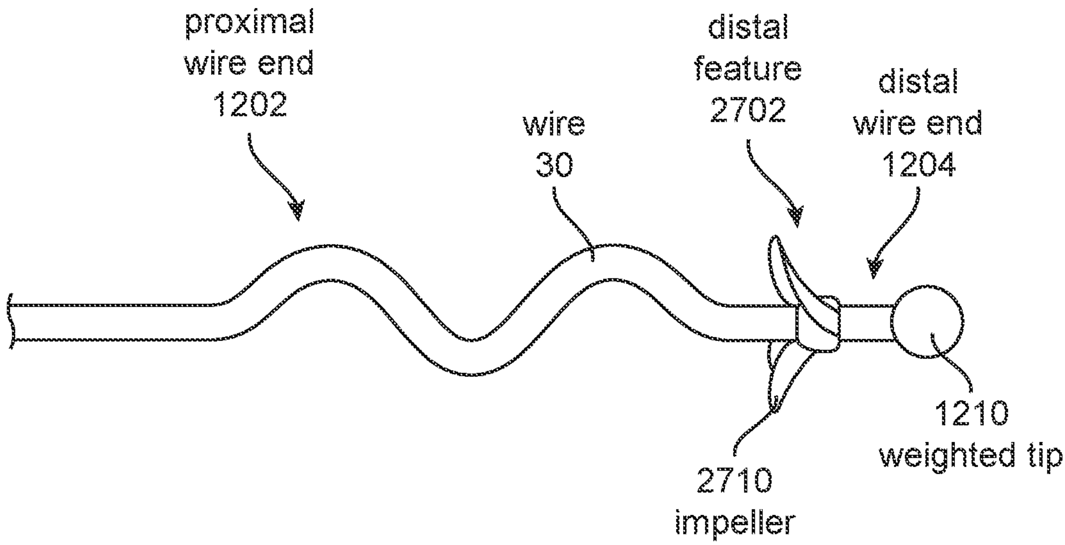

FIG. 27D shows an impeller 2710 having three blades. The number of blades is not important, and as many blades as desired may be used. The impeller 2710 may be made from a material, such as Nitinol, which permits expansion and contraction of the impeller 2710. In this example, the impeller 2710 may be sized larger than the sheath 40 diameter. The impeller 2710 may then expand to approximately the same diameter as the vessel when released from the sheath 40. In other examples, the impeller 2710 is made from a material that does not expand and contract very much, and as such, the impeller 2710 would be sized to fit within the sheath 40 when in its retracted state. When the wire 30 rotates, the impeller 2710 would also rotate, thus impeding the progress of a drug, such as sclerosant, out of treatment site 50. This impeding effect may also extend to preventing any unintended inflow of blood into the treatment site 50.

Figure 27E:
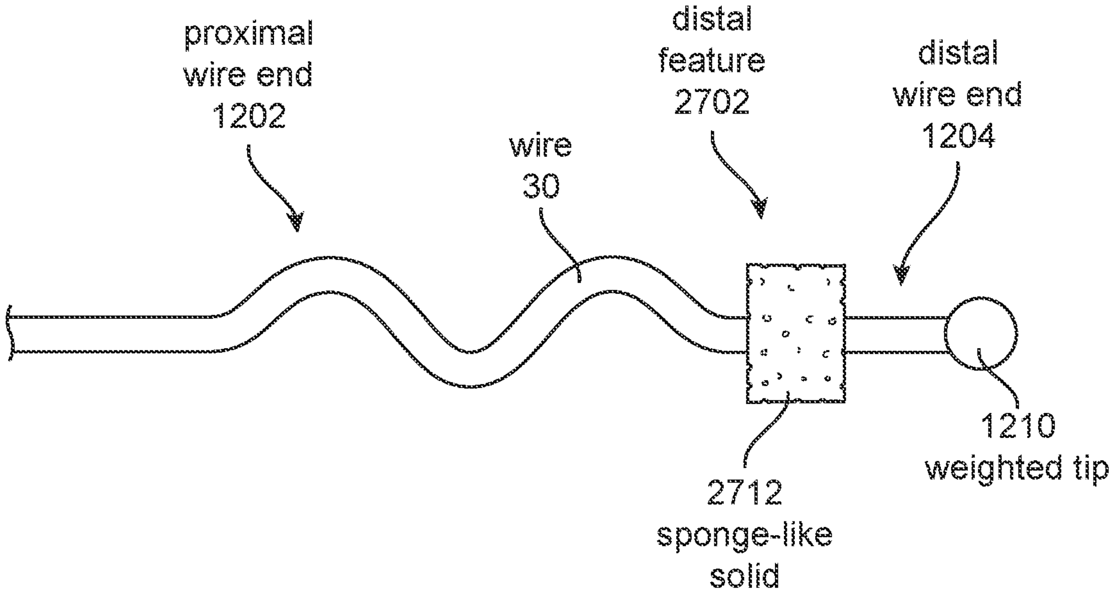

FIG. 27E shows a sponge-like solid 2712. The sponge-like solid 2712 may easily compress within the sheath 40 when in its retracted configuration and can expand to occlude the vessel distal to the treatment site 50 when released from the sheath 40. Dissimilar to the proximal feature 2602 sponge-like solid 2614, the distal feature 2702 sponge-like solid 2712 cannot reside upon the sheath 40, as once the sheath 40 is retracted about the wire 30 in order to expose the wire 30, the sponge-like solid 2712 could no longer be at the distal end of the treatment site 50.

Figure 28A:
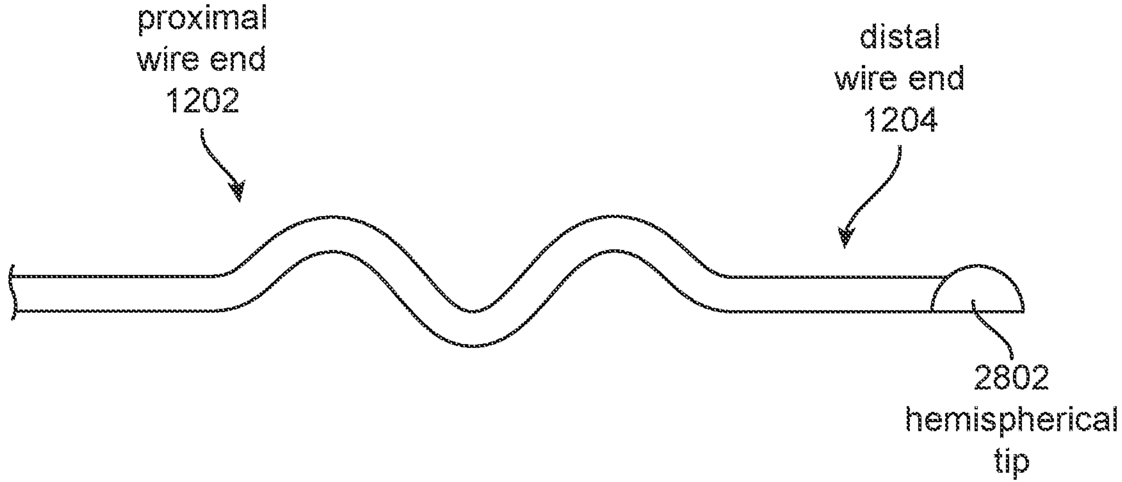
FIGS. 28A, 28B, and 28C illustrate various examples of wires including various features at a distalmost tip.
Figure 28B:
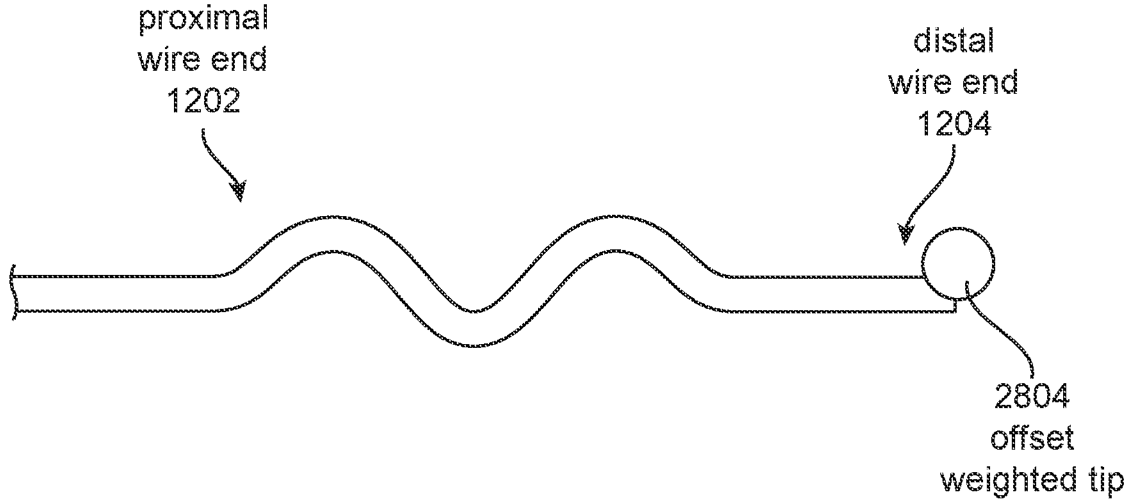
Figure 28C:
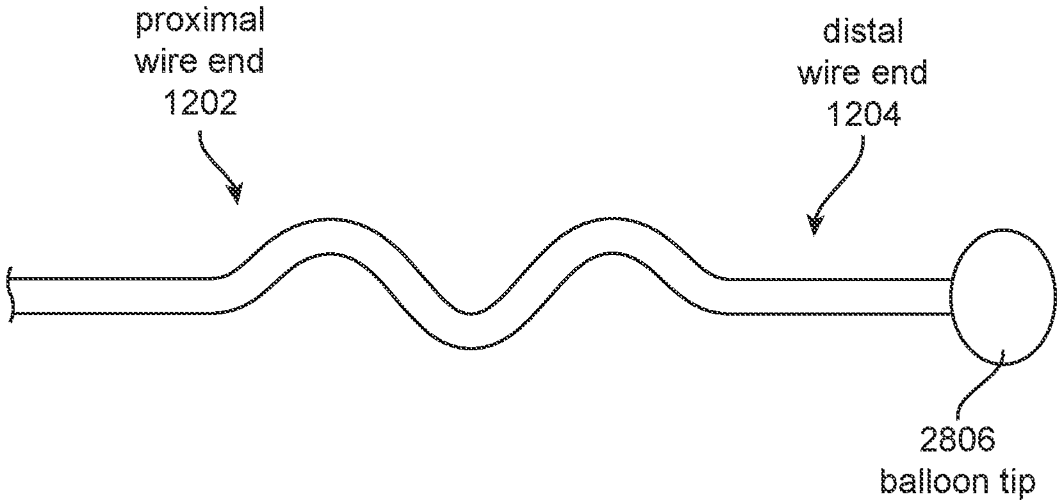

FIGS. 28A, 28B, and 28C illustrate side views of example wires 30, including additional features at a distalmost tip of the wire 30. While many of the preceding figures included a weighted tip 1210 at the distalmost tip of the wire 30, the weighted tip 1210 is not necessary (such as seen in FIG. 12A, where the tip included an aperture 1206). FIGS. 28A, 28B, and 28C provide additional examples of distalmost tips of the wire 30 that are not necessarily intended to keep the wire gyroscopically stable during rotation.

It is understood that any of the additional features at a distalmost tip of the wire 30 as shown in FIGS. 28A, 28B, and 28C may be used in combination with any of the various wire 30 examples as shown and described previously in FIGS. 12A, 12B, 12C, 14, 15, 16, 17, 18, 19, 20, 21, 22A, 22B, 22C, 23A, 24A, and 25A, as well as any additional wire not specifically illustrated herein.

FIG. 28A illustrates a hemispherical tip 2802 at the distalmost tip of the wire 30. This hemispherical tip 2802 may be weighted or unweighted. In either case, the hemispherical tip 2802, because of its lack of three-dimensional symmetry, may unbalance the distalmost tip of the wire 30, causing an opposing effect to gyroscopic stability. This effect may cause the hemispherical tip 2802 to make contact, perhaps aggressive contact, with the vessel wall, adding an additional point of abrasion to the treatment segment 55 in which the wire 30 is located.

FIG. 28B illustrates an offset weighted tip 2804 at the distalmost tip of the wire 30. The offset weighted tip 2804 need not necessarily be weighted, but weight may increase the effect this distalmost tip has on the wire 30. Similar to the hemispherical tip 2802 of FIG. 28A, this offset weighted tip 2804 may cause an opposing effect to gyroscopic stability through unbalancing the wire because of its newly acquired lack of symmetry about the central axis 1208 (not shown in this figure). This effect may cause the offset weighted tip 2804 to make contact (again, perhaps aggressive contact) with the vessel wall by adding an additional point of abrasion to the treatment segment 55 in which the wire 30 is located.

FIG. 28C illustrates a balloon tip 2806 at the distalmost tip of the wire 30. This balloon tip 2806 may be delivered to a treatment site 50 in an unexpanded (or uninflated) configuration and then inflated in order to expand and occlude the vessel distal of the treatment site 50. In such examples, it is likely that the wire 30 includes a lumen, or is a hypotube, in order to deliver an inflation fluid to the balloon tip 2806 in order to permit the balloon tip 2806 to inflate to its expanded configuration.

Figure 29A:
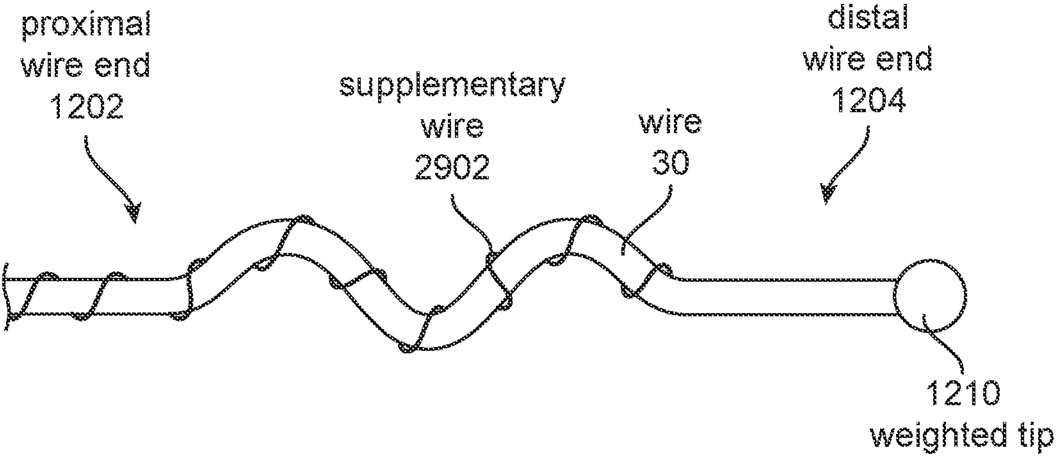
FIGS. 29A, 29B, and 29C illustrate side views of example wires having additional features at a distal wire end.

FIG. 29A illustrates an example side view of a wire 30, including a supplementary wire 2902. The supplementary wire 2902 may add supplemental geometry along different portions of the wire 30, creating a rougher surface and "snag" points to facilitate greater abrasion of the vessel wall. While the supplementary wire 2902 is shown wrapped around the majority of the wire 30, the supplementary wire 2902 may be wrapped around only small portions of the wire, such as near the peaks, in order to cut down on material use (and perhaps the cost of materials).

While not specifically shown in FIG. 29A, in some examples, the supplementary wire 2902 may be a hypotube that extends back to the controller 20, permitting the supplementary wire 2902 to be used as a fluid lumen for delivery of a drug, such as a sclerosant, to the treatment site 50. In these examples, apertures may exist along the length of the supplementary wire 2902 along where it would be located in a treatment segment 55, or at a distal-most end of the supplementary wire 2902 for a distal injection of the drug.

It is understood that the supplementary wire 2902 as shown in FIG. 29A may be used in combination with any of the various wire 30 examples as shown and described previously in FIGS. 12A, 12B, 12C, 14, 15, 16, 17, 18, 19, 20, 21, 22A, 22B, 22C, 23A, 24A, and 25A, as well as any additional wire not specifically illustrated herein.

Figure 29B:
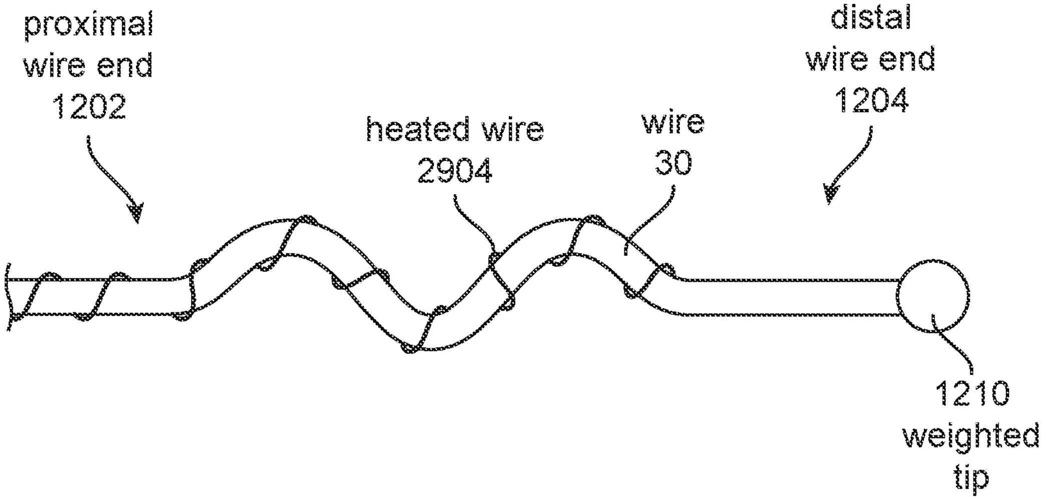

FIG. 29B illustrates a side view of an example wire 30 including supplemental geometry that appears quite similar to the supplementary wire 2902 of FIG. 29A. Dissimilar to the supplementary wire 2902 of FIG. 29A, however, this supplemental geometry is a heated wire 2904. The heated wire 2904 may be capable of carrying heat to the treatment segment 55, thereby increasing the temperature in said treatment segment 55. Through heating up this treatment segment 55, any drug injected therein may see improved drug diffusion.

It is understood that the heated wire 2904 as shown in FIG. 29B may be used in combination with any of the various wire 30 examples as shown and described previously in FIGS. 12A, 12B, 12C, 14, 15, 16, 17, 18, 19, 20, 21, 22A, 22B, 22C, 23A, 24A, and 25A, as well as any additional wire not specifically illustrated herein.

The heated wire 2904 may also be an additional wire made of a shape memory material, such as Nitinol, and the heat portion of "heated wire" may be provided by the body of the patient the wire 30 is inserted into. In these cases, the austenite transformation finish temperature (A(f) temperature) may be set on the shape memory material such that it returns to its austenite state from its martensite state under these bodily provided temperatures. In such examples, the wire 30 may be delivered to a treatment segment 55 in a somewhat straight state, and the heated wire 2904 will begin heating up during this delivery. Once the wire 30 has been delivered to the treatment segment 55 and exposed from the sheath 40, the heated wire 2904 may be permitted to reach its A(f) temperature, thus returning to its austenite shape and forcing the wire 30 into the desired profile for abrading the vessel wall.

Figure 29C:
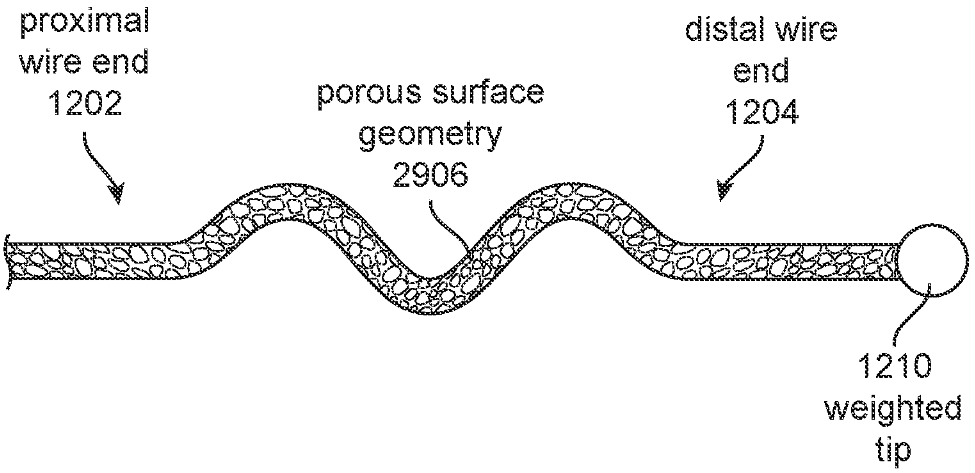

FIG. 29C illustrates a wire 30, including a porous surface geometry 2906, according to some examples. This porous surface geometry 2906 may add a surface roughness to the wire, as alluded to in FIGS. 13A and 15. The porous surface geometry 2906 may prevent smooth surface portions of the wire 30 from contacting the vessel walls in a treatment segment 55. Instead, the porous surface geometry 2906 may cause sharper edges and uneven surfaces to physically contact the vessel walls, thus more aggressively abrading the vessel walls.

It is understood that the porous surface geometry 2906 as shown in FIG. 29C may be used in combination with any of the various wire 30 examples as shown and described previously in FIGS. 12A, 12B, 12C, 14, 15, 16, 17, 18, 19, 20, 21, 22A, 22B, 22C, 23A, 24A, and 25A, as well as any additional wire not specifically illustrated herein.

Figure 30A:
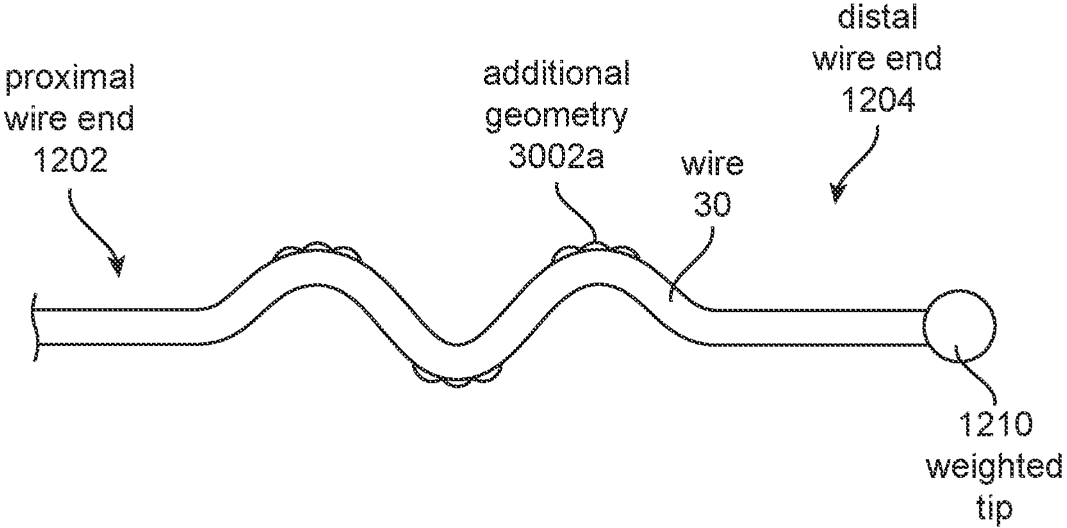
FIGS. 30A, 30B, 30C, and 30D illustrate side views of example wires having additional geometry about a wire.
Figure 30B:
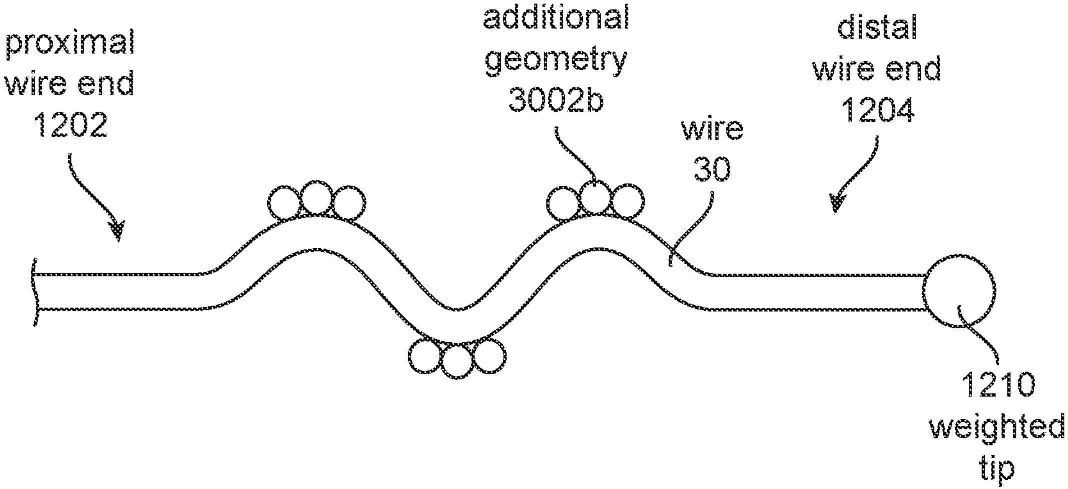
Figure 30C:
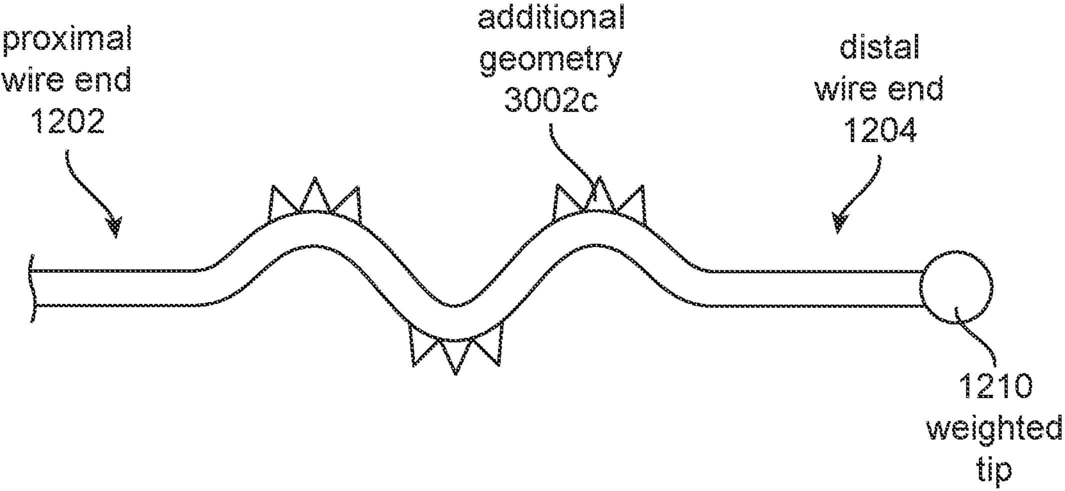
Figure 30D:
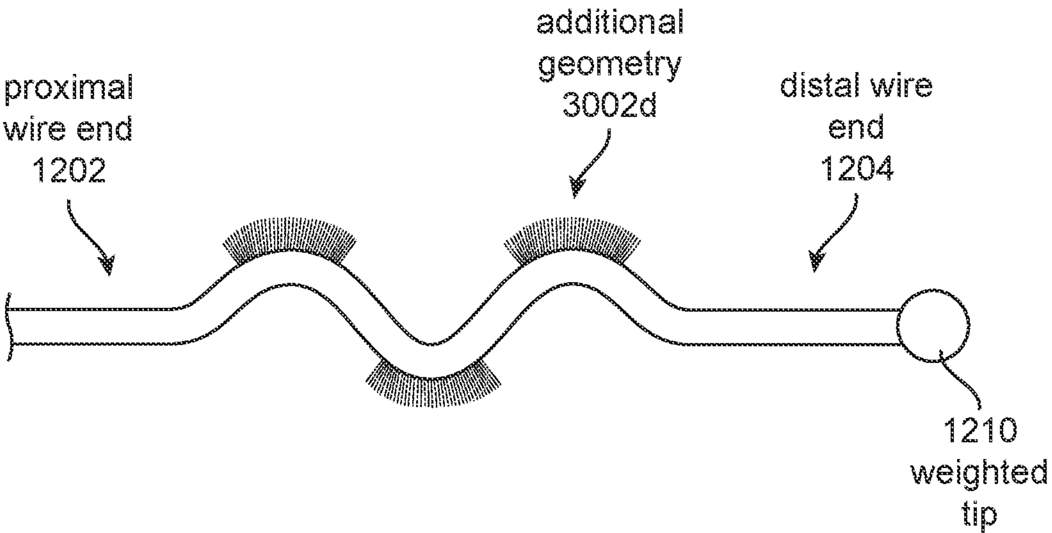

FIGS. 30A, 30B, 30C, and 30D illustrate various examples of wires, including additional geometry. For example, the additional geometry 3002_a_ of FIG. 30A may consist of rounded nubs, either in two or three dimensions. The additional geometry 3002_b_ of FIG. 30B may be at least one ball-shaped object, either in two or three dimensions. In some examples, the additional geometry 3002_c_, as seen in FIG. 30C, is a spike—again, either in two or three dimensions. The additional geometry 3002_d_ of FIG. 30D may be a brush, or brush-like object.

Any of these additional geometries 3002_a_, 3002_b_, 3002_c_, and/or 3002_d_ may be used in conjunction with one another. These additional geometries 3002_a_, 3002_b_, 3002_c_, and/or 3002_d_ may facilitate abrasion of the vessel wall along a treatment segment 55. Additionally, while the additional geometries 3002_a_, 3002_b_, 3002_c_, and/or 3002_d_ are shown only at the peaks of the sinusoidal shape of wire 30 presented in FIGS. 30A, 30B, 30C, and 30D, it is understood that these additional geometries 3002_a_, 3002_b_, 3002_c_, and/or 3002_d_ may be included at any location of the wire 30, including the entire body of the wire 30, as desired by the user.

It is understood that any of the additional geometries 3002_a_, 3002_b_, 3002_c_, and/or 3002_d_ as shown in FIGS. 30A, 30B, 30C, and 30D may be used in combination with any of the various wire 30 examples as shown and described previously in FIGS. 12A, 12B, 12C, 14, 15, 16, 17, 18, 19, 20, 21, 22A, 22B, 22C, 23A, 24A, and 25A, as well as any additional wire not specifically illustrated herein.

Figure 31:
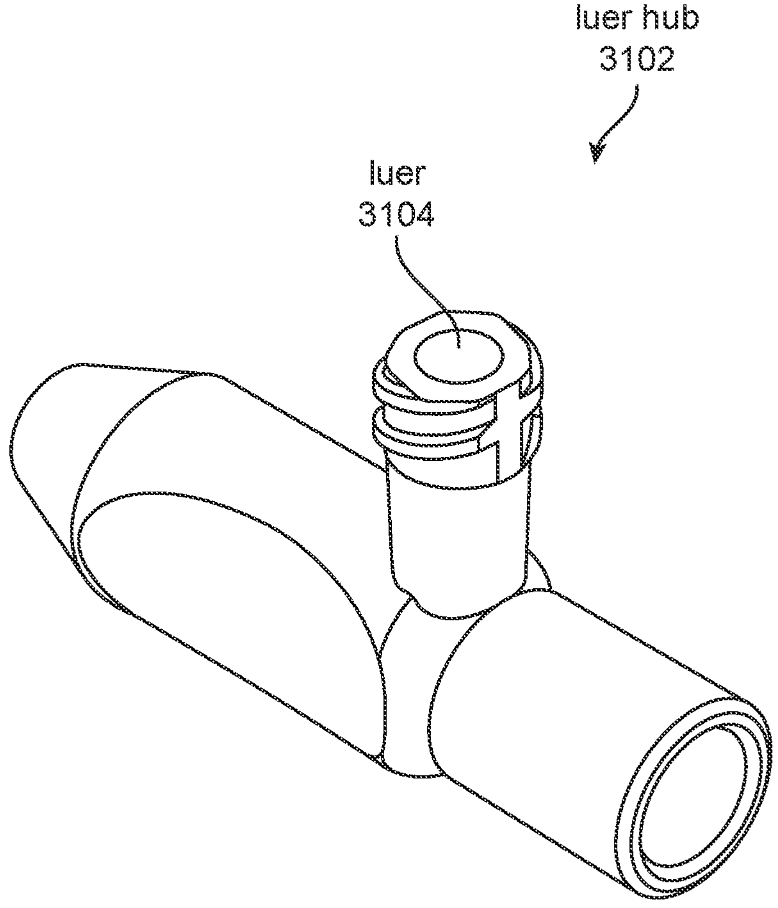
FIG. 31 illustrates an example luer hub.

FIG. 31 illustrates an example luer hub 3102, including a luer 3104. This luer hub 3102 may be the mechanism by which the syringe 60 is detachably coupled to the T-fitting 706, 804, and/or 904 (of FIGS. 7, 8, 9A, 9B, and 9C) or the saddle 704 of FIG. 7 (or those saddles not shown but described in FIGS. 8, 9A, 9B, and 9C).

Figure 32:
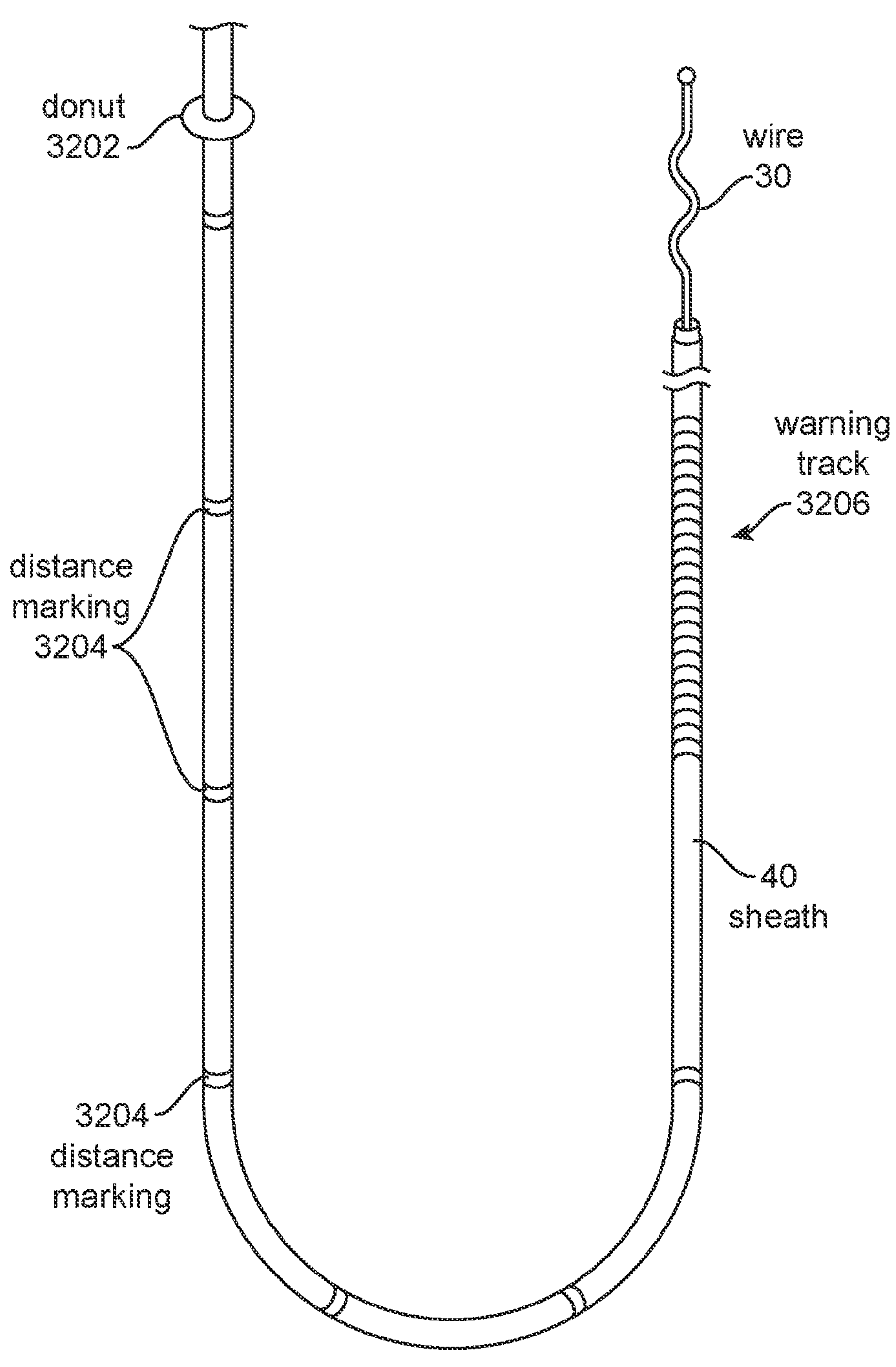
FIG. 32 illustrates a sheath including various features and a wire, according to some examples.

FIG. 32 illustrates a top view of an example catheter 15, including a sheath 40 and a wire 30. Multiple marking devices are shown on the body of the sheath 40. Any of these marking devices may partially surround or fully surround the body of the sheath 40.

Included in FIG. 32 is a donut 3202, which exists about the sheath 40. While shown and described as a donut 3202, it is understood that any type of slidable depth marker may be used and perform the same functions as the donut 3202. The donut 3202 may be slidably coupled to the sheath 40, permitting a user to move the donut 3202 to a desired location along the sheath 40. For example, the donut 3202 may be placed on the sheath 40 at a distance from the distal end of the sheath 40 such that the distance represents the distance to a deep venous system in the patient. This could indicate to an operator that once the donut 3202 has reached the insertion point of the patient, the catheter 15, if inserted any further, may enter the patient's deep venous system or other vasculature not intended for treatment.

Additionally, or alternatively, the donut 3202 may be sized such that it cannot enter the insertion point of the patient. As described in the previous paragraph, this may prevent the catheter 15 from accessing the deep venous system of the patient. This may also prove utilitarian during a procedure, such as segmental mechanical or mechanochemical ablation as described throughout the present specification. For example, once an operator has reached a target treatment segment 55 and started rotating the wire 30, perhaps through providing power to a motor, the operator may be able to slide the donut 3202 along the sheath 40 up to the insertion point and then release the catheter 15.

The donut 3202 may hold the catheter 15 in place relative to the insertion point, allowing the operator free use of both of their hands. In some examples, a rotation of the wire 30 attempts to draw the catheter 15 further into the body of the patient due to forward propulsion from the spinning motion. In such examples, the donut 3202 is sized such that when the donut 3202 is coupled to the sheath 40, the donut 3202 holds its position with respect to the sheath 40 due to frictional forces between the donut 3202 and the sheath 40. However, the donut 3202 is still configured to slide with respect to the sheath 40 under the influence of outside forces, such as manual manipulation by an operator that overcomes any frictional forces between the donut 3202 and the sheath 40.

Because the donut 3202 may be sized such that it cannot enter the insertion point in the body of a patient, the donut 3202 may thereby prevent the sheath 40 from further entering the vasculature of the patient. In other examples, a catheter clamp may be included to serve a similar purpose.

Also seen in FIG. 32 are a plurality of distance markings 3204 along the sheath 40. The distance markings 3204 may be used by an operator to determine how far the catheter 15 is within the patient. This is particularly useful in cases involving the withdrawal of the catheter 15. For example, during segmental mechanical or mechanochemical ablation, an operator may treat a treatment segment 55 and then begin withdrawing the catheter 15 from the patient until it reaches a subsequent treatment segment 55. In this scenario, if the first treatment segment 55 is reached and aligned with a distance marking 3204, the operator may then, after treating the treatment segment 55, withdraw the catheter 15 until a subsequent distance marking 3204 has been reached, indicating that a subsequent treatment segment 55 has been reached as well.

For this reason, it may be beneficial to include distance markings 3204 that are approximately the same length as the treatment segment 55. As disclosed previously in this disclosure, the treatment segment 55 may be the same length as the distal wire end 1204. Thus, the distance markings 3204 may also be the same length as the distal wire end 1204. However, neither of these distance marking lengths is strictly necessary, and variations in the distance may be used as desired by the user.

Finally, FIG. 32 also shows a warning track 3206 distal of the distance markings 3204. This warning track 3206 may appear as a series of closely spaced markings, but other markings or indicators may be used as well. In practice, the warning track 3206 may indicate to an operator that the end of a workable treatment length has been reached, meaning that pulling the catheter 15 any further from the patient would result in ineffective treatment.

The length of the warning track 3206, position of the warning track 3206, as well as the number of distance markings 3204 and distance between distance markings 3204 is customizable, and multiple catheters 15 may be utilized for specific purposes—such as longer or shorter lengths of treatment. Likewise, the length of the distal wire end 1204 may be customizable in order to increase or decrease the length of the treatment segment 55.

It is understood that the donut 3202, the distance markings 3204, and the warning track 3206 as shown in FIG. 32 may be used together, separately, or in any combination with one another. It is additionally understood that the donut 3202, the distance markings 3204, and the warning track 3206 as shown in FIG. 32 may be used in combination with any of the various wire 30 examples as shown and described previously in FIGS. 12A, 12B, 12C, 14, 15, 16, 17, 18, 19, 20, 21, 22A, 22B, 22C, 23A, 24A, and 25A, as well as any additional wire not specifically illustrated herein.

Figure 33:
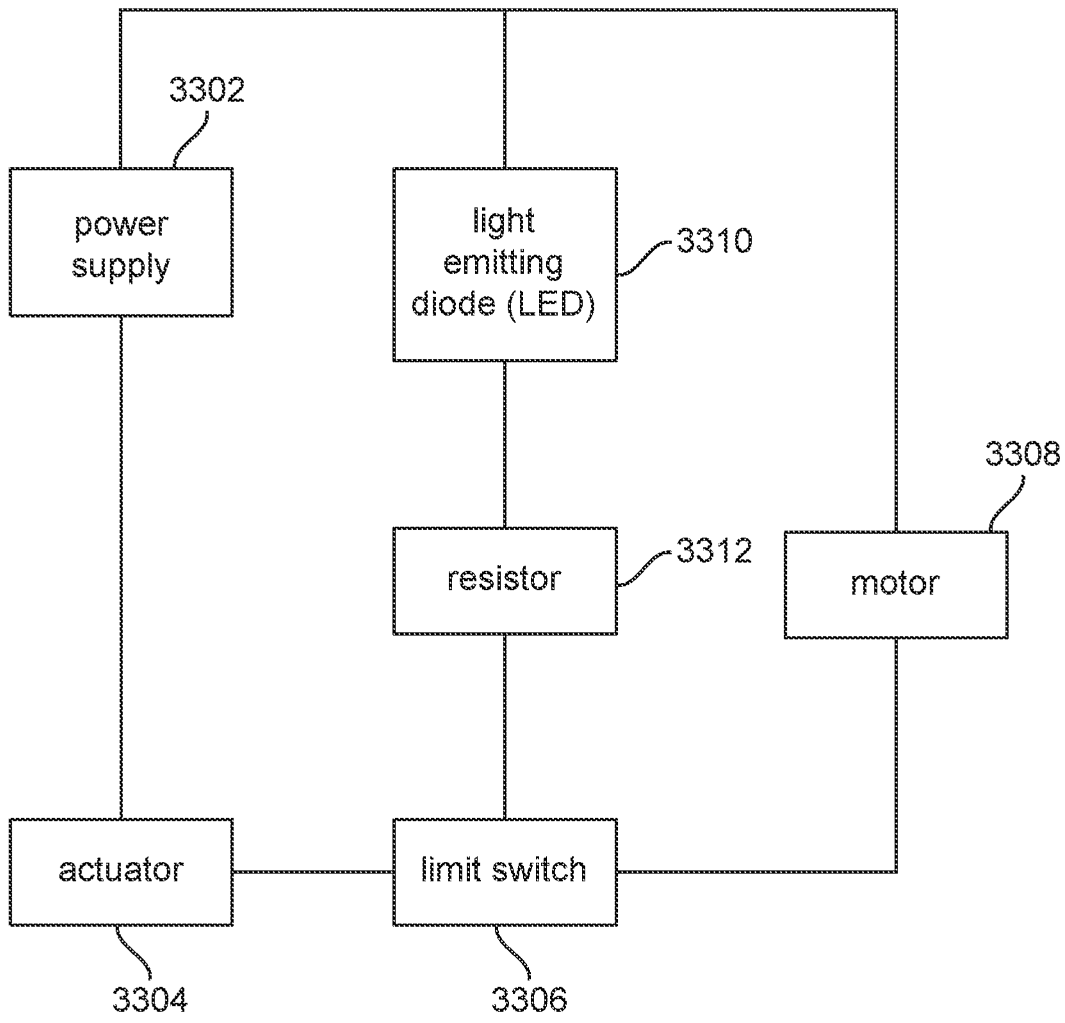
FIG. 33 illustrates an example block diagram for providing power to a motor through a limit switch.

FIG. 33 illustrates an example block diagram for operating a controller 20, perhaps any of the controllers 20 as shown and described in FIGS. 5A, 5B, 5C, 7, 8, 9A, 9B, and/or 9C. As seen in this block diagram, a power supply 3302 may be wired to receive an input from an actuator 3304. As described previously, the power supply 3302 may be a contained power supply, such as a battery or wired power. Similarly, the actuator 3304 may be a button, a switch, or anything capable of receiving a user input to operate the controller 20.

The actuator is wired to a limit switch 3306, which in turn is wired to a motor 3308 and an LED 3310 (separated by a resistor 3312 in order to receive the correct amount of power). The limit switch 3306 either permits power to flow to the motor 3308 and the LED 3310 or prevents power from flowing to the motor 3308 and the LED 3310.

For example, considering an ablation system 10, including a controller 20 with a sheath 40 and a wire 30 disposed through a working lumen of the sheath 40. If the controller 20 is capable of moving the sheath, such that retracting the sheath 40 exposes the wire 30, and extending the sheath 40 encloses the wire 30, it may be desired to prevent the wire from turning unless the wire 30 is fully exposed from the sheath 40.

In such an example, the limit switch 3306 may be provided to only permit power to the motor 3308 and the LED 3310 when the sheath 40 is fully retracted. Similarly, if the sheath 40 is extended at all from its fully retracted state, the limit switch 3306 may prevent power from being provided to the motor 3308 and the LED 3310.

This is only one example of how a limit switch 3306 may be implemented into the circuitry of a controller 20 in order to effectuate control over when the motor 3308 receives power, and any implementation of the limit switch 3306 may be implemented as desired by the user. Also, as shown and described in FIGS. 9A and 9C, the LED 3310 may be present in order to communicate to the operator that the motor is on, or that the motor is ready to be turned on (i.e., in the example above, that the sheath 40 is fully retracted). Other purposes of the LED 3310, such as for use as a timer or indicator of treatment completion during segmental mechanical or mechanochemical ablation may be realized as well through this limit switch.

It is understood that the entirety of the block diagram as shown in FIG. 33, as well as other example wiring configurations for a circuit, may be used in combination with any of the various controller 20 examples as shown and described previously in FIGS. 5A, 5B, 5C, 7, 8, 9A, 9B, and 9C, as well as any additional controller not specifically illustrated herein.

Figure 34:
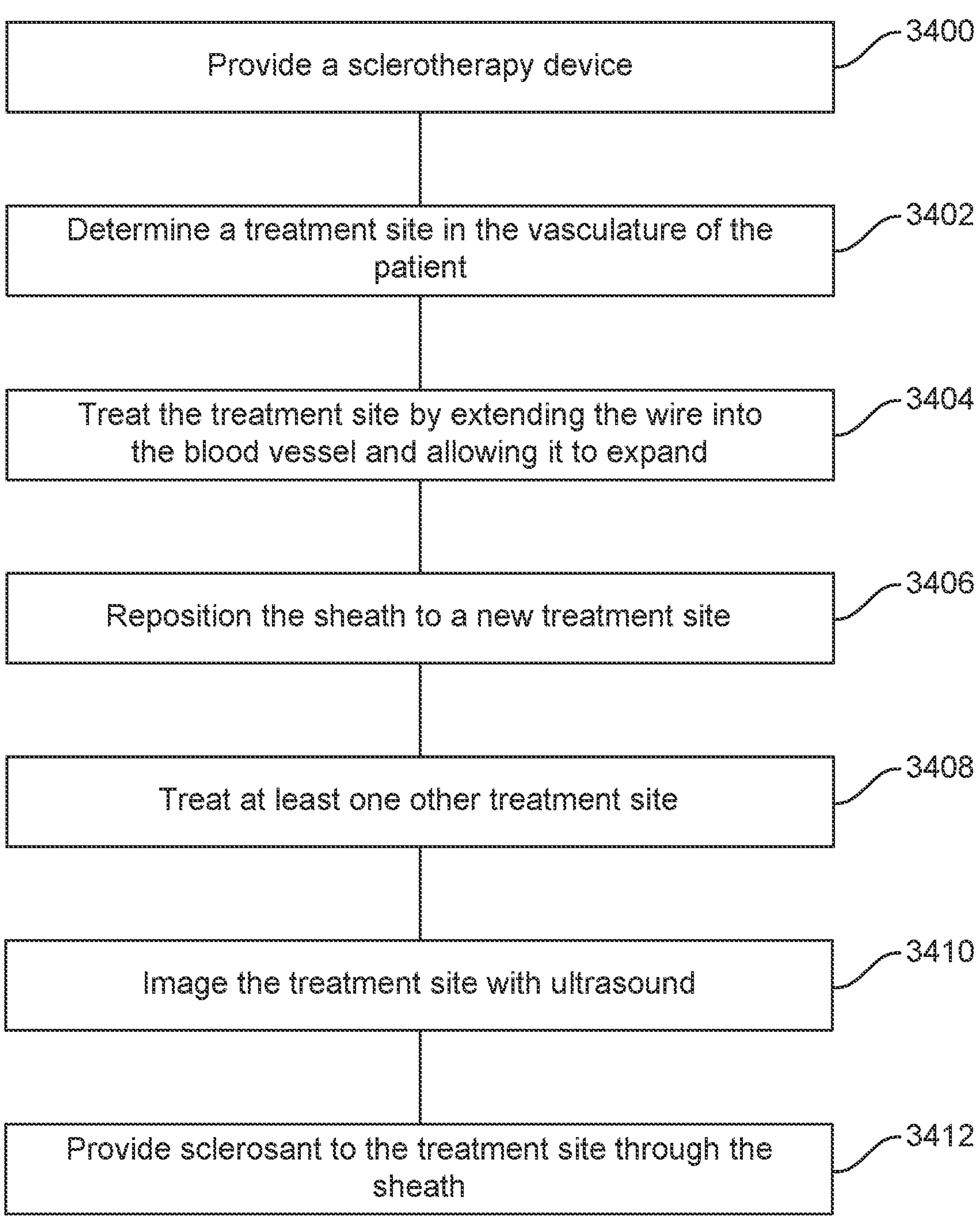
FIG. 34 illustrates a flowchart depicting an example method of treating a venous disease with an ablation system.

FIG. 34 illustrates a flowchart depicting an example method of treating a venous disease with an ablation system. In some examples, the method includes using a sclerotherapy device (at step 3400). The sclerotherapy device is understood to be any ablation device 10 and/or combination of controller 20 and catheter 15 (or sheath 40 and wire 30). As used throughout, a sclerotherapy device need not be capable of specifically delivering sclerosant, and any system which is capable of causing mechanical or mechanochemical ablation of a vessel is considered synonymous with this use of "sclerotherapy device."

According to some examples, the method includes determining a first treatment site 50 in the vasculature of the patient (at step 3402). As discussed previously, the treatment site 50 (or first treatment site 50) may be a length along a vessel, otherwise described as a treatment segment 55 (or first treatment segment 55 as in this specific example).

The method may include treating the first treatment site 50 by extending the wire 30 into the blood vessel and allowing it to expand (at step 3404). As also described previously, the distal end of the wire 30 for treating each treatment site 50 may be the length of the segment being treated (the treatment segment 55), thus permitting the wire 30 to treat (or abrade) each treatment segment 55 at once.

In some examples, the method includes repositioning the sheath to a second treatment site 50 (at step 3406). In examples as described above, the second treatment site 50 may likewise be a length along a vessel, otherwise described as a treatment segment 55 (or second treatment segment 55).

According to some examples, the method includes treating the second treatment site 50 (at step 3408). As also detailed above, the distal end of the wire 30 for treating each treatment site 50 may be the length of the segment being treated, thus permitting the wire 30 to treat (or abrade) the entirety of the second treatment segment 55 at once. The use of "first" and "second" is for example only, and more steps or stages of treatment may be present. In these examples, any next step could be considered to be performed on a subsequent treatment site 50 or treatment segment 55.

The method may include imaging the treatment 50 with ultrasound (at step 3410). This is but one method of locating the catheter 15 within the patient while delivering the catheter to a treatment site 50, or retracting the catheter 15 at least partially to locate the catheter 15 at a subsequent treatment site 50.

In some examples, the method includes providing sclerosant through a sheath 40 to at least one of the first treatment site 50 and the second treatment site 50 (at step 3412). The sclerosant could be any drug, and could be delivered through means other than the sheath 40, such as through a lumen of the catheter 15 and/or a lumen of the wire 30. When delivered through the sheath 40, the drug may pass through a working lumen within the sheath 40.

Additionally, according to some examples, the drug is not delivered while the catheter 15 (sheath 40) is removed from the first treatment site 50 and relocated to the second treatment site 50, permitting the operator to worry about one less thing in that they no longer need to inject the drug at a specific rate while simultaneously withdrawing the catheter 15 at a specific rate. In this way, the method achieves segmental mechanical or mechanochemical ablation. It should be appreciated that stating segmental mechanical or mechanochemical ablation means segmental mechanical or segmental mechanochemical ablation.

Figure 35:
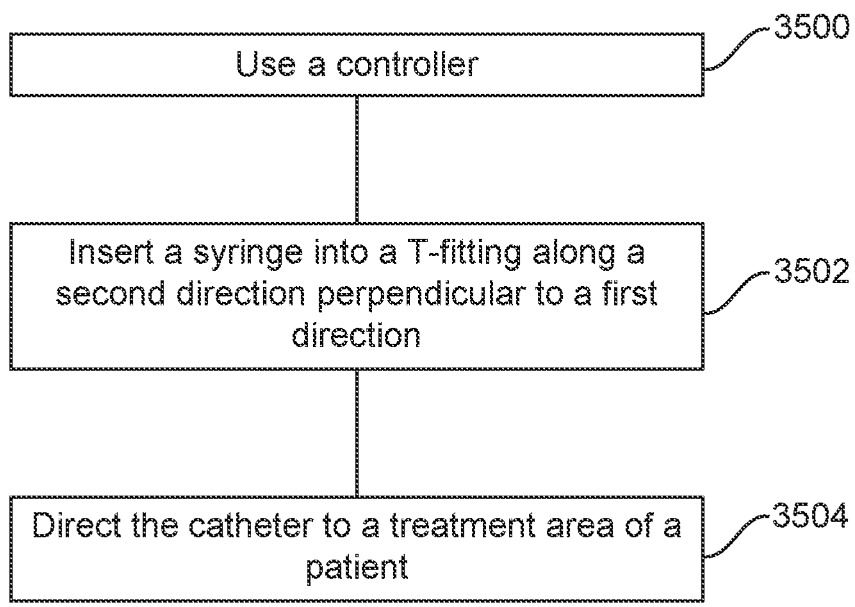
FIG. 35 illustrates a flow chart depicting a method of controlling a catheter, according to some examples.

FIG. 35 illustrates a flow chart depicting an example method of controlling a catheter. In some examples, the method of controlling a catheter includes using a controller (at step 3500). This controller may be the controller illustrated in FIGS. 5A, 5B, 5C, 7, 8, 9A, 9B, and 9C, or it may be a similar controller including a sliding portion capable of receiving a syringe. According to some examples, the method of controlling a catheter includes inserting a syringe into a T-fitting along a second direction perpendicular to a first direction (at step 3502).

The first direction is expressed in FIGS. 7, 8, 9A, 9B, and 9C as first direction 712, first direction 810, and first direction 916, respectively, but to reiterate, it is the direction of lateral travel of the saddle and T-fitting about the device body. Expressed another way, the first direction is the direction of travel between the proximal body end and the distal body end. In step 3502, the syringe is inserted into a T-fitting along a direction perpendicular to the first direction. Because the invention exists in three-dimensional space, it is understood that this second direction could be any direction circumferentially about the first direction. Additionally, as expressed in FIGS. 7, 8, 9A, 9B, and 9C, perfectly perpendicular insertion of the syringe is not necessary, and other directions and/or angles of insertion of the syringe into the T-fitting may also be used.

The method of controlling a catheter may include directing the catheter to a treatment site of a patient (at step 3504). In examples including a catheter coupled to the distal body end, and once the syringe has been inserted into the T-fitting, the catheter may be supplied to the treatment site for a procedure to begin.

Figure 36:
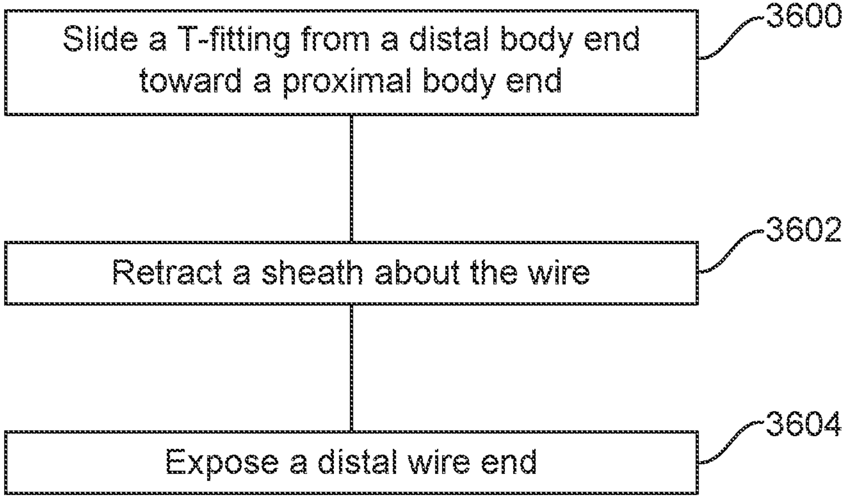
FIG. 36 illustrates a flow chart depicting a method of exposing a wire from a catheter, according to some examples.

FIG. 36 illustrates a flow chart depicting a method of exposing a wire from a catheter, according to some examples. In some examples, the method of exposing a wire from a catheter includes sliding a T-fitting from a distal body end toward a proximal body end (at step 3600). In examples including a catheter, the catheter may be coupled to the device body at the distal body end. By sliding the saddle and the T-fitting from the distal body end to the proximal body end, the catheter is effectively "pulled back" along with the movement of the saddle and the T-fitting.

According to some examples, the method of exposing a wire from a catheter includes retracting a sheath about the wire (at step 3602). In examples including a wire within the catheter body, when the catheter is pulled back in response to the movement of the saddle and the T-fitting, as expressed in step 3600, the catheter sheath surrounding the wire moves about the wire. The wire either does not move in response to the movement of the saddle and the T-fitting, or moves at a rate that is lower than that of the catheter.

The method of exposing a wire from a catheter may include exposing a distal wire end (at step 3604). Once the saddle and the T-fitting have moved all the way from the distal body end to the proximal body end, the wire may be exposed from the catheter sheath, permitting contact between the wire and the walls of the vasculature. This permits the wire to be used during a procedure, while also allowing the wire to be delivered to the treatment site while not exposed.

Figure 37:
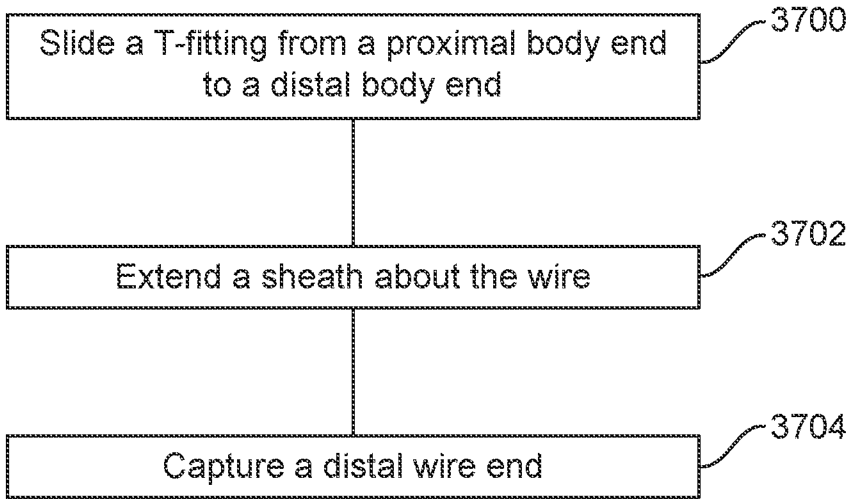
FIG. 37 illustrates a flow chart depicting an example method of capturing a wire into a catheter.

FIG. 37 illustrates a flow chart depicting an example method of capturing a wire into a catheter. In some examples, the method of capturing a wire with a catheter includes sliding a T-fitting from a proximal body end to a distal body end (at step 3700). In examples including a catheter, the catheter may be coupled to the device body at the distal body end. By sliding the saddle and the T-fitting from the proximal body end to the distal body end, the catheter is effectively "pushed forward" along with the movement of the saddle and the T-fitting.

According to some examples, the method of capturing a wire with a catheter includes extending a sheath about the wire (at step 3702). In examples including a wire within the catheter body, when the catheter is pushed forward in response to the movement of the saddle and the T-fitting, as expressed in step 3700, the catheter sheath surrounding the wire moves about the wire. The wire either does not move in response to the movement of the saddle and the T-fitting, or moves at a rate that is lower than that of the catheter.

The method of capturing a wire with a catheter may include capturing a distal wire end (at step 3704). Once the saddle and the T-fitting have moved all the way from the proximal body end to the distal body end, the catheter sheath may completely cover the wire, effectively capturing, or enclosing, the distal wire end into the catheter sheath. Once a procedure is completed, this may facilitate the prevention of damage to non-treatment areas.

Figure 38:
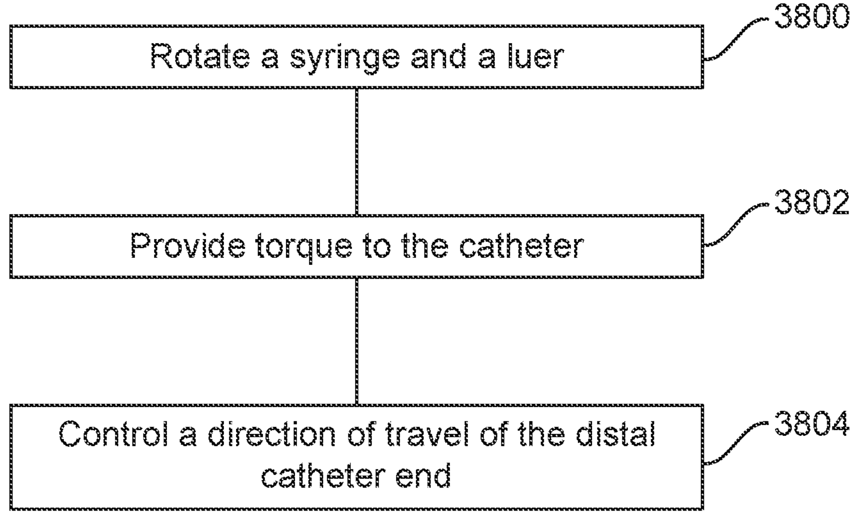
FIG. 38 illustrates a flow chart depicting a method of controlling a distal catheter end, according to some examples.

FIG. 38 illustrates a flow chart depicting a method of controlling a distal catheter end, according to some examples. In some examples, the method of controlling a distal catheter end includes rotating a syringe and a luer (at step 3800). By rotating the syringe and luer, a rotational movement may also be applied to a catheter coupled to the device body.

According to some examples, the method of controlling a distal catheter end includes providing torque to a catheter (at step 3802). The rotational movement of the syringe and luer may apply a torque to the catheter, and this torque may either be in the direction of rotation of the syringe and luer, or opposite the direction of rotation of the syringe and luer.

The method of controlling a distal catheter end may include controlling a direction of travel of the distal catheter end (at step 3804). In response to the applied torque, the distal catheter end moves. For example, if the torque applied to the catheter is in the same direction of rotation as the syringe and luer, and this direction of rotation is clockwise about the body of the device, the distal catheter end may be steered toward the left (wherein the length of the catheter from the proximal catheter end to the distal catheter end is a first direction, the left being based upon this first direction). Contra, if the torque applied to the catheter is opposite the direction of rotation of the syringe and the luer, the distal catheter end may be steered toward the right. The use of "left" and "right" is for example only, and it is understood that the device may be set up to apply torque to the catheter in such a way as to control the distal catheter end in any direction as desired by the operator.

Figure 39:
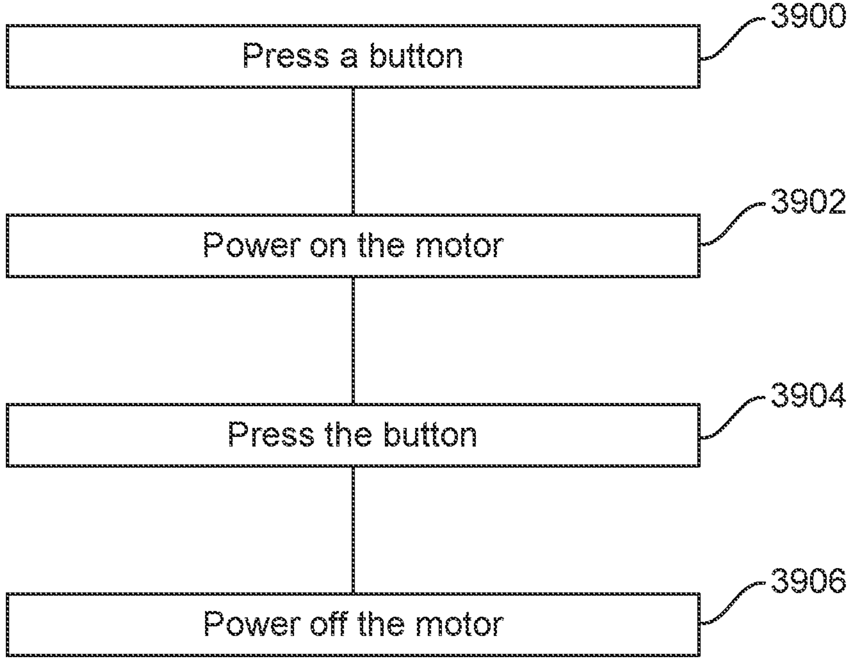
FIG. 39 illustrates a flow chart depicting a method of controlling a motor, according to some examples.

FIG. 39 illustrates a flow chart depicting an example method of controlling a motor. In some examples, the method of controlling a motor includes pressing a button (at step 3900). The button may be mechanically coupled to the device body, and electrically coupled to the motor, thereby allowing control of the motor. According to some examples, the method of controlling a motor includes powering on the motor (at step 3902). In response to actuation of the button, power is supplied to the motor, thereby allowing the motor to rotate.

The method of controlling a motor may include pressing the button (at step 3904). Once a procedure is completed, or at any time it is desired to no longer have the motor rotate, the button may be actuated again. In some examples, the method of controlling a motor includes powering off the motor (at step 3906). Once the button is actuated a subsequent time, or any time that the motor is currently powered on, the button will remove access to the power from the motor, thus stopping the motor from rotating. While the use of "button" is used in FIG. 39, it is understood that any toggleable mechanism, or "actuator" as described and shown in the previous figures (see FIGS. 5A, 5B, 5C, 6A, 6B, 9A, 9B, and 9C), such as a switch, can be used to supply or remove power from the motor.

Figure 40:
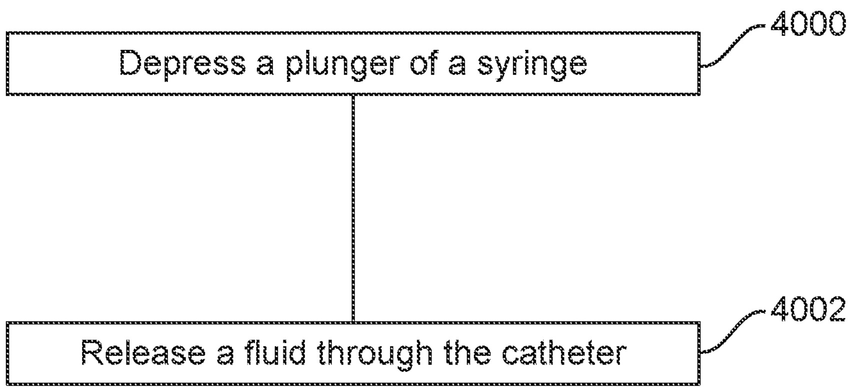
FIG. 40 illustrates a flow chart depicting a method of providing a fluid through a catheter, according to some examples.

FIG. 40 illustrates a flow chart depicting a method of providing a fluid through a catheter, according to some examples. In some examples, the method of providing a fluid through a catheter includes depressing a plunger of a syringe (at step 4000). Through depressing the plunger of the syringe, any fluid within the syringe is ejected from the opening in the tip of the syringe.

According to some examples, the method of providing a fluid through a catheter includes releasing a fluid through the catheter (at step 4002). In examples where a catheter is in fluid communication with the syringe, the fluid ejected from the syringe in step 4000 is injected into the catheter body, perhaps through a fluid lumen. This allows the fluid to travel the length of the catheter, and to a treatment site.

Figure 41:
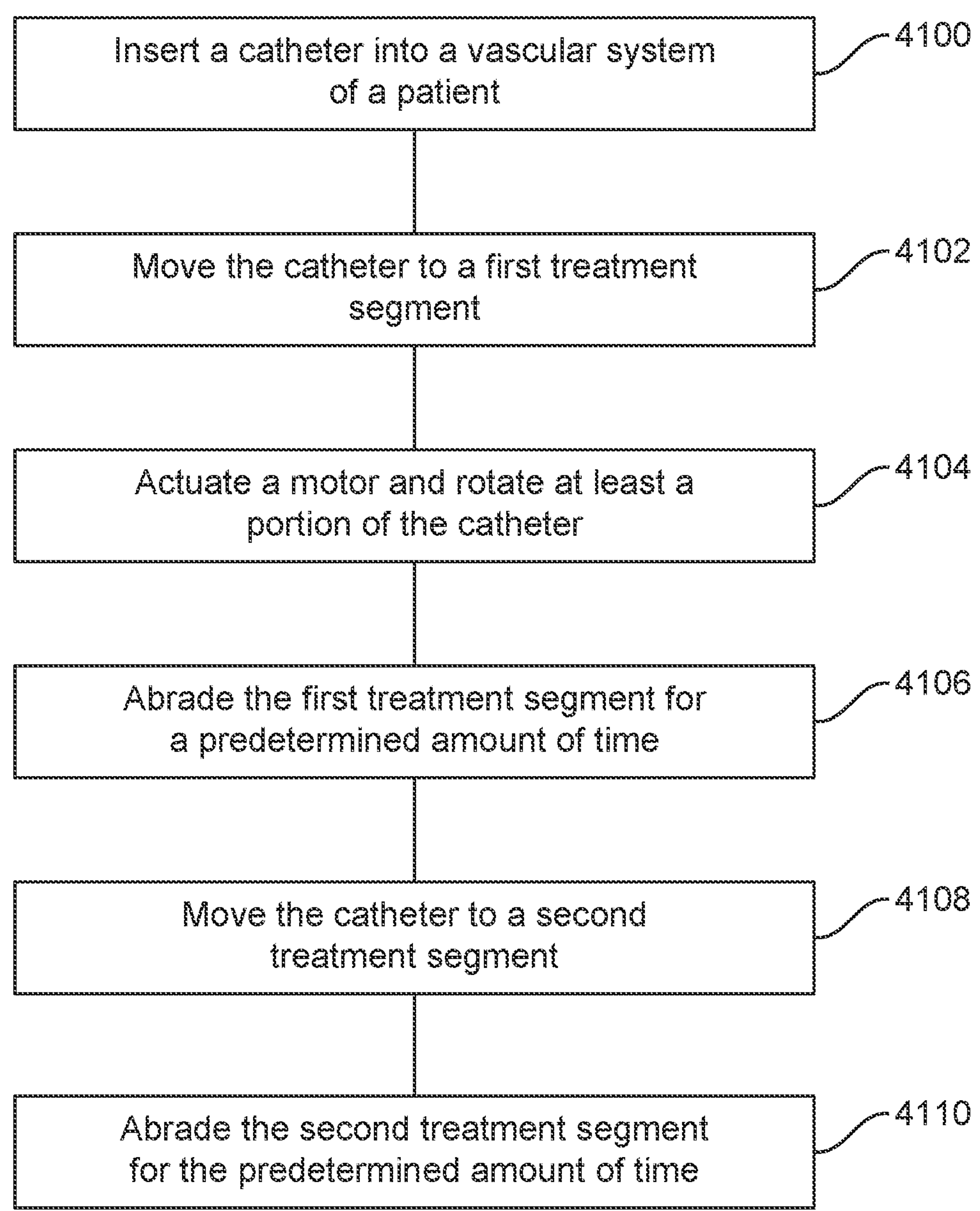
FIG. 41 illustrates a flow chart depicting a method of segmental mechanical ablation, according to some examples.

FIG. 41 illustrates a flow chart depicting a method of segmental mechanical ablation, according to some examples. In some examples, the method of segmental mechanical ablation includes inserting a catheter into a vascular system of a patient (at step 4100). The catheter may then be delivered to a treatment site, also referred to as a treatment segment due to the length of treatment provided without necessitating movement of the catheter. According to some examples, the method of segmental mechanical ablation includes moving the catheter to a first treatment segment (at step 4102). The first treatment segment may be the distal most location in an overall treatment length, permitting an operator to move the catheter through the overall treatment length by pulling the catheter out from the patient, rather than pushing the catheter further into the patient. However, it is understood that either direction of movement is enabled by this method, and the operator can choose how to perform such a segmental ablation treatment.

The method of segmental mechanical ablation may include actuating a motor and rotating at least a portion of the catheter (at step 4104). The mechanical agitation (or abrasion, or ablation) of the vessel wall may be due to rotating the catheter and having portions of the catheter physically contact the intima and media of the vessel wall. This contact may be enough to damage these layers, and in some instances, this damage may be enough to kill the vessel, thus completing treatment of a varicose vein at least in this treatment segment. In other examples, the catheter makes a motion that is less rotational and more reciprocating, thereby "scratching" the vessel walls in order to perform this damage. This reciprocating motion may either be caused through conversion of rotational motion of the motor into linear motion of the catheter, or by other means if desired.

In some examples, the method of segmental mechanical ablation includes abrading the first treatment segment for a predetermined amount of time (at step 4106). The predetermined amount of time is dependent on the needs of the operator, and what length of time may be necessitated by the specific vessel being treated. The length of time may also change based on whether the procedure is segmental mechanical ablation, as described in the method of FIG. 41, or segmental mechanochemical ablation, as will be discussed in FIG. 45. In the case of segmental mechanical ablation, the catheter may be left within the treatment segment (unmoving longitudinally through the vein) for about five to about thirty seconds. Again, these numbers are by example only, and an operator could choose to leave the catheter within the treatment segment for whatever length of time they so desire.

According to some examples, the method of segmental mechanical ablation includes moving the catheter to a second treatment segment (at step 4108). This second treatment segment may be adjacent, or approximately adjacent, to the first treatment segment, however, this is not strictly necessary. By having the second treatment segment near or adjacent to the first treatment segment, an operator can be sure that the entirety of the vessel is being treated.

The method of segmental mechanical ablation may include abrading the second treatment segment for the predetermined amount of time (at step 4110). This abrasion (or, again, agitation or ablation) may be performed in the same manner as described above in step 4106. The predetermined amount of time may be same as the predetermined amount of time as discussed in step 4106, or it may be a different predetermined amount of time, depending on the needs of the operator for a specific segment of a vein being treated.

Figure 42:
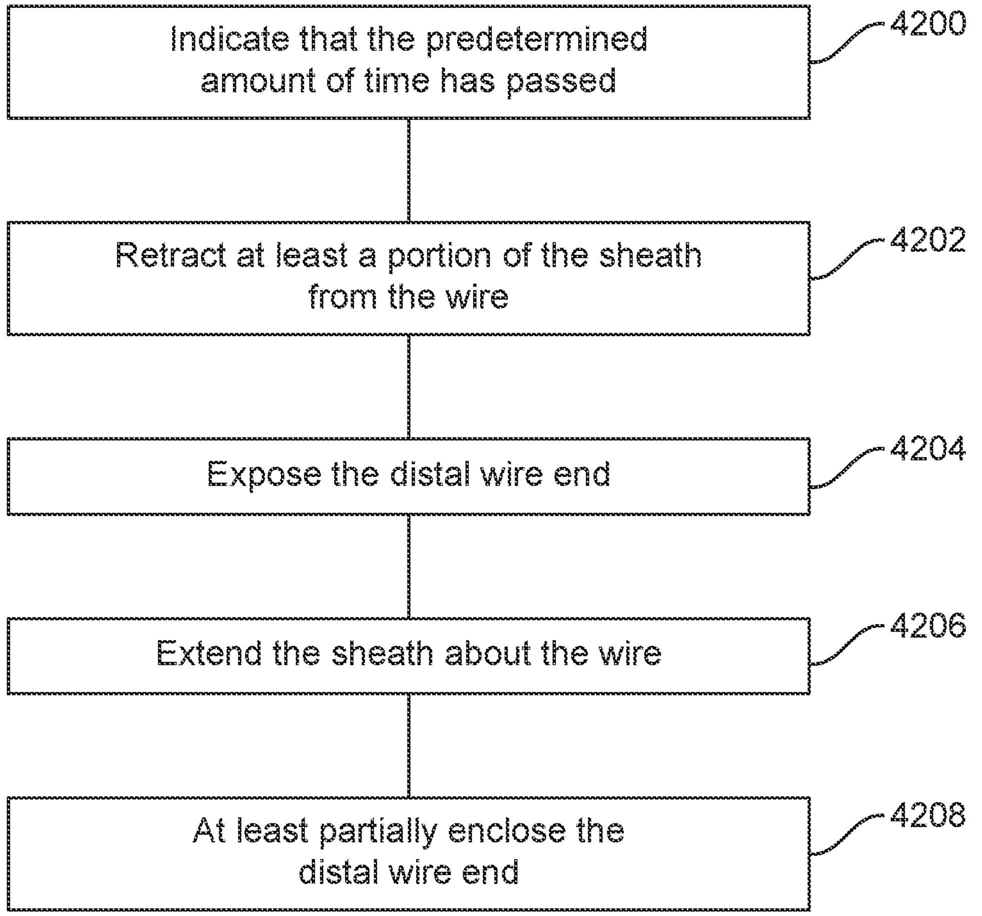
FIG. 42 illustrates a flow chart depicting a method of exposing and enclosing a wire in a sheath, according to some examples.

FIG. 42 illustrates a flow chart depicting a method of exposing and enclosing a wire in a sheath, according to some examples. In some examples, the method of exposing and enclosing a wire in a sheath includes indicating that the predetermined amount of time has passed (at step 4200). This indication step is not strictly limited to methods of exposing and enclosing a wire in a sheath, and may be present in any of the other methods listed herein, or not included in the present method if this indication step is not desired. This indication may occur through a component, likely located extracorporeally, perhaps on the controller, such as an LED, a speaker, or a display. The indication may be audible or visual.

According to some examples, the method of exposing and enclosing a wire in a sheath includes retracting at least a portion of the sheath from the wire (at step 4202). The wire, which may be passed through a working lumen of the sheath, may additionally be slidably disposed within the sheath. In some examples, this permits the sheath to be retracted about the wire.

The method of exposing and enclosing a wire in a sheath may include exposing the distal wire end (at step 4204). Once the sheath is retracted, a portion of the wire, in this example the distal wire end, may be exposed from the sheath, permitting the distal wire end to make contact with the walls of a vessel in treatments such as segmental mechanical ablation.

In some examples, the method of exposing and enclosing a wire in a sheath includes extending the sheath about the wire (at step 4206). By slidably moving the sheath opposite the direction of step 4202, an operator may extend the sheath back about the wire, all the way to its initial position, or at least partially. This may prove useful in examples where the operator desires a different length of the distal wire end to treat a specific length of vessel.

According to some examples, the method of exposing and enclosing a wire in a sheath includes at least partially enclosing the distal wire end (at step 4208). Through extending the sheath, the operator may enclose the distal wire end once again, facilitating safe removal of the catheter from the patient. Again, as the sheath may only be partially extended about the wire, the distal wire end may be only partially enclosed by the sheath. If the sheath is extended all the way back to its initial position, the wire may be entirely enclosed once again.

Figure 43:
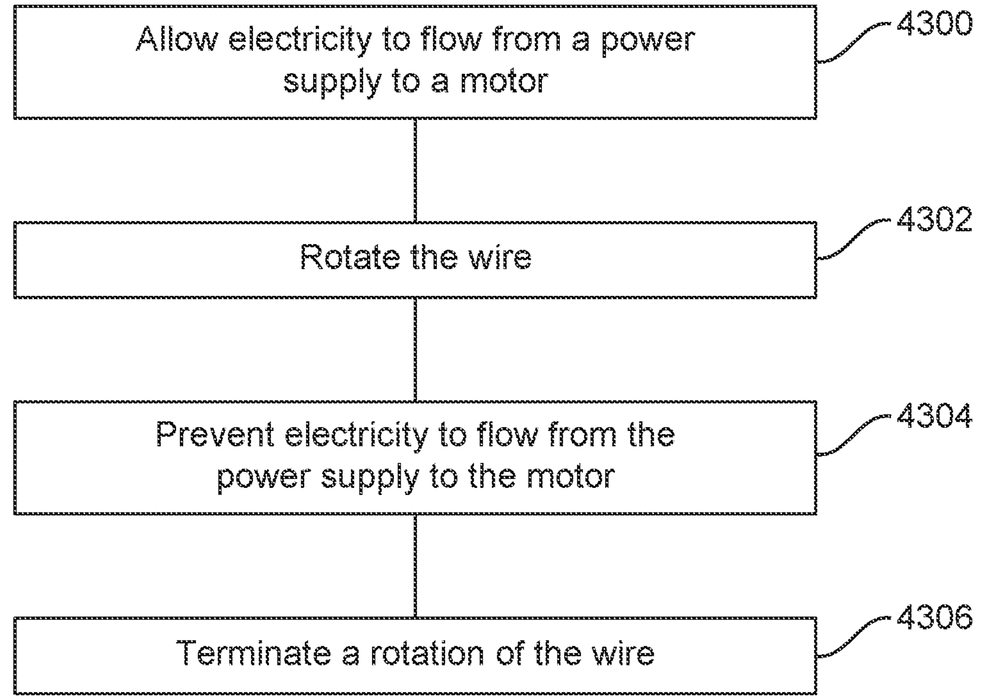
FIG. 43 illustrates a flow chart depicting a method of limiting power flow to a motor, according to some examples.

FIG. 43 illustrates a flow chart depicting a method of limiting power flow to a motor, according to some examples. The method of limiting power flow to a motor may include allowing electricity to flow from a power supply to a motor (at step 4300). In examples including a limit switch, the limit switch may be the component by which the electricity is either allowed to or prevented from flowing. As will be described in more detail in FIG. 47, the limit switch may be controlled by some other property of the ablation system as a whole.

In some examples, the method of limiting power flow to a motor includes rotating the wire (at step 4302). As explored in FIG. 41, the rotation of the wire may be what causes the ablation (or agitation, or abrasion) of the vessel wall. The rotation of the motor may also be translated in the longitudinal movement of the wire, permitting a scratching effect rather than rotational ablation.

According to some examples, the method of limiting power flow to a motor includes preventing electricity to flow from the power supply to the motor (at step 4304). As described in step 4300, this may be accomplished through the use of a limit switch. The method of limiting power flow to a motor may include terminating a rotation of the wire (at step 4306). Once electricity is no longer permitted to flow to the motor, any effects the motor has on the movement of the wire may stop.

Figure 44:
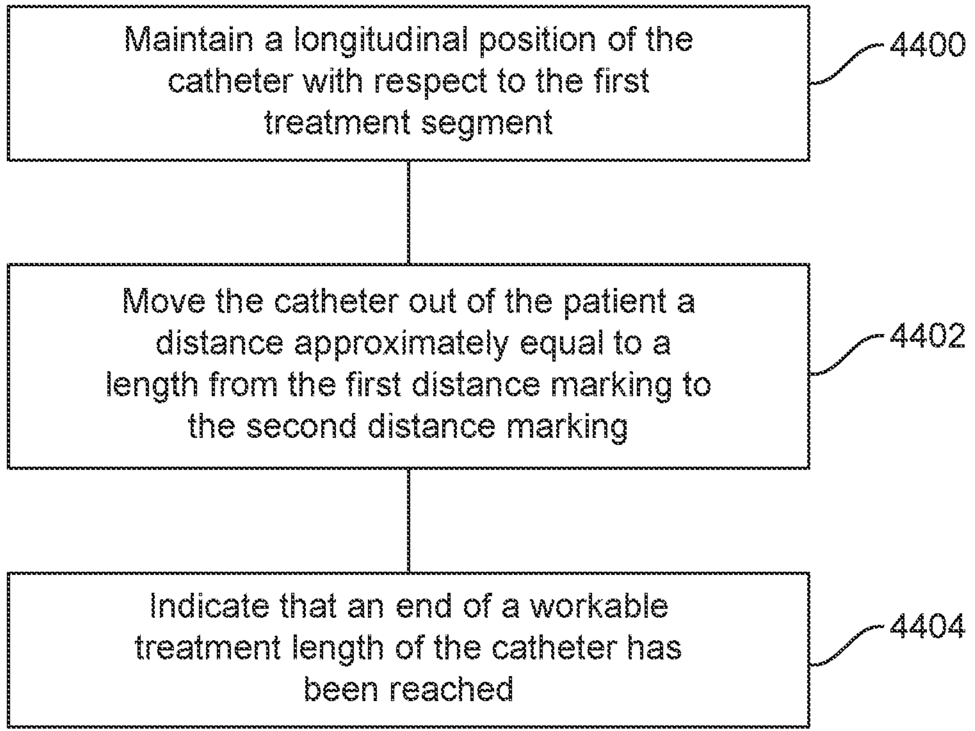
FIG. 44 illustrates a flow chart depicting a method of gauging distances in a segmental treatment, according to some examples.

FIG. 44 illustrates a flow chart depicting a method of gauging distances in a segmental treatment, according to some examples. In some examples, the method of gauging distances in a segmental treatment includes maintaining a longitudinal position of the catheter with respect to the first treatment segment (at step 4400). As described in FIG. 41, the catheter may be kept in place longitudinally within a vessel for a predetermined amount of time. In some examples, a shape of the distal wire end permits the entirety of a segment to be treated at once, thus the catheter does not need to be moved while such a segment is being treated. This may permit an operator to keep track of one less thing at a time, and free up one of the operator's hands to assist with other portions of the procedure.

According to some examples, the method of gauging distances in a segmental treatment includes moving the catheter out of the patient a distance approximately equal to a length from the first distance marking to the second distance marking (at step 4402). These distance marking may be located on a shaft of the catheter. As the catheter is withdrawn from the body of the patient, subsequent distance markings may become visible, indicating to an operator how far the catheter as a whole has been removed from the patient. In some examples, the distance markings are separated by a distance approximately equal to the length of the treatment segment. In such examples, an operator pulling the catheter out from the body of the patient would be able to identify when the distal end of the catheter has been moved from one treatment segment to a subsequent treatment segment. This spacing of the distance markings would additionally make it unlikely that the operator would miss a portion of the vessel to be treated, as every treatment segment would be individually treated with minimal spacing, if any, between segments.

The method of gauging distances in a segmental treatment may include indicating that an end of a workable treatment length of the catheter has been reached (at step 4404). A warning track, or similar, on the body of the catheter may indicate additional information to an operator. The warning track may be visually distinct from the distance markings of the prior paragraph in order to permit an operator to quickly discern the difference between the information being conveyed. Additionally, the warning track would likely reside on the catheter distal the distance markings. This is because, in some examples, the purpose of the warning track is to indicate that the operator is leaving the treatment area, i.e., the operator has reached the end of the catheter's workable treatment length. This may indicate to the operator that the treatment of the vessel, at least in this instant treatment, has been completed.

Figure 45:
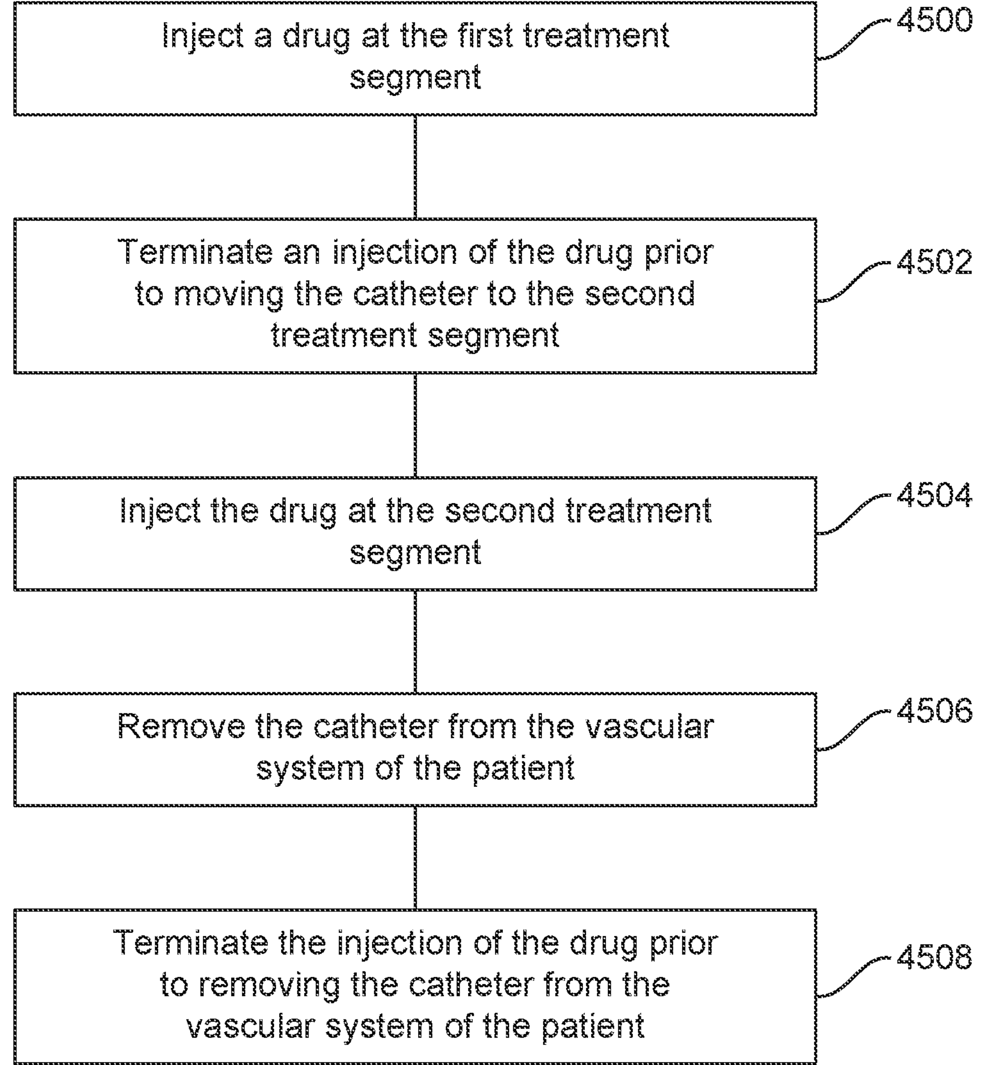
FIG. 45 illustrates a flow chart depicting a method of segmental mechanochemical ablation, according to some examples.

FIG. 45 illustrates a flow chart depicting a method of segmental mechanochemical ablation, according to some examples. According to some examples, the method of segmental mechanochemical ablation includes injecting a drug at the first treatment segment (at step 4500). Similar to the disclosure of FIG. 41, this injection may occur for a predetermined amount of time. The predetermined amount of time may be the same as the amount of time mechanical ablation is performed, or different. Additionally, the injection may occur before, after, or during the mechanical ablation portion of treatment. For example, an operator may insert the catheter to the correct location for treatment, and then power the motor to begin abrading the vessel wall with a distal wire end for five seconds. After these five seconds have passed, the operator may begin depressing a plunger of the syringe to inject the drug into the treatment site. This may be performed over a period of time such that a specific rate of drug infusion is accomplished. During this injection, the distal wire end may continue to rotate and abrade the vessel wall. This injection and mechanical ablation may occur for approximately five seconds. Once the injection has been completed, the operator may permit the distal wire end to continue mechanically ablating the vessel wall for another ten seconds, which may drive the drug further into the damaged endothelium. It is understood that the times listed here are by example only, and different times may be used for different treatments.

The method of segmental mechanochemical ablation may include terminating an injection of the drug prior to moving the catheter to the second treatment segment (at step 4502). For segmental mechanochemical ablation, the drug only needs to be injected while the catheter is placed within a treatment segment. This is dissimilar to mechanochemical ablation methods in the prior art, in which the drug must be constantly delivered while the catheter is retracted through the vasculature of the patient. Because the injection of the drug is terminated prior to moving the catheter from the first treatment segment to the second treatment segment, the operator does not need to focus their attention on the injection of the drug at the same time as the movement of the catheter. This may facilitate the elimination of human error when trying to measure two different rates—a rate of retraction and a rate of injection—at the same time.

In some examples, the method of segmental mechanochemical ablation includes injecting the drug at the second treatment segment (at step 4504). This injection may also be for a predetermined amount of time, as described in step 4500. However, the predetermined amount of time for the injection into the second treatment segment need not be the same length of time as the predetermined amount of time for the injection into the first treatment segment.

According to some examples, the method of segmental mechanochemical ablation includes removing the catheter from the vascular system of the patient (at step 4506). Once a treatment has been completed, the operator may remove the device from the patient. The method of segmental mechanochemical ablation may include terminating the injection of the drug prior to removing the catheter from the vascular system of the patient (at step 4508). After a final treatment segment has been treated, the operator may discontinue injecting any drug from the syringe through the catheter prior to removing the catheter from the patient.

Figure 46:
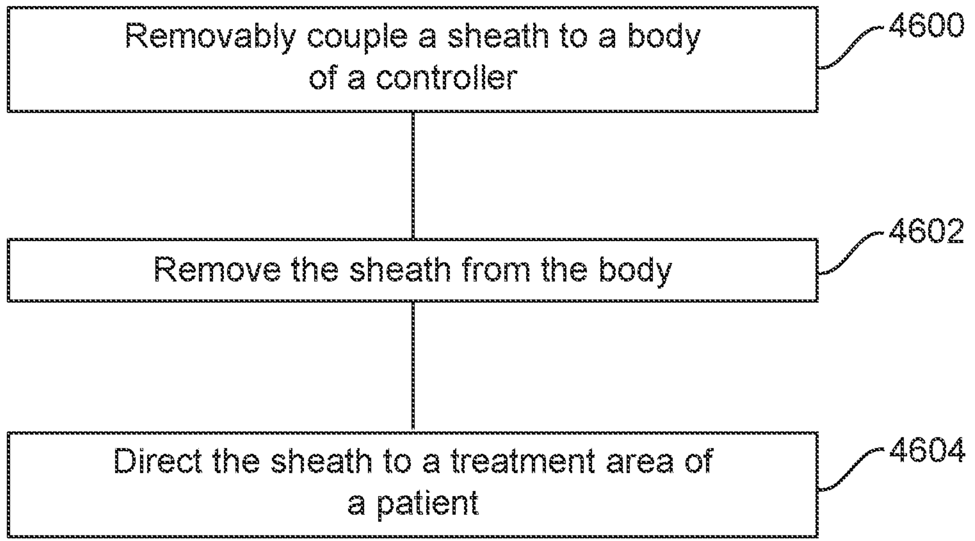
FIG. 46 illustrates a flow chart depicting a method of tracking a catheter sheath separate from a wire, according to some examples.

FIG. 46 illustrates a flow chart depicting a method of tracking a catheter sheath separate from a wire, according to some examples. In some examples, the method of tracking a catheter sheath separate from a wire includes removably coupling a sheath to a body of a controller (at step 4600). Removably coupling the sheath to the body of the controller may permit the sheath to be manipulated longitudinally distinct from the wire. According to some examples, the method of tracking a catheter sheath separate from a wire includes removing the sheath from the body (at step 4602). Because the sheath is detachably coupled to the body of the controller in this example, the sheath may be detached, or removed, from the body while leaving a wire in place (still coupled in some way to the body of the controller).

The method of tracking a catheter sheath separate from a wire may include directing the sheath to a treatment area of a patient (at step 4604). By detaching the sheath from the body of the controller while leaving the wire in place, the sheath can be delivered to a treatment site in advance of the wire. In examples where the profile of the wire is such that it affects the profile of the sheath while stored inside, even mildly, it may be desired to track the sheath to the treatment site without this addition to its crossing profile. Then, once the sheath is located at the correct position, the wire may be disposed through the sheath to also reach the treatment site.

Figure 47:
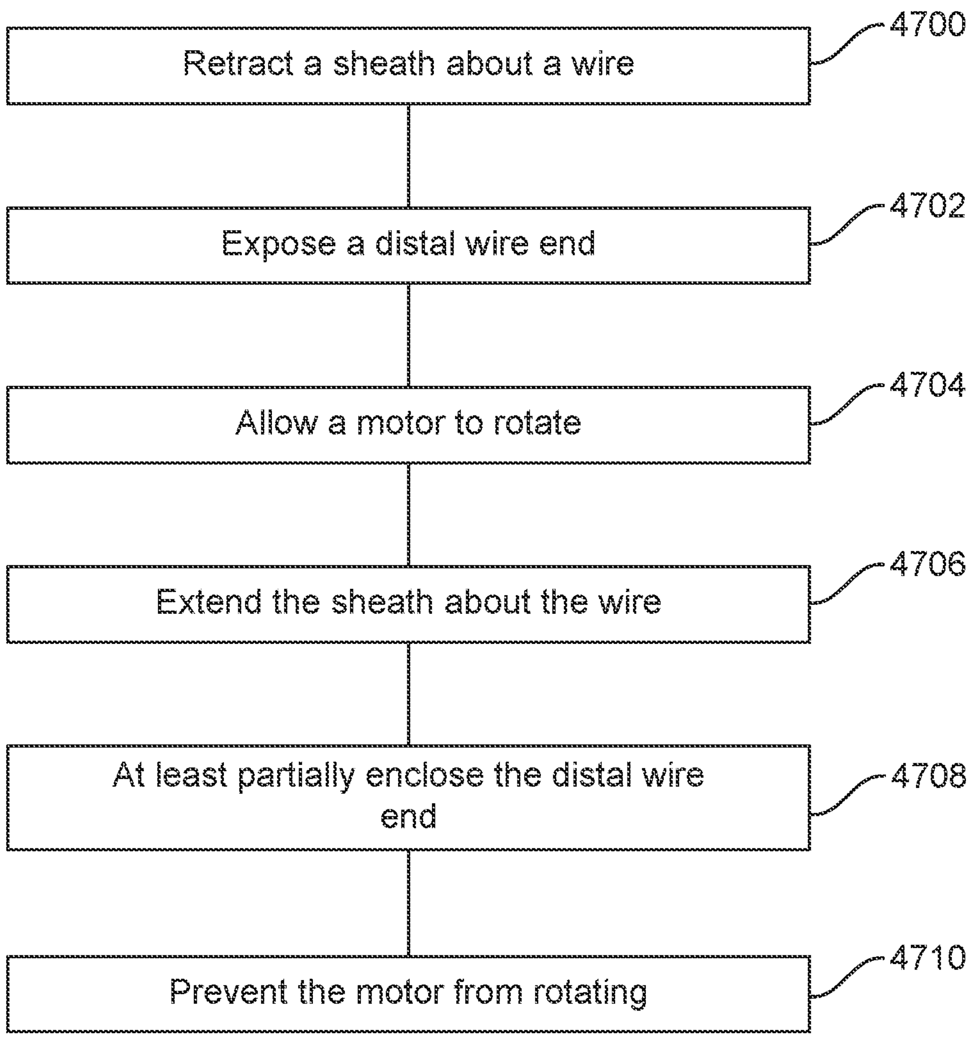
FIG. 47 illustrates a flow chart depicting an additional method of limiting power flow to a motor, according to some examples.

FIG. 47 illustrates a flow chart depicting an additional method of limiting power flow to a motor, according to some examples. In some examples, the additional method of limiting power flow to a motor includes retracting a sheath about a wire (at step 4700). This limiting feature may be performed by a limit switch, such as described in the method of FIG. 43. In such examples, the limit switch may be operatively coupled to the sheath, such that the limit switch only allows power to flow through (from the power supply, through the limit switch, to the motor) when the sheath is in a fully retracted position. In other examples, the limit switch permits power to flow from the power supply to the motor when the sheath is only partially retracted, thereby allowing for variable treatment lengths of the exposed wire. In either example, because the limit switch prevents the motor from receiving power until the sheath is retracted, or at least partially retracted, the motor cannot operate, either intentionally or unintentionally, when the wire is not exposed. This may facilitate safe delivery of the catheter to the treatment site without the concern of the wire rotating prematurely.

According to some examples, the additional method of limiting power flow to a motor includes exposing a distal wire end (at step 4702). As described previously in FIG. 42, once the sheath is retracted, a portion of the wire, in this example the distal wire end, may be exposed from the sheath, permitting the distal wire end to make contact with the walls of a vessel in treatments such as segmental mechanical ablation.

The additional method of limiting power flow to a motor may include allowing a motor to rotate (at step 4704). Once the sheath is retracted, or at least partially retracted, the limit switch may allow the motor to receive power, and thus rotate. As discussed in FIGS. 41 and 43 above, the rotation of the wire, and thus the rotation of the distal wire end, may be what causes the ablation (or agitation, or abrasion) of the vessel wall. Once again, the rotation of the motor may also be translated in the longitudinal movement of the wire, permitting a scratching effect via the distal wire end, rather than rotational ablation.

In some examples, the additional method of limiting power flow to a motor includes extending the sheath about the wire (at step 4706). By slidably moving the sheath opposite the direction of step 4700, an operator may extend the sheath back about the wire. Again, this movement may include the sheath moving all the way back to its initial position (i.e., the position the sheath may have been in when the catheter was initially delivered to the treatment site), or only partially extending the sheath about the wire. Aside from the already mentioned variable treatment length this provides, this may also impact the limit switch, thus preventing the motor from receiving any more power, as will be discussed in step 4710.

According to some examples, the additional method of limiting power flow to a motor includes at least partially enclosing the distal wire end (at step 4708). As discussed in FIG. 42 above, through extending the sheath, the operator may enclose the distal wire end once again, facilitating safe removal of the catheter from the patient. Again, as the sheath may only be partially extended about the wire, the distal wire end may be only partially enclosed by the sheath. If the sheath is extended all the way back to its initial position, the wire may be entirely enclosed once again. Additionally, as mentioned in step 4706, this enclosing of the distal wire end may also influence a limit switch to prevent power from flowing to the motor.

The additional method of limiting power flow to a motor may include preventing the motor from rotating (at step 4710). Once a procedure has been completed, and the operator wants to remove the catheter from the patient, the operator may also want to stop the ablation mechanism, be it mechanical or chemical, from occurring so as not to damage healthy veins. Beyond simply turning the motor off, by tying the position of the sheath to a limit switch, the operator may not accidentally start the motor again during this retraction of the catheter from the patient's body. Once again, the limit switch may be adjusted to permit variable length treatment segments of the distal wire end by only preventing the motor from receiving power when the sheath is fully extended.

Figure 48:
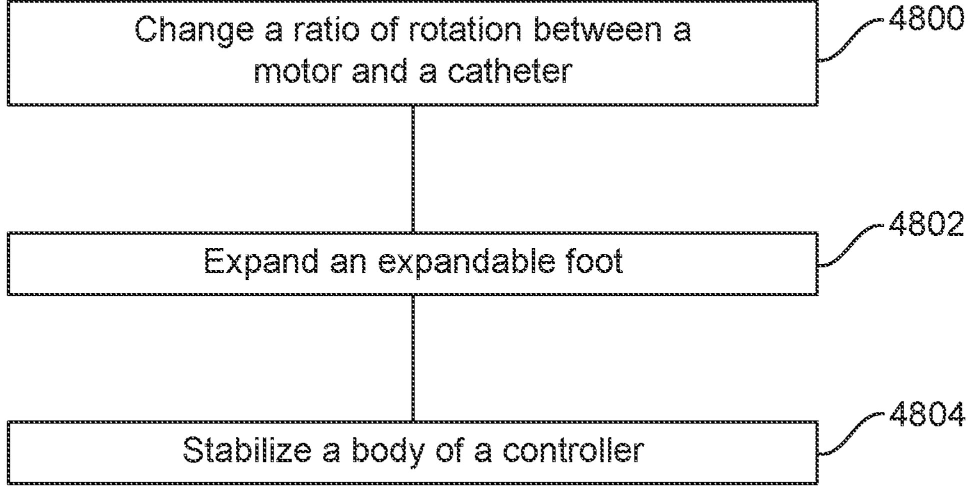
FIG. 48 illustrates a flow chart depicting a method of stabilizing a controller body, according to some examples.

FIG. 48 illustrates a flow chart depicting a method of stabilizing a controller body, according to some examples. In some examples, the method of stabilizing a controller body includes changing a ratio of rotation between a motor and a catheter (at step 4800). While not necessary for stabilizing a controller, in some instances, where the motor is placed beneath the T-fitting and/or saddle instead of behind, the controller may have a taller, but shorter in length body. In such examples, it may be necessary to increase the devices stability due to its now higher center of gravity. In placing the motor under the T-fitting and/or saddle, because the motor would no longer be in line with the insertion point of the catheter, a gear ratio may become necessary to convert the rotational movement of the motor to a rotational movement of the catheter. These gear ratios may also be used in controllers where the motor is behind the T-fitting and/or saddle, should a user of the device desire adjustable rotation options for the catheter.

According to some examples, the method of stabilizing a controller body includes expanding an expandable foot (at step 4802). An expandable foot on the bottom of the body of the controller, perhaps webbed as shown in FIG. 11, may be included in the ablation system. This expandable foot, when expanded, may lower the controller's center of gravity. This is particularly useful in example controllers like the one in the preceding paragraph where the placement of the motor gives the controller an inherent higher center of gravity, and the user wants this center of gravity to be lowered.

The method of stabilizing a controller body may include stabilizing a body of a controller (at step 4804). By lowering the controller's center of gravity by expanding the expandable foot in step 4802, the controller body gains stability. This lowers any chance of an operator accidentally tipping the controller over during a procedure.

Figure 49:
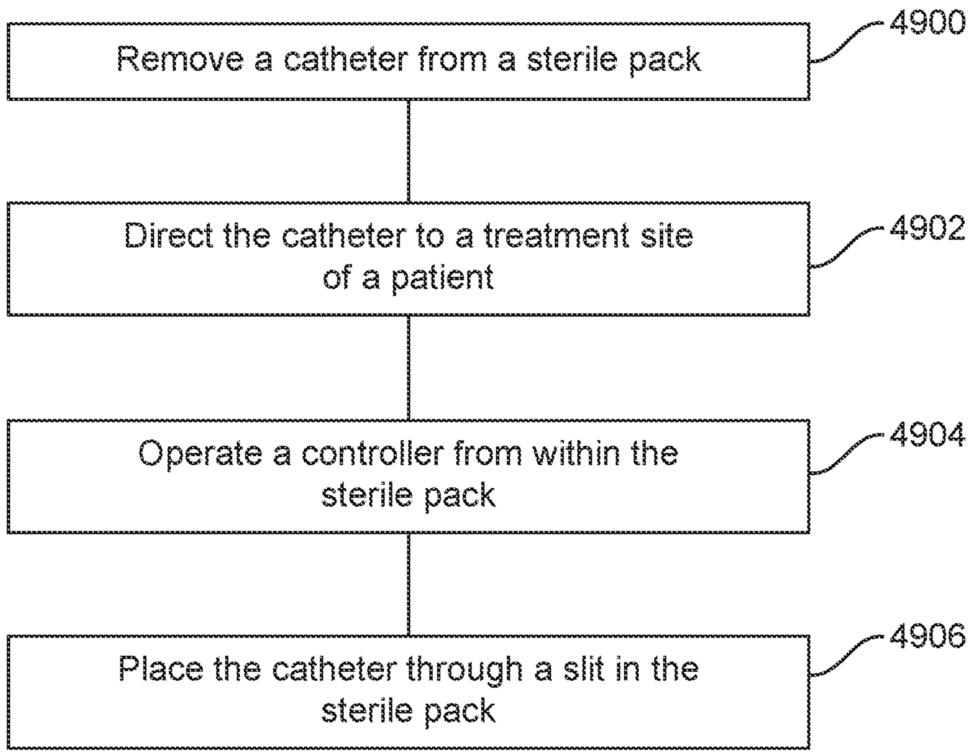
FIG. 49 illustrates a flow chart depicting a method of using a controller with a sterile pack, according to some examples.

FIG. 49 illustrates a flow chart depicting a method of using a controller with a sterile pack, according to some examples. In some examples, the method of using a controller with a sterile pack includes removing a catheter from a sterile pack (at step 4900). In some examples, the controller and the catheter come packaged together in the sterile pack. The catheter would need to be removed, at least partially, from the sterile pack in order to be inserted into the body of a patient. In some examples, the catheter is packaged separately from the controller.

According to some examples, the method of using a controller with a sterile pack includes directing the catheter to a treatment site of a patient (at step 4902). The catheter may be directed to the treatment site of the patient while coupled to the controller, or the catheter may be detachable, and an operator may choose to direct the catheter to the treatment site prior to coupling the catheter to the controller. The current disclosure also enables an operator to couple the catheter to the controller while the catheter is being delivered to the treatment site, should an operator wish to do so.

The method of using a controller with a sterile pack may include operating a controller from within the sterile pack (at step 4904). A cavity, or recess, may exist in the sterile pack in which the controller resides while packaged. After removing the catheter from the sterile pack (in examples where the catheter and the controller are packaged in the same sterile pack), the controller may be kept inside the sterile pack. In this way, the controller may maintain its sterility during use. This may permit an operator to perform a treatment without necessitating a sterile drape. Additionally, this may cut down on the costs of procedures, because, while the catheter will still need to be either sterilized or disposed of, the controller need not be sterilized after every use as long as its environment is kept sterile.

In some examples, the method of using a controller with a sterile pack includes placing the catheter through a slit in the sterile pack (at step 4906). The sterile pack may include a slit distal the controller (near the portion of the controller where the catheter would be inserted in order to couple to the controller). This slit could also be an aperture, or other cavity-type vacancy in the sterile pack through which the catheter could be inserted. In this way, the catheter may be coupled to the controller without necessitating the removal of the controller from the sterile pack, thereby maintaining the controller's sterility.

Figure 50:
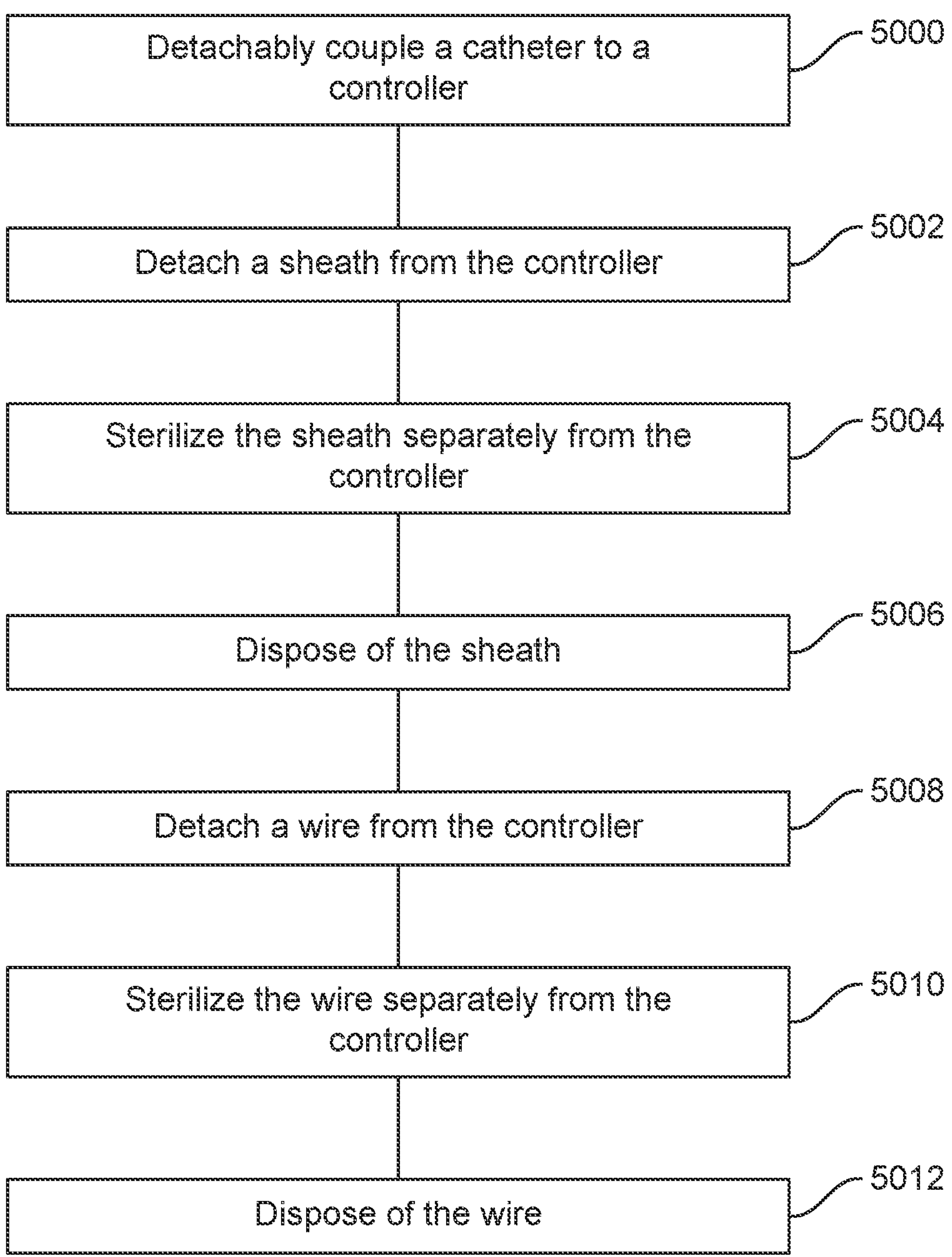
FIG. 50 illustrates a flow chart depicting a method of detachably coupling a catheter to a controller, according to some examples.

FIG. 50 illustrates a flow chart depicting a method of detachably coupling a catheter to a controller, according to some examples. According to some examples, the method of detachably coupling a catheter to a controller includes detachably coupling a catheter to a controller (at step 5000). As previously described throughout the application, the catheter may be capable of being removed from the controller entirely, thereby providing a detachable coupling between the catheter and the controller. This is understood to not be strictly necessary, and example ablation systems may be provided with the catheter fixedly coupled to the controller.

The method of detachably coupling a catheter to a controller may include detaching a sheath from the controller (at step 5002). In some examples, the catheter includes a sheath having a working lumen. In further examples, the sheath may be detachable from the controller. In such examples, the sheath may be tracked to a treatment site prior to being coupled to the controller. In examples where a wire is included through the working lumen of the sheath, the sheath may be detached from the controller and tracked to a treatment site separate from the wire, as described in FIG. 46.

In some examples, the method of detachably coupling a catheter to a controller includes sterilizing the sheath separately from the controller (at step 5004). According to some examples, the method of detachably coupling a catheter to a controller includes disposing of the sheath (at step 5006). In example ablation systems where the sheath is detachable from the controller, the sheath may be sterilized while not connected to said controller. As described in FIG. 49, this could help to cut down on sterilization costs. Additionally, the sheath may be disposed of entirely without having to dispose of the controller, meaning the controller could be reused a greater number of times than the catheter.

The method of detachably coupling a catheter to a controller may include detaching a wire from the controller (at step 5008). In some example ablation systems, the catheter further includes a wire which is passed through the working lumen of a sheath. The catheter may also include a wire without a sheath, if desired. In either case, the wire may be tracked to a treatment site prior to being coupled to the controller (or motor, in example ablation systems including a motor for rotating the wire).

In some examples, the method of detachably coupling a catheter to a controller includes sterilizing the wire separately from the controller (at step 5010). According to some examples, the method of detachably coupling a catheter to a controller includes disposing of the wire (at step 5012). In example ablation systems where the wire is detachable from the controller, the wire may be sterilized while not connected to said controller. As also described in FIG. 49, this could help to cut down on sterilization costs. Additionally, like the sheath of step 5006, the wire may be disposed of entirely without having to dispose of the controller, meaning the controller could be reusable a greater number of times than the catheter.

Included in the present disclosure is an ablation system 10, including a controller 20. In some examples, the ablation system 10 includes a sheath 40 having a working lumen, a proximal sheath end, and a distal sheath end. According to some examples, the proximal sheath end is coupled to the controller 20 and the distal sheath end is configured for insertion into a vascular system of a patient, the distal sheath end located opposite the proximal sheath end. The ablation system 10 may include a wire 30 extending from the controller 20 through the working lumen to the distal sheath end. In some examples, the wire 30 includes a proximal wire end 1202 and a distal wire end 1204 opposite the proximal wire end 1202, the distal wire end 1204 configured to engage a wall of a vessel in a treatment segment 55.

According to some examples, the sheath 40 is retractable to expose the distal wire end 1204. The distal wire end 1204 may be arranged and configured to define a compressed state when the distal wire end 1204 is located within the sheath 40 and an uncompressed state when the sheath 40 is retracted from the distal wire end 1204. In some examples, the wire 30 is configured to be delivered to the treatment segment 55 in the compressed state. According to some examples, the sheath 40 is variably retractable to expose a length of the distal wire end 1204. The length of the distal wire end 1204 may be configured to form a variable treatment length.

In some examples, the sheath 40 is detachably coupled to the controller 20. According to some examples, the sheath 40 is configured to track to the treatment segment 55 while the wire 30 remains stationary. The ablation system 10 may further include a motor 610 and/or 3308 configured to provide rotational output, wherein the wire 30 is coupled to the motor 610 and/or 3308.

In some examples, the sheath 40 includes an open distal end configured to deliver a drug to the treatment segment 55. According to some examples, the sheath 40 further includes a lumen to deliver the drug to the treatment segment 55. The sheath 40 may include an opening at the distal sheath end to deliver the drug to the treatment segment 55. In some examples, the drug is sclerosant.

According to some examples, the sheath 40 includes a closed distal end and an opening at the distal sheath end to deliver a drug to the treatment segment 55. The drug may be sclerosant.

In some examples, the distal wire end 1204 includes a sinusoidal configuration. According to some examples, the distal wire end 1204 includes a weighted tip 1210. The weighted tip 1210 may be attached to a most distal end of the wire 30. In some examples, the distal wire end 1204 defines a sinusoidal crossing-profile.

According to some examples, the sinusoidal configuration includes a non-uniform amplitude. The sheath 40 may include a closed distal end and a hole at the distal sheath end to deliver a drug to the treatment segment 55. In some examples, the non-uniform amplitude is configured to cause a spraying effect of the drug.

According to some examples, the controller 20 includes a motor 610 and/or 3308 and a power supply 606 and/or 3302 configured to provide power to the motor 610 and/or 3308. The motor 610 and/or 3308 may be configured to provide rotational output. In some examples, the proximal wire end 1202 is rotationally coupled to the motor 610 and/or 3308. According to some examples, the sinusoidal configuration is configured to rotate in response to the rotational output of the motor 610 and/or 3308.

The wire 30 may define a central axis 1208. In some examples, the distal wire end 1204 includes a sinusoidal configuration. According to some examples, the distal wire end 1204 includes a weighted tip 1210. The weighted tip 1210 may be centered on the central axis 1208, the weighted tip 1210 configured to create a gyroscopic effect. In some examples, the weighted tip 1210 is off-center and lies parallel to the central axis 1208. According to some examples, the weighted tip 1210 is configured to make contact with the wall of the vessel. The weighted tip 1210 may be off-center and lie at an angle to the central axis 1208. In some examples, the weighted tip 1210 is configured to make contact with the wall of the vessel.

According to some examples, the wire 30 includes a thickness gradient to enable thicker sections of the distal wire end 1204 to have improved contact with the wall of the vessel. The wire 30 may have a circular cross-sectional profile 1302. In some examples, the wire 30 has a flat bar cross-sectional profile 1304. According to some examples, the wire 30 has a triangular cross-sectional profile 1306.

The wire 30 may include a stranded cable 1702. In some examples, the stranded cable 1702 defines a radius, and wherein the radius is adjustable. According to some examples, the stranded cable 1702 is configured to permit a high contact force on the wall of the vessel. The stranded cable 1702 may define a sinusoidal profile.

In some examples, the controller 20 includes a motor 610 and/or 3308 and a power supply 606 and/or 3302 configured to provide power to the motor 610 and/or 3308. According to some examples, the motor 610 and/or 3308 is configured to provide rotational output. The proximal wire end 1202 may be rotationally coupled to the motor 610 and/or 3308. In some examples, the stranded cable 1702 is configured to rotate in response to the rotational output of the motor 610 and/or 3308.

In some examples, the wire 30 includes a helical hollow strand 1802 wire. According to some examples, the helical hollow strand 1802 wire is configured to deliver a drug to the treatment segment 55. The drug may be sclerosant. In some examples, the drug is configured to weep through a coil of the helical hollow strand 1802 wire. According to some examples, the helical hollow strand 1802 wire defines a sinusoidal profile. The amplitude of the sinusoidal profile may be adjustable. In some examples, the ablation system 10 further includes a pull string coupled to a distal end of the helical hollow strand 1802 wire, the pull string configured to adjust the amplitude of the sinusoidal profile.

According to some examples, the helical hollow strand 1802 wire defines a first helical hollow strand 1802 wire, the wire 30 further including a second helical hollow strand 1802 wire. The second helical hollow strand 1802 wire may at least partially surround the first helical hollow strand 1802 wire. In some examples, the first helical hollow strand 1802 wire and the second helical hollow strand 1802 wire create an oscillating motion.

According to some examples, the controller 20 includes a motor 610 and/or 3308 and a power supply 606 and/or 3302 configured to provide power to the motor 610 and/or 3308. The motor 610 and/or 3308 may be configured to provide rotational output. In some examples, the proximal wire end 1202 is rotationally coupled to the motor 610 and/or 3308. According to some examples, the helical hollow strand 1802 wire is configured to rotate in response to the rotational output of the motor 610 and/or 3308.

The helical hollow strand 1802 wire may be configured to lie flat while inside the sheath 40. In some examples, the helical hollow strand 1802 wire is configured to expand when the sheath 40 is retracted.

According to some examples, the distal wire end 1204 includes a spring-like configuration. The distal wire end 1204 may define a spring-like crossing profile 2402. In some examples, the spring-like configuration defines a sinusoidal profile.

According to some examples, the controller 20 includes a motor 610 and/or 3308 and a power supply 606 and/or 3302 configured to provide power to the motor 610 and/or 3308. The motor 610 and/or 3308 may be configured to provide rotational output. In some examples, the proximal wire end 1202 is rotationally coupled to the motor 610 and/or 3308. According to some examples, the spring-like configuration is configured to rotate in response to the rotational output of the motor 610 and/or 3308.

The distal wire end 1204 may include a three-dimensional cross-sectional profile. In some examples, the three-dimensional cross-sectional profile is a sinusoidal configuration in two dimensions, the sinusoidal configuration defining a period. According to some examples, each period the sinusoidal configuration turns in a third dimension.

The sinusoidal configuration may further define a time segment that is a portion of a period. In some examples, each time segment the sinusoidal configuration turns in a third dimension. According to some examples, each time segment is half the period.

The distal wire end 1204 may define a three-dimensional crossing-profile. In some examples, the controller 20 includes a motor 610 and/or 3308 and a power supply 606 and/or 3302 configured to provide power to the motor 610 and/or 3308. According to some examples, the motor 610 and/or 3308 is configured to provide rotational output. The proximal wire end 1202 may be rotationally coupled to the motor 610 and/or 3308. In some examples, the three-dimensional cross-sectional profile is configured to rotate in response to the rotational output of the motor 610 and/or 3308.

According to some examples, the distal wire end 1204 includes a triangular sinusoidal profile 1602. The triangular sinusoidal profile 1602 may include a triangular peak 1604. In some examples, the triangular peak 1604 is configured to make contact with the wall of the vessel.

According to some examples, the controller 20 includes a motor 610 and/or 3308 and a power supply 606 and/or 3302 configured to provide power to the motor 610 and/or 3308. The motor 610 and/or 3308 may be configured to provide rotational output. In some examples, the proximal wire end 1202 is rotationally coupled to the motor 610 and/or 3308. According to some examples, the triangular sinusoidal profile 1602 is configured to rotate in response to the rotational output of the motor 610 and/or 3308.

The distal wire end 1204 may include a basket-like shape. In some examples, the basket-like shape is configured to expand. According to some examples, the controller 20 includes a motor 610 and/or 3308 and a power supply 606 and/or 3302 configured to provide power to the motor 610 and/or 3308. The motor 610 and/or 3308 may be configured to provide rotational output. In some examples, the proximal wire end 1202 is rotationally coupled to the motor 610 and/or 3308. According to some examples, the basket-like shape is configured to rotate in response to the rotational output of the motor 610 and/or 3308.

The wire 30 may be made from a material that is capable of being shape-set. In some examples, the wire 30 is made from Nitinol.

According to some examples, the wire 30 includes a lumen from the proximal wire end 1202 to the distal wire end 1204. The wire 30 may further include an aperture 1206 at a most distal end of the wire 30. In some examples, the lumen is configured to deliver a drug to the treatment segment 55 through the aperture 1206. According to some examples, the drug is sclerosant. The wire 30 may include a hole at the distal wire end 1204. In some examples, the lumen is configured to deliver a drug to the treatment segment 55 through the hole.

According to some examples, the ablation system 10 further includes a proximal feature 2602 proximal the distal wire end 1204. The proximal feature 2602 may be configured to prevent blood from entering the treatment segment 55. In some examples, the proximal feature 2602 is configured to prevent a drug from leaving the treatment segment 55. According to some examples, the drug is sclerosant.

The proximal feature 2602 may be a balloon 2604 on the sheath 40. In some examples, the balloon 2604 at least partially surrounds the sheath 40. According to some examples, the balloon 2604 is an offset balloon 2606. The offset balloon 2606 may be biased toward a side of the sheath 40. In some examples, the offset balloon 2606 is configured to offload the wire 30 when the offset balloon 2606 is in an inflated state, thereby causing the wire 30 to contact the wall of the vessel more aggressively. According to some examples, the sheath 40 provides an inflation fluid to the balloon 2604, the inflation fluid configured to expand the balloon 2604.

The proximal feature 2602 may be a cage 2608 on the wire 30. In some examples, the proximal feature 2602 is a grooved solid 2610 on the wire 30. According to some examples, the proximal feature 2602 is an impeller 2612 on the wire 30. The proximal feature 2602 may be a sponge-like solid 2614 at least partially surrounding the wire 30. In some examples, the proximal feature 2602 is a sponge-like solid 2614 at least partially surrounding the sheath 40.

According to some examples, the proximal feature 2602 is a sinusoidal urge 2616 in the wire 30. The sinusoidal urge 2616 may be at least partially contained within the sheath 40 when the sheath 40 is retracted. In some examples, the sinusoidal urge 2616 is configured to offload the wire 30, thereby causing the wire 30 to contact the wall of the vessel more aggressively.

According to some examples, the ablation system 10 further includes a distal feature 2702 proximal on a distal portion of the distal wire end 1204. The distal feature 2702 may be configured to prevent blood from entering the treatment segment 55. In some examples, the distal feature 2702 is configured to prevent a drug from leaving the treatment segment 55.

According to some examples, the distal feature 2702 is single blade impeller 2704 on the wire 30. The distal feature 2702 may be a cage 2706 on the wire 30. In some examples, the distal feature 2702 is a grooved solid 2708 on the wire 30. According to some examples, the distal feature 2702 is an impeller 2710 on the wire 30. The distal feature 2702 may be a sponge-like solid 2712 at least partially surrounding the wire 30.

In some examples, a distal most tip of the wire 30 is a hemispherical tip 2802. According to some examples, the hemispherical tip 2802 is weighted. The hemispherical tip 2802 may be configured to make contact with the wall of the vessel.

In some examples, a distal most tip of the wire 30 is an offset weighted tip 2804. According to some examples, the offset weighted tip 2804 is weighted. The offset weighted tip 2804 may be configured to make contact with the wall of the vessel.

In some examples, the wire 30 includes a lumen. According to some examples, a distal most tip of the wire 30 is a balloon tip 2806. The lumen may be configured to provide an inflation fluid to the balloon tip 2806, the inflation fluid configured to expand the balloon tip 2806. In some examples, the balloon tip 2806 is configured to occlude the vessel when in an expanded state.

According to some examples, the ablation system 10 further includes a supplementary wire 2902 wrapped around at least a part of the distal wire end 1204. The supplementary wire 2902 may be a heated wire 2904. In some examples, the heated wire 2904 is configured to coerce the wire 30 into a predetermined shape in response to a temperature. According to some examples, the predetermined shape is a sinusoidal profile. The temperature may be a human body temperature.

In some examples, the supplementary wire 2902 is a hypotube. According to some examples, the hypotube is configured to deliver a drug to a treatment segment 55. The drug may be sclerosant.

In some examples, at least a portion of the distal wire end 1204 includes a porous surface geometry 2906. According to some examples, the porous surface geometry 2906 is configured to make aggressive contact with the wall of the vessel.

At least a portion of the distal wire end 1204 may include an additional geometry 3002*a*, 3002*b*, 3002*c*, and/or 3002*d*. In some examples, the additional geometry 3002*a* includes a rounded nub. According to some examples, the additional geometry 3002*b* includes a ball. The additional geometry 3002*c* may include a spike. In some examples, the additional geometry 3002*d* includes a brush. According to some examples, the additional geometry 3002*a*, 3002*b*, 3002*c*, and/or 3002*d* is configured to make aggressive contact with the wall of the vessel. The wire 30 may include a sinusoidal profile. In some examples, the sinusoidal profile defines a peak. According to some examples, the additional geometry 3002*a*, 3002*b*, 3002*c*, and/or 3002*d* is located on the peak.

The ablation system 10 may further include a donut 3202 at least partially surrounding the sheath 40. In some examples, the donut 3202 is slidably coupled to the sheath 40. According to some examples, the donut 3202 is sized such that it cannot enter an insertion point in the patient. The donut 3202 may be configured to keep the sheath 40 and the wire 30 in place during a treatment. In some examples, the donut 3202 is configured to indicate a distance to a deep venous system in the patient.

According to some examples, the ablation system 10 further includes at least one distance marking 3204 on the sheath 40. The at least one distance marking 3204 may be configured to show a distance the sheath 40 is removed from the patient. In some examples, the at least one distance marking 3204 is configured to inform a user that a subsequent treatment segment 55 has been reached. According to some examples, a space between the at least one distance marking 3204 and a subsequent at least one distance marking 3204 is about the same as a length of the distal wire end 1204. The distal wire end 1204 may define a treatment segment 55. In some examples, the at least one distance marking 3204 at least partially surrounds the sheath 40.

According to some examples, the ablation system 10 further includes a warning track 3206 on the sheath 40. The warning track 3206 may be configured to inform a user that an end of a workable treatment length has been reached. In some examples, the warning track 3206 at least partially surrounds the sheath 40.

Also included in the present disclosure is an ablation system 10 including a controller 20. In some examples, the ablation system 10 includes a sheath 40 including a working lumen, a proximal sheath end, and a distal sheath end. According to some examples, the proximal sheath end is coupled to the controller 20 and the distal sheath end is configured for insertion into a vascular system of a patient, the distal sheath end located opposite the proximal sheath end. The ablation system 10 may include a wire 30 extending from the controller 20 through the working lumen to the distal sheath end. In some examples, the wire 30 includes a proximal wire end 1202 and a distal wire end 1204 opposite the proximal wire end 1202, the distal wire end 1204 configured to engage a wall of a vessel in a treatment segment 55.

According to some examples, the controller 20 includes a motor 610 and/or 3308 and a power supply 606 and/or 3302 configured to provide power to the motor 610 and/or 3308. The controller 20 may further include an actuator **506*a*, 506*b*, 608, 914, and/or 3304 to activate the motor 610 and/or 3308. In some examples, the motor 610 and/or 3308 is configured to provide rotational output. According to some examples, the proximal wire end 1202 is rotationally coupled to the motor 610 and/or 3308. The motor 610 and/or 3308 may rotate the distal wire end 1204 at between about 1000 revolutions per minute (RPM) and about 4000 RPM. In some examples, the controller 20 includes a torque limiter and a clutch to stop a rotation of the wire 30** if a torque limit is exceeded.

According to some examples, the controller 20 is a handle. The handle may include a slot 602 and the proximal sheath end includes a inflation tuohy 604 that couples to the slot 602. In some examples, retraction of the inflation tuohy 604 into the slot 602 retracts the sheath 40 and exposes the distal wire end 1204. According to some examples, a flow path from the handle into the sheath 40 is established for injection of sclerosant at the treatment segment 55.

The controller 20 may include a display 508. In some examples, the display 508 is configured to show a timer. According to some examples, the timer is configured to countdown a time remaining in a treatment.

Also included in the present disclosure is an ablation system 10, including a body 702, 802, and or 902 defining a proximal body end 708, 806, and/or 906 and a distal body end 710, 808, and/or 908 opposite the proximal body end 708, 806, and/or 906. The ablation system 10 may include a saddle 704 slidably coupled to the body 702, 802, and or 902 whereby the saddle 704 moves along a first direction 712, 810, and or 916 extending from the proximal body end 708, 806, and/or 906 to the distal body end 710, 808, and/or 908. In some examples, the ablation system 10 includes a T-fitting 706, 804, and/or 904 slidably coupled to the body 702, 802, and or 902 and at least partially surrounded by a center portion of the saddle 704, whereby the T-fitting 706, 804, and/or 904 moves along the first direction 712, 810, and or 916 in response to a movement of the saddle 704.

According to some examples, the ablation system 10 further includes a syringe 60 configured to couple to the T-fitting 706, 804, and/or 904. A component selected from the group consisting of the syringe 60, the saddle 704, and combinations thereof may be configured to control a movement of the T-fitting 706, 804, and/or 904. In some examples, the syringe 60 is configured to insert into the T-fitting 706, 804, and/or 904 along a second direction that is at an angle to the first direction 712, 810, and or 916. According to some examples, the angle is perpendicular.

The ablation system 10 may further include a syringe 60 configured to couple to the T-fitting 706, 804, and/or 904. In some examples, a component selected from the group consisting of the syringe 60, the saddle 704, and combinations thereof is configured to control a movement of the T-fitting 706, 804, and/or 904. According to some examples, the ablation system 10 further includes a sheath 40 including a proximal sheath end, a distal sheath end opposite the proximal sheath end, and a working lumen therebetween. The proximal sheath end may be configured to couple to the distal body end 710, 808, and/or 908. In some examples, the working lumen is in fluid communication with the syringe 60.

According to some examples, the sheath 40 is configured to receive a wire 30, the wire 30 including a proximal wire end 1202 and a distal wire end 1204 opposite the proximal wire end 1202. Sliding the T-fitting 706, 804, and/or 904 from the distal body end 710, 808, and/or 908 toward the proximal body end 708, 806, and/or 906 may retract the sheath 40 about the wire 30, exposing the distal wire end 1204. In some examples, sliding the T-fitting 706, 804, and/or 904 from the proximal body end 708, 806, and/or 906 toward the distal body end 710, 808, and/or 908 extends the sheath 40 about the wire 30, at least partially enclosing the distal wire end 1204.

According to some examples, the sheath 40 is configured to receive a hypotube, the hypotube including a proximal hypotube end and a distal hypotube end opposite the proximal hypotube end. Sliding the T-fitting 706, 804, and/or 904 from the distal body end 710, 808, and/or 908 toward the proximal body end 708, 806, and/or 906 may retract the sheath 40 about the hypotube, exposing the distal hypotube end. In some examples, sliding the T-fitting 706, 804, and/or 904 from the proximal body end 708, 806, and/or 906 toward the distal body end 710, 808, and/or 908 extends the sheath 40 about the hypotube, at least partially enclosing the distal hypotube end.

According to some examples, the sheath 40 is configured to receive a catheter shaft, the catheter shaft including a proximal catheter shaft end and a distal catheter shaft end opposite the proximal catheter shaft end. Sliding the T-fitting 706, 804, and/or 904 from the distal body end 710, 808, and/or 908 toward the proximal body end 708, 806, and/or 906 may retract the sheath 40 about the catheter shaft, exposing the distal catheter shaft end. In some examples, sliding the T-fitting 706, 804, and/or 904 from the proximal body end 708, 806, and/or 906 toward the distal body end 710, 808, and/or 908 extends the sheath 40 about the catheter shaft, at least partially enclosing the distal catheter shaft end.

According to some examples, the T-fitting 706, 804, and/or 904 includes a luer hub 3102. The ablation system 10 may further include a syringe 60 configured to couple to the T-fitting 706, 804, and/or 904. In some examples, a component selected from the group consisting of the syringe 60, the saddle 704, and combinations thereof is configured to control a movement of the T-fitting 706, 804, and/or 904. According to some examples, the luer hub 3102 includes a luer 3104, the luer 3104 configured to detachably couple the syringe 60 to the T-fitting 706, 804, and/or 904. The luer 3104 may be configured to rotate approximately 180 degrees about the first direction 712, 810, and or 916. In some examples, the syringe 60 is configured to control a rotation of the luer 3104.

According to some examples, the ablation system 10 further includes a catheter 15 having a proximal catheter end and a distal catheter end opposite the proximal catheter end. The proximal catheter end may be configured to couple to the distal body end 710, 808, and/or 908. In some examples, the catheter 15 is in fluid communication with the syringe 60. According to some examples, the luer 3104 is configured to provide a torque on the catheter 15. The torque may be configured to control a direction of travel of the distal catheter end.

In some examples, the ablation system 10 further includes a sheath 40 including a proximal sheath end and a distal sheath end opposite the proximal sheath end. According to some examples, the proximal sheath end is configured to removably couple to the luer hub 3102. The sheath 40 may be in fluid communication with the syringe 60. In some examples, the luer 3104 is configured to provide a torque on the sheath 40. According to some examples, the torque is configured to control a direction of travel of the distal sheath end.

The sheath 40 may further include a working lumen. In some examples, the ablation system 10 further includes a wire 30 extending from the body 702, 802, and or 902 through the working lumen to the distal sheath end, the wire 30 having a proximal wire end 1202 and a distal wire end 1204 opposite the proximal wire end 1202. According to some examples, the distal wire end 1204 is configured to engage a wall of a vessel in a treatment segment 55.

The ablation system 10 may further include a torque knob 1104 rotatably coupled to the body 702, 802, and or 902. In some examples, the torque knob 1104 is located on the proximal body end 708, 806, and/or 906.

According to some examples, the ablation system 10 further includes a syringe 60 configured to couple to the T-fitting 706, 804, and/or 904. A component selected from the group consisting of the syringe 60, the saddle 704, and combinations thereof may be configured to control a movement of the T-fitting 706, 804, and/or 904. In some examples, the ablation system 10 further includes a catheter 15 having a proximal catheter end and a distal catheter end opposite the proximal catheter end. According to some examples, the proximal catheter end is configured to couple to the distal body end 710, 808, and/or 908. The catheter 15 may be in fluid communication with the syringe 60.

In some examples, the torque knob 1104 is configured to provide a torque on the catheter 15. According to some examples, the torque is configured to control a direction of travel of the distal catheter end.

The ablation system 10 may further include a wire 30, including a proximal wire end 1202 and a distal wire end 1204 opposite the proximal wire end 1202. In some examples, the proximal wire end 1202 is configured to couple to the distal body end 710, 808, and/or 908. According to some examples, the torque knob 1104 is configured to provide a torque on the wire 30. The torque may be configured to control a direction of travel of the distal wire end 1204.

In some examples, the ablation system 10 further includes a motor 610 and/or 3308 at least partially enclosed within the body 702, 802, and or 902. According to some examples, the motor 610 and/or 3308 is at least partially enclosed within the proximal body end 708, 806, and/or 906. The ablation system 10 may further include an actuator **506*a*, 506*b*, 608, 914, and/or 3304 coupled to the body 702, 802, and or 902 and electronically coupled to the motor 610 and/or 3308, the actuator 506*a*, 506*b*, 608, 914, and/or 3304 configured to power the motor 610 and/or 3308** on and off.

In some examples, the ablation system 10 further includes a wire 30 including a proximal wire end 1202 and a distal wire end 1204 opposite the proximal wire end 1202. According to some examples, the proximal wire end 1202 is configured to couple to the motor 610 and/or 3308. The motor 610 and/or 3308 may be configured to effectuate rotation to the wire 30.

In some examples, the ablation system 10 further includes a hypotube, including a proximal hypotube end and a distal hypotube end opposite the proximal hypotube end. According to some examples, the proximal hypotube end is configured to couple to the motor 610 and/or 3308. The motor 610 and/or 3308 may be configured to effectuate rotation to the hypotube.

In some examples, the ablation system 10 further includes a catheter shaft including a proximal catheter shaft end and a distal catheter shaft end opposite the proximal catheter shaft end. According to some examples, the proximal catheter shaft end configured to couple to the motor 610 and/or 3308. The motor 610 and/or 3308 may be configured to effectuate rotation to the catheter shaft.

In some examples, the ablation system 10 further includes limit switch 3306 electronically coupled to the motor 610 and/or 3308. According to some examples, the limit switch 3306 is configured to prevent the motor 610 and/or 3308 from rotating when the saddle 704 is positioned at a location other than the proximal body end 708, 806, and/or 906. The limit switch 3306 may be configured to permit the motor 610 and/or 3308 to rotate when the saddle 704 is positioned at the proximal body end 708, 806, and/or 906.

In some examples, the ablation system 10 further includes an LED 912 and/or 3310 electronically coupled to the motor 610 and/or 3308. According to some examples, the LED 912 and/or 3310 is configured to power off when the saddle 704 is positioned at a location other than the proximal body end 708, 806, and/or 906. The LED 912 and/or 3310 may be configured to power on when the saddle 704 is positioned at the proximal body end 708, 806, and/or 906.

In some examples, the saddle 704 is at least partially inside of the body 702, 802, and or 902. According to some examples, the saddle 704 includes a pull tab configured to facilitate movement of the saddle 704. The T-fitting 706, 804, and/or 904 may be fixedly coupled to the saddle 704.

In some examples, the ablation system 10 further includes a display 508 configured to indicate information. According to some examples, the display 508 is configured to show a timer. The timer may be configured to countdown a time remaining in a treatment. In some examples, the ablation system 10 further includes a catheter 15 coupled to the distal body end 710, 808, and/or 908. According to some examples, the timer is configured to countdown a time until a treatment in a treatment segment 55 is completed and the catheter 15 is to be moved to a subsequent treatment segment 55.

The ablation system 10 may further include a syringe 60 configured to couple to the T-fitting 706, 804, and/or 904. In some examples, a component selected from the group consisting of the syringe 60, the saddle 704, and combinations thereof is configured to control a movement of the T-fitting 706, 804, and/or 904. According to some examples, the timer is configured to countdown a time until an operator should begin injecting a drug from the syringe 60. The timer may be configured to countdown a time until the operator should discontinue injecting the drug from the syringe 60.

In some examples, the ablation system 10 further includes an alarm configured to sound a noise at an end of a treatment. According to some examples, the ablation system 10 further includes a catheter 15 coupled to the distal body end 710, 808, and/or 908. The ablation system 10 may further include an alarm configured to sound a noise when a treatment in a treatment segment 55 is completed and an operator is to move the catheter 15 to a subsequent treatment segment 55.

In some examples, the ablation system 10 further includes a syringe 60 configured to couple to the T-fitting 706, 804, and/or 904. According to some examples, a component selected from the group consisting of the syringe 60, the saddle 704, and combinations thereof is configured to control a movement of the T-fitting 706, 804, and/or 904. The ablation system 10 may further include an alarm configured to sound a noise when an operator should begin injecting a drug from the syringe 60. In some examples, the alarm is configured to sound the noise when the operator should discontinue injecting the drug from the syringe 60.

According to some examples, the ablation system 10 further includes an LED 912 and/or 3310 configured to turn on at an end of a treatment. The ablation system 10 may further include an LED 912 and/or 3310 configured to turn off at an end of a treatment. In some examples, the ablation system 10 further includes a catheter 15 coupled to the distal body end 710, 808, and/or 908, and an LED 912 and/or 3310 configured to turn on when a treatment in a treatment segment 55 is completed and an operator is to move the catheter 15 to a subsequent treatment segment 55. According to some examples, the ablation system 10 further includes a catheter 15 coupled to the distal body end 710, 808, and/or 908, and an LED 912 and/or 3310 configured to turn off when a treatment in a treatment segment 55 is completed and an operator is to move the catheter 15 to a subsequent treatment segment 55.

The ablation system 10 may further include a syringe 60 configured to couple to the T-fitting 706, 804, and/or 904. In some examples, a component selected from the group consisting of the syringe 60, the saddle 704, and combinations thereof is configured to control a movement of the T-fitting 706, 804, and/or 904. According to some examples, the ablation system 10 further includes an LED 912 and/or 3310 configured to turn on when an operator should begin injecting a drug from the syringe 60. The LED 912 and/or 3310 may be configured to turn off when the operator should discontinue injecting the drug from the syringe 60.

In some examples, the ablation system 10 further includes a syringe 60 configured to couple to the T-fitting 706, 804, and/or 904. According to some examples, a component selected from the group consisting of the syringe 60, the saddle 704, and combinations thereof is configured to control a movement of the T-fitting 706, 804, and/or 904. The ablation system 10 may further include an LED 912 and/or 3310 configured to turn off when an operator should begin injecting a drug from the syringe 60. In some examples, the LED 912 and/or 3310 is configured to turn on when the operator should discontinue injecting the drug from the syringe 60.

According to some examples, the ablation system 10 further includes a motor 610 and/or 3308 located near a bottom of the body 702, 802, and or 902. The ablation system 10 may further include a gear coupled to the motor 610 and/or 3308. In some examples, the gear is configured to control an output rotation speed of the motor 610 and/or 3308.

According to some examples, the ablation system 10 further includes an expandable foot 1102 on a base of the body 702, 802, and or 902. The expandable foot 1102 may be configured to facilitate stability of the body 702, 802, and or 902.

In some examples, the ablation system 10 further includes a catheter 15, including a proximal catheter end and a distal catheter end opposite the proximal catheter end. According to some examples, the proximal catheter end is coupled to the distal body end 710, 808, and/or 908. The ablation system 10 may further include an arm 1106 coupled to a side of the body 702, 802, and or 902.

In some examples, when the distal catheter end travels in a direction opposite the first direction 712, 810, and or 916, the arm 1106 is configured to maintain a distance between the catheter 15 and the body 702, 802, and or 902. According to some examples, the distance between the catheter 15 and the body 702, 802, and or 902 is a radius. The arm 1106 may be configured to keep the catheter 15 in place during a treatment.

In some examples, the ablation system 10 further includes a catheter 15, including a proximal catheter end and a distal catheter end opposite the proximal catheter end. According to some examples, the proximal catheter end is coupled to the distal body end 710, 808, and/or 908. The ablation system 10 may further include a catheter clamp configured to keep the catheter 15 in place during a treatment.

In some examples, the ablation system 10 further includes a sheath 40, including a working lumen, a proximal sheath end, and a distal sheath end. According to some examples, the proximal sheath end is coupled to the distal body end 710, 808, and/or 908, and the distal sheath end is configured for insertion into a vascular system of a patient, the distal sheath end located opposite the proximal sheath end. The ablation system 10 may further include a wire 30 extending from the distal body end 710, 808, and/or 908 through the working lumen to the distal sheath end, the wire 30 having a proximal wire end 1202 and a distal wire end 1204 opposite the proximal wire end 1202. In some examples, the distal wire end 1204 is configured to engage a wall of a vessel in a treatment segment 55.

According to some examples, the sheath 40 is detachably coupled to the distal body end 710, 808, and/or 908. The sheath 40 may be configured to track to the treatment segment 55 while the wire 30 remains stationary.

In some examples, the ablation system 10 further includes a sterile pack 1002. According to some examples, the body 702, 802, and or 902, the saddle 704, the T-fitting 706, 804, and/or 904, the sheath 40, and the wire 30 are configured to fit within a cavity of the sterile pack 1002. The sheath 40 and the wire 30 may be detachably coupled to the distal body end 710, 808, and/or 908. In some examples, the sheath 40 and the wire 30 are configured to be sterilized separate from the body 702, 802, and or 902. According to some examples, the sheath 40 and the wire 30 are configured to be disposable. The ablation system 10 may be configured to be operated while in the sterile pack 1002.

In some examples, the sterile pack 1002 includes a slit 1004. According to some examples, the slit 1004 is configured to slidably receive the sheath 40. The body 702, 802, and or 902, the saddle 704, and the T-fitting 706, 804, and/or 904 may be configured to sit within the cavity of the sterile pack 1002 during an operation. In some examples, the sheath 40 and the wire 30 are configured to slidably couple to the slit 1004 during an operation. According to some examples, the body 702, 802, and or 902, the saddle 704, and the T-fitting 706, 804, and/or 904 are configured to be reusable.

The ablation system 10 may further include a sterile pack 1002, wherein the body 702, 802, and or 902, the saddle 704, and the T-fitting 706, 804, and/or 904 are configured to fit within a cavity of the sterile pack 1002. In some examples, the ablation system 10 is configured to be operated while in the sterile pack 1002.

Also included in the present disclosure is a method, including inserting a syringe 60 into a T-fitting 706, 804, and/or 904 of a saddle 704 of a body 702, 802, and or 902. In some examples, the body 702, 802, and or 902 has a proximal body end 708, 806, and/or 906 and a distal body end 710, 808, and/or 908. According to some examples, the saddle 704 is slidably coupled to the body 702, 802, and or 902, whereby the saddle 704 moves along a first direction 712, 810, and or 916. The first direction 712, 810, and or 916 may extend from the proximal body end 708, 806, and/or 906 to the distal body end 710, 808, and/or 908. In some examples, the T-fitting 706, 804, and/or 904 moves along the first direction 712, 810, and or 916 in response to movement of the saddle 704. According to some examples, the syringe 60 is inserted into the T-fitting 706, 804, and/or 904 along a second direction that is perpendicular to the first direction 712, 810, and or 916. The method may include directing a catheter 15 to a treatment site 50 of a patient.

In some examples, the catheter 15 includes a sheath 40 configured to receive a wire 30, the wire 30 including a proximal wire end 1202 and a distal wire end 1204 opposite the proximal wire end 1202. According to some examples, the method further includes sliding, via the saddle 704, the T-fitting 706, 804, and/or 904 from the distal body end 710, 808, and/or 908 toward the proximal body end 708, 806, and/or 906. The method may further include retracting the sheath 40 about the wire 30 in response to sliding the T-fitting 706, 804, and/or 904. In some examples, the method further includes exposing the distal wire end 1204 in response to retracting the sheath 40.

According to some examples, the method further includes sliding, via the syringe 60, the T-fitting 706, 804, and/or 904 from the distal body end 710, 808, and/or 908 toward the proximal body end 708, 806, and/or 906. The saddle 704 may include a pull tab. In some examples, the method further includes sliding, via the pull tab, the T-fitting 706, 804, and/or 904 from the distal body end 710, 808, and/or 908 toward the proximal body end 708, 806, and/or 906.

According to some examples, the catheter 15 includes a sheath 40 configured to receive a wire 30, the wire 30 including a proximal wire end 1202 and a distal wire end 1204 opposite the proximal wire end 1202. The method may further include sliding, via the saddle 704, the T-fitting 706, 804, and/or 904 from the proximal body end 708, 806, and/or 906 toward the distal body end 710, 808, and/or 908. In some examples, the method further includes extending the sheath 40 about the wire 30 in response to sliding the T-fitting 706, 804, and/or 904. According to some examples, the method further includes at least partially enclosing the distal wire end 1204 in response to extending the sheath 40.

The method may further include sliding, via the syringe 60, the T-fitting 706, 804, and/or 904 from the proximal body end 708, 806, and/or 906 toward the distal body end 710, 808, and/or 908. In some examples, the saddle 704 includes a pull tab. According to some examples, the method further includes sliding, via the pull tab, the T-fitting 706, 804, and/or 904 from the proximal body end 708, 806, and/or 906 toward the distal body end 710, 808, and/or 908.

The catheter 15 may include a sheath 40 configured to receive a hypotube, the hypotube including a proximal hypotube end a distal hypotube end opposite the proximal hypotube end. In some examples, the method further includes sliding, via the saddle 704, the T-fitting 706, 804, and/or 904 from the distal body end 710, 808, and/or 908 toward the proximal body end 708, 806, and/or 906. According to some examples, the method further includes retracting the sheath 40 about the hypotube in response to sliding the T-fitting 706, 804, and/or 904. The method may further include exposing the distal hypotube end in response to retracting the sheath 40.

In some examples, the method further includes sliding, via the syringe 60, the T-fitting 706, 804, and/or 904 from the distal body end 710, 808, and/or 908 toward the proximal body end 708, 806, and/or 906. According to some examples, the saddle 704 includes a pull tab. The method may further include sliding, via the pull tab, the T-fitting 706, 804, and/or 904 from the distal body end 710, 808, and/or 908 toward the proximal body end 708, 806, and/or 906.

In some examples, the catheter 15 includes a sheath 40 configured to receive a hypotube, the hypotube including a proximal hypotube end a distal hypotube end opposite the proximal hypotube end. According to some examples, the method further includes sliding, via the saddle 704, the T-fitting 706, 804, and/or 904 from the proximal body end 708, 806, and/or 906 toward the distal body end 710, 808, and/or 908. The method may further include extending the sheath 40 about the hypotube in response to sliding the T-fitting 706, 804, and/or 904. In some examples, the method further includes at least partially enclosing the distal hypotube end in response to extending the sheath 40.

According to some examples, the method further includes sliding, via the syringe 60, the T-fitting 706, 804, and/or 904 from the proximal body end 708, 806, and/or 906 toward the distal body end 710, 808, and/or 908. The saddle 704 may include a pull tab. In some examples, the method further includes sliding, via the pull tab, the T-fitting 706, 804, and/or 904 from the proximal body end 708, 806, and/or 906 toward the distal body end 710, 808, and/or 908.

According to some examples, the catheter 15 includes a sheath 40 configured to receive a catheter shaft, the catheter shaft including a proximal catheter shaft end and a distal catheter shaft end opposite the proximal catheter shaft end. The method may further include sliding, via the saddle 704, the T-fitting 706, 804, and/or 904 from the distal body end 710, 808, and/or 908 toward the proximal body end 708, 806, and/or 906. In some examples, the method further includes retracting the sheath 40 about the catheter shaft in response to sliding the T-fitting 706, 804, and/or 904. According to some examples, the method further includes exposing the distal catheter shaft end in response to retracting the sheath 40.

The method may further include sliding, via the syringe 60, the T-fitting 706, 804, and/or 904 from the distal body end 710, 808, and/or 908 toward the proximal body end 708, 806, and/or 906. In some examples, the saddle 704 includes a pull tab. According to some examples, the method further includes sliding, via the pull tab, the T-fitting 706, 804, and/or 904 from the distal body end 710, 808, and/or 908 toward the proximal body end 708, 806, and/or 906.

The catheter 15 may include a sheath 40 configured to receive a catheter shaft, the catheter shaft including a proximal catheter shaft end and a distal catheter shaft end opposite the proximal catheter shaft end. In some examples, the method includes sliding, via the saddle 704, the T-fitting 706, 804, and/or 904 from the proximal body end 708, 806, and/or 906 toward the distal body end 710, 808, and/or 908. According to some examples, the method further includes extending the sheath 40 about the catheter shaft in response to sliding the T-fitting 706, 804, and/or 904. The method may further include at least partially enclosing the distal catheter shaft end in response to extending the sheath 40.

In some examples, the method further includes sliding, via the syringe 60, the T-fitting 706, 804, and/or 904 from the proximal body end 708, 806, and/or 906 toward the distal body end 710, 808, and/or 908. According to some examples, the saddle 704 includes a pull tab. The method may further include sliding, via the pull tab, the T-fitting 706, 804, and/or 904 from the proximal body end 708, 806, and/or 906 toward the distal body end 710, 808, and/or 908.

In some examples, the T-fitting 706, 804, and/or 904 further includes a luer 3104 configured to receive the syringe 60. According to some examples, the method further includes inserting the syringe 60 into the luer 3104. The luer 3104 may be configured to rotate approximately 180 degrees about the first direction 712, 810, and or 916. In some examples, the method further includes rotating the syringe 60 and the luer 3104. According to some examples, the method further includes providing torque to the catheter 15 in response to rotating the syringe 60 and the luer 3104. The method may further include controlling a direction of travel of the distal catheter shaft end in response to providing torque to the catheter 15.

In some examples, the luer 3104 includes a connection configured to removably couple a sheath 40 to the body 702, 802, and or 902. According to some examples, the method further includes removably coupling the sheath 40 the body 702, 802, and or 902. The method may further include removing the sheath 40 from the body 702, 802, and or 902. In some examples, the method further includes directing the sheath 40 to the treatment site 50 of the patient.

According to some examples, a motor 610 and/or 3308 is at least partially enclosed within the body 702, 802, and or 902. The catheter 15 may at least partially surround a wire 30, including a proximal wire end 1202 and a distal wire end 1204 opposite the proximal wire end 1202. In some examples, the proximal wire end 1202 is configured to couple to the motor 610 and/or 3308. According to some examples, the method further includes rotating, via the motor 610 and/or 3308, the wire 30.

An actuator 506*a*, 506*b*, 608, 914, and/or 3304 may be coupled to the body 702, 802, and or 902 and electronically coupled to the motor 610 and/or 3308. In some examples, the method further includes interacting with the actuator 506*a*, 506*b*, 608, 914, and/or 3304. According to some examples, the method further includes powering on the motor 610 and/or 3308 in response to interacting with the actuator 506*a*, 506*b*, 608, 914, and/or 3304. The method may further include powering off the motor 610 and/or 3308 in response to interacting with the actuator 506*a*, 506*b*, 608, 914, and/or 3304.

In some examples, a motor 610 and/or 3308 is at least partially enclosed within the body 702, 802, and or 902. According to some examples, the catheter 15 at least partially surrounds a hypotube, including a proximal hypotube end and a distal hypotube end opposite the proximal hypotube end. The proximal hypotube end may be configured to couple to the motor 610 and/or 3308. In some examples, the method further includes rotating, via the motor 610 and/or 3308, the hypotube.

According to some examples, an actuator 506*a*, 506*b*, 608, 914, and/or 3304 is coupled to the body 702, 802, and or 902 and electronically coupled to the motor 610 and/or 3308. The method may further include interacting with the actuator 506*a*, 506*b*, 608, 914, and/or 3304. In some examples, the method further includes powering on the motor 610 and/or 3308 in response to interacting with the actuator 506*a*, 506*b*, 608, 914, and/or 3304. According to some examples, the method further includes powering off the motor 610 and/or 3308 in response to interacting with the actuator 506*a*, 506*b*, 608, 914, and/or 3304.

A motor 610 and/or 3308 may be at least partially enclosed within the body 702, 802, and or 902. In some examples, the catheter 15 at least partially surrounds a catheter shaft, including a proximal catheter shaft end and a distal catheter shaft end opposite the proximal catheter shaft end. According to some examples, the proximal catheter shaft end is configured to couple to the motor 610 and/or 3308. The method may further include rotating, via the motor 610 and/or 3308, the catheter shaft.

In some examples, an actuator 506*a*, 506*b*, 608, 914, and/or 3304 is coupled to the body 702, 802, and or 902 and electronically coupled to the motor 610 and/or 3308. According to some examples, the method further includes interacting with the actuator 506*a*, 506*b*, 608, 914, and/or 3304. The method may further include powering on the motor 610 and/or 3308 in response to interacting with the actuator 506*a*, 506*b*, 608, 914, and/or 3304. In some examples, the method further includes powering off the motor 610 and/or 3308 in response to interacting with the actuator 506*a*, 506*b*, 608, 914, and/or 3304.

According to some examples, the syringe 60 includes a syringe body and a plunger. The method may further include depressing the plunger of the syringe 60. In some examples, the method further includes releasing a fluid through the catheter 15 in response to depressing the plunger.

Also included in the present disclosure is a method, including directing a wire 30 to a treatment site 50 of a patient. In some examples, the wire 30 includes a proximal wire end 1202 and a distal wire end 1204 opposite the proximal wire end 1202. According to some examples, the wire 30 is coupled to a motor 610 and/or 3308 that is at least partially enclosed by a body 702, 802, and or 902. The method may include powering the motor 610 and/or 3308. According to some examples, the method includes rotating the wire 30 in response to powering the motor 610 and/or 3308.

The method may further include extending the wire 30 through a sheath 40 coupled to the body 702, 802, and or 902. In some examples, the method includes detachably coupling the sheath 40 to the body 702, 802, and or 902. According to some examples, the method further includes directing the sheath 40 to the treatment site 50 of the patient while the sheath 40 is detached from the body 702, 802, and or 902.

The method may further include retracting the sheath 40 about the wire 30. In some examples, the method further includes exposing the distal wire end 1204 in response to retracting the sheath 40. According to some examples, a limit switch 3306 is electronically coupled to the motor 610 and/or 3308. The method may further include allowing the motor 610 and/or 3308 to rotate in response to retracting the sheath 40 about the wire 30.

In some examples, the body 702, 802, and or 902 includes a proximal body end 708, 806, and/or 906 and a distal body end 710, 808, and/or 908. According to some examples, a saddle 704 is slidably coupled to the body 702, 802, and or 902 whereby the saddle 704 moves along a first direction 712, 810, and or 916. The first direction 712, 810, and or 916 may extend from the proximal body end 708, 806, and/or 906 to the distal body end 710, 808, and/or 908. In some examples, the method further includes sliding the saddle 704 from the distal body end 710, 808, and/or 908 to the proximal body end 708, 806, and/or 906. According to some examples, retracting the sheath 40 about the wire 30 occurs in response to sliding the saddle 704 from the distal body end 710, 808, and/or 908 to the proximal body end 708, 806, and/or 906.

The saddle 704 may include a T-fitting 706, 804, and/or 904. In some examples, the method further includes sliding the T-fitting 706, 804, and/or 904 from the distal body end 710, 808, and/or 908 to the proximal body end 708, 806, and/or 906. According to some examples, the T-fitting 706, 804, and/or 904 includes a luer 3104. The method may further include inserting a syringe 60 into the luer 3104. In some examples, the method further includes sliding the syringe 60 from the distal body end 710, 808, and/or 908 to the proximal body end 708, 806, and/or 906.

According to some examples, the syringe 60 includes a syringe body and a plunger. The method may further include depressing the plunger of the syringe 60. In some examples, the method further includes releasing a fluid through the sheath 40 in response to depressing the plunger. According to some examples, the wire 30 includes a lumen. The method may further include releasing a fluid through the wire 30 in response to depressing the plunger.

In some examples, the saddle 704 includes a pull tab. According to some examples, the method further includes sliding the pull tab from the distal body end 710, 808, and/or 908 to the proximal body end 708, 806, and/or 906. The method may further include partially retracting the sheath 40 about the wire 30. In some examples, the method further includes partially exposing the distal wire end 1204 in response to partially retracting the sheath 40 about the wire 30.

According to some examples, the method further includes extending the sheath 40 about the wire 30. The method may further include at least partially enclosing the distal wire end 1204 in response to extending the sheath 40. In some examples, a limit switch 3306 is electronically coupled to the motor 610 and/or 3308. According to some examples, the method further includes preventing the motor 610 and/or 3308 from rotating in response to extending the sheath 40 about the wire 30.

The body 702, 802, and or 902 may include a proximal body end 708, 806, and/or 906 and a distal body end 710, 808, and/or 908. In some examples, a saddle 704 is slidably coupled to the body 702, 802, and or 902 whereby the saddle 704 moves along a first direction 712, 810, and or 916. According to some examples, the first direction 712, 810, and or 916 extends from the proximal body end 708, 806, and/or 906 to the distal body end 710, 808, and/or 908. The method may further include sliding the saddle 704 from the proximal body end 708, 806, and/or 906 to the distal body end 710, 808, and/or 908. In some examples, extending the sheath 40 about the wire 30 occurs in response to sliding the saddle 704 from the proximal body end 708, 806, and/or 906 to the distal body end 710, 808, and/or 908.

According to some examples, the saddle 704 includes a T-fitting 706, 804, and/or 904. The method further includes sliding the T-fitting 706, 804, and/or 904 from the proximal body end 708, 806, and/or 906 to the distal body end 710, 808, and/or 908. In some examples, the T-fitting 706, 804, and/or 904 includes a luer 3104. According to some examples, the method further includes inserting a syringe 60 into the luer 3104. The method may further include sliding the syringe 60 from the proximal body end 708, 806, and/or 906 to the distal body end 710, 808, and/or 908.

In some examples, the syringe 60 includes a syringe body and a plunger. According to some examples, the method further includes depressing the plunger of the syringe 60. The method may further include releasing a fluid through the sheath 40 in response to depressing the plunger. In some examples, the wire 30 includes a lumen. According to some examples, the method further includes releasing a fluid through the wire 30 in response to depressing the plunger.

The saddle 704 may include a pull tab. In some examples, the method further includes sliding the pull tab from the proximal body end 708, 806, and/or 906 to the distal body end 710, 808, and/or 908. According to some examples, the method further includes partially extending the sheath 40 about the wire 30. The method may further include at least partially enclosing the distal wire end 1204 in response to partially extending the sheath 40 about the wire 30.

In some examples, the body 702, 802, and or 902 includes a torque knob 1104. According to some examples, the method further includes providing torque to the wire 30. The method may further include controlling a direction of travel of the distal wire end 1204 in response to providing torque to the wire 30.

In some examples, the motor 610 and/or 3308 is located near a bottom of the body 702, 802, and or 902. According to some examples, the method further includes changing a ratio of rotation between the motor 610 and/or 3308 and the wire 30 via a gear.

The body 702, 802, and or 902 may include an expandable foot 1102 on a bottom of the body 702, 802, and or 902. In some examples, the method further includes expanding the expandable foot 1102. According to some examples, the method further includes stabilizing the body 702, 802, and or 902 in response to expanding the expandable foot 1102.

Also included in the present disclosure is a method, including directing a hypotube to a treatment site 50 of a patient, the hypotube including a proximal hypotube end and a distal hypotube end opposite the proximal hypotube end. In some examples, the hypotube is coupled to a motor 610 and/or 3308 that is at least partially enclosed by a body 702, 802, and or 902. According to some examples, the method includes powering the motor 610 and/or 3308. The method may include rotating the hypotube in response to powering the motor 610 and/or 3308.

In some examples, the method further includes extending the hypotube through a catheter 15 coupled to the body 702, 802, and or 902. According to some examples, the method further includes detachably coupling the catheter 15 to the body 702, 802, and or 902. The method may further include directing the catheter 15 to the treatment site 50 of the patient while the catheter 15 is detached from the body 702, 802, and or 902.

In some examples, the method further includes retracting the catheter 15 about the hypotube. According to some examples, the method further includes exposing the distal hypotube end in response to retracting the catheter 15. A limit switch 3306 may be electronically coupled to the motor 610 and/or 3308. In some examples, the method further includes allowing the motor 610 and/or 3308 to rotate in response to retracting the catheter 15 about the hypotube.

According to some examples, the body 702, 802, and or 902 includes a proximal body end 708, 806, and/or 906 and a distal body end 710, 808, and/or 908. A saddle 704 may be slidably coupled to the body 702, 802, and or 902 whereby the saddle 704 moves along a first direction 712, 810, and or 916. In some examples, the first direction 712, 810, and or 916 extends from the proximal body end 708, 806, and/or 906 to the distal body end 710, 808, and/or 908. According to some examples, the method further includes sliding the saddle 704 from the distal body end 710, 808, and/or 908 to the proximal body end 708, 806, and/or 906. Retracting the catheter 15 about the hypotube may occur in response to sliding the saddle 704 from the distal body end 710, 808, and/or 908 to the proximal body end 708, 806, and/or 906.

In some examples, the saddle 704 includes a T-fitting 706, 804, and/or 904. According to some examples, the method further includes sliding the T-fitting 706, 804, and/or 904 from the distal body end 710, 808, and/or 908 to the proximal body end 708, 806, and/or 906. The T-fitting 706, 804, and/or 904 may include a luer 3104. In some examples, the method further includes inserting a syringe 60 into the luer 3104. According to some examples, the method includes sliding the syringe 60 from the distal body end 710, 808, and/or 908 to the proximal body end 708, 806, and/or 906.

The syringe 60 may include a syringe body and a plunger. In some examples, the method further includes depressing the plunger of the syringe 60. According to some examples, the method further includes releasing a fluid through a lumen in the hypotube in response to depressing the plunger. The saddle 704 may include a pull tab. In some examples, the method further includes sliding the pull tab from the distal body end 710, 808, and/or 908 to the proximal body end 708, 806, and/or 906.

According to some examples, the method includes partially retracting the catheter 15 about the hypotube. The method may include partially exposing the distal hypotube end in response to partially retracting the catheter 15 about the hypotube.

In some examples, the method further includes extending the catheter 15 about the hypotube. According to some examples, the method further includes at least partially enclosing the distal hypotube end in response to extending the catheter 15. A limit switch 3306 may be electronically coupled to the motor 610 and/or 3308. In some examples, the method further includes preventing the motor 610 and/or 3308 from rotating in response to extending the catheter 15 about the hypotube.

According to some examples, the body 702, 802, and or 902 includes a proximal body end 708, 806, and/or 906 and a distal body end 710, 808, and/or 908. A saddle 704 may be slidably coupled to the body 702, 802, and or 902 whereby the saddle 704 moves along a first direction 712, 810, and or 916. In some examples, the first direction 712, 810, and or 916 extends from the proximal body end 708, 806, and/or 906 to the distal body end 710, 808, and/or 908. According to some examples, the method further includes sliding the saddle 704 from the proximal body end 708, 806, and/or 906 to the distal body end 710, 808, and/or 908. Extending the catheter 15 about the hypotube may occur in response to sliding the saddle 704 from the proximal body end 708, 806, and/or 906 to the distal body end 710, 808, and/or 908.

In some examples, the saddle 704 includes a T-fitting 706, 804, and/or 904. According to some examples, the method further includes sliding the T-fitting 706, 804, and/or 904 from the proximal body end 708, 806, and/or 906 to the distal body end 710, 808, and/or 908. The T-fitting 706, 804, and/or 904 may include a luer 3104. In some examples, the method further includes inserting a syringe 60 into the luer 3104. According to some examples, the method further includes sliding the syringe 60 from the proximal body end 708, 806, and/or 906 to the distal body end 710, 808, and/or 908.

The syringe 60 may include a syringe body and a plunger. In some examples, the method further includes depressing the plunger of the syringe 60. According to some examples, the method further includes releasing a fluid through a lumen in the hypotube in response to depressing the plunger.

The saddle 704 may include a pull tab. In some examples, the method further includes sliding the pull tab from the proximal body end 708, 806, and/or 906 to the distal body end 710, 808, and/or 908. According to some examples, the method further includes partially extending the catheter 15 about the hypotube. The method may further include at least partially enclosing the distal hypotube end in response to partially extending the catheter 15 about the hypotube.

In some examples, the body 702, 802, and or 902 includes a torque knob 1104. According to some examples, the method further includes providing torque to the hypotube. The method may further include controlling a direction of travel of the distal hypotube end in response to providing torque to the hypotube.

In some examples, the motor 610 and/or 3308 is located near a bottom of the body 702, 802, and or 902. According to some examples, the method further includes changing a ratio of rotation between the motor 610 and/or 3308 and the hypotube via a gear. The body 702, 802, and or 902 may include an expandable foot 1102 on a bottom of the body 702, 802, and or 902. In some examples, the method further includes expanding the expandable foot 1102. According to some examples, the method further includes stabilizing the body 702, 802, and or 902 in response to expanding the expandable foot 1102.

Also included in the present disclosure is a method, including removing a catheter 15 from a sterile pack 1002. In some examples, the method includes directing the catheter 15 to a treatment site 50 of a patient. According to some examples, the method includes operating a controller 20 from within the sterile pack 1002. The catheter 15 may be coupled to the controller 20.

In some examples, the method further includes detachably coupling the catheter 15 to the controller 20. According to some examples, the sterile pack 1002 includes a slit 1004. The method may further include placing the catheter 15 through the slit 1004 in the sterile pack 1002.

In some examples, the method further includes removing the catheter 15 from the treatment site 50 of the patient. According to some examples, the catheter 15 includes a sheath 40 and a wire 30. The method may further include disposing of the sheath 40. In some examples, the method further includes disposing of the wire 30.

According to some examples, the catheter 15 includes a sheath 40 and a wire 30. The method may further include detaching the sheath 40 from the controller 20. In some examples, the method further includes sterilizing the sheath 40 separately from the controller 20. According to some examples, the method further includes detaching the wire 30 from the controller 20. The method may further include sterilizing the wire 30 separately from the controller 20.

Also included in the present disclosure is an ablation system 10, including a controller 20. In some examples, the ablation system 10 includes a sheath 40 including an open proximal sheath end, an open distal sheath end, and a working lumen extending from the open proximal sheath end to the open distal sheath end. According to some examples, the open proximal sheath end is coupled to the controller 20 and the open distal sheath end is configured for insertion into a vascular system of a patient, the open distal sheath end located opposite the open proximal sheath end. The ablation system 10 may include a wire 30 extending from the controller 20 through the open proximal sheath end through the working lumen to the open distal sheath end. In some examples, the wire 30 has a proximal wire end 1202 and a distal wire end 1204 opposite the proximal wire end 1202, the distal wire end 1204 configured to mechanically treat a vessel wall of a treatment segment 55, whereby a length of the distal wire end 1204 defines a length of the treatment segment 55. Mechanically treating should be interpreted as equivalent to any term defining a type of disruption, including but not limited to abrading, ablating, disrupting, agitating, modifying, etc.

According to some examples, the working lumen is configured to slidably receive the wire 30 and allow for a passage of a fluid about the wire 30 therethrough to chemically treat the treatment segment 55. Chemically treating should be interpreted as equivalent to any term defining a treatment via chemicals, such as ablating, closing, denuding, etc. When the ablation system 10 receives a first input the distal wire end 1204 may mechanically treat the vessel wall. In some examples, when the ablation system 10 receives a second input, the ablation system 10 delivers the fluid into the treatment segment 55. According to some examples, when the ablation system 10 receives a third input, the ablation system 10 delivers the fluid into a subsequent treatment segment 55.

The sheath 40 may be retractable to expose the distal wire end 1204. In some examples, the controller 20 includes a motor 610 and/or 3308, a power supply 606 and/or 3302 configured to provide power to the motor 610 and/or 3308, and a limit switch 3306 electrically coupled to the motor 610 and/or 3308 and the power supply 606 and/or 3302. According to some examples, the limit switch 3306 allows electricity to flow from the power supply 606 and/or 3302 to the motor 610 and/or 3308 when the sheath 40 is fully retracted. The sheath 40 may be variably retractable to expose at least a portion of the length of the distal wire end 1204. In some examples, the portion of the length of the distal wire end 1204 is configured to form a variable treatment length.

According to some examples, the sheath 40 is extendable to enclose at least a portion of the distal wire end 1204. The controller 20 may include a motor 610 and/or 3308, a power supply 606 and/or 3302 configured to provide power to the motor 610 and/or 3308, and a limit switch 3306 electrically coupled to the motor 610 and/or 3308 and the power supply 606 and/or 3302. In some examples, the limit switch 3306 prevents electricity from flowing from the power supply 606 and/or 3302 to the motor 610 and/or 3308 when the sheath 40 is at least partially extended.

According to some examples, the ablation system 10 further includes at least one distance marking 3204 located on the sheath 40 between the open proximal sheath end and the open distal sheath end. The at least one distance marking 3204 may be arranged and configured according to the length of the treatment segment 55. In some examples, the ablation system 10 further includes a warning track 3206 located on the sheath 40 between the at least one distance marking 3204 and the open distal sheath end. According to some examples, the warning track 3206 is configured to indicate that an end of a workable treatment length has been reached.

The ablation system 10 may further include a slidable depth marker (i.e., the donut 3202) at least partially surrounding the sheath 40. In some examples, the slidable depth marker is slidably coupled to the sheath 40. According to some examples, the slidable depth marker is sized and configured such that it cannot enter an insertion point in the patient. The slidable depth marker may be positioned and configured to maintain a position of the sheath 40 and the wire 30 during a treatment. In some examples, the slidable depth marker is positioned and configured along the sheath 40 to indicate a distance to a deep venous system in the patient.

According to some examples, the controller 20 includes an actuator **506*a*, 506*b*, 608, 914, and/or 3304 configured to receive the first input. The controller 20 may include a motor 610 and/or 3308 and a power supply 606 and/or 3302 configured to provide power to the motor 610 and/or 3308. In some examples, the proximal wire end 1202 is operatively coupled to the motor 610 and/or 3308. According to some examples, the motor 610 and/or 3308 is configured to rotate the wire 30. The distal wire end 1204 may be configured to rotate in response to the motor 610 and/or 3308 rotating the wire 30. In some examples, the ablation system 10 includes a syringe 60 fluidly coupled to the working lumen. According to some examples, the syringe 60** is configured to receive the second input and the third input.

Also included in the present disclosure is a method, including inserting a catheter 15 into a vascular system of a patient. In some examples, the method includes moving the catheter 15 to a first treatment segment 55. According to some examples, the method includes treating, via the catheter 15, the first treatment segment 55. The method may include moving the catheter 15 to a second treatment segment 55. In some examples, the method includes treating, via the catheter 15, the second treatment segment 55.

According to some examples, the catheter 15 includes a sheath 40 having a working lumen and a wire 30 extending through the working lumen, the wire 30 including a proximal wire end 1202 and a distal wire end 1204 opposite the proximal wire end 1202. The method may further include abrading, via the distal wire end 1204, the first treatment segment 55. In some examples, the method further includes moving the wire 30 to the second treatment segment 55 in response to moving the catheter 15 to the second treatment segment 55. According to some examples, the method further includes abrading, via the distal wire end 1204, the second treatment segment 55.

The wire 30 may be electrically coupled to a motor 610 and/or 3308. In some examples, the method further includes rotating, via the motor 610 and/or 3308, the wire 30. According to some examples, the method further includes abrading, via rotating the wire 30, the first treatment segment 55. The method may further include abrading, via rotating the wire 30, the second treatment segment 55.

In some examples, the method further includes retracting the sheath 40 about the wire 30. According to some examples, the method further includes exposing the distal wire end 1204 in response to retracting the sheath 40 about the wire 30.

The wire 30 may be electrically coupled to a motor 610 and/or 3308. In some examples, a limit switch 3306 is electronically coupled to the motor 610 and/or 3308. According to some examples, the method further includes permitting, via the limit switch 3306, the motor 610 and/or 3308 to receive power in response to the sheath 40 being fully retracted. The method may further include providing, via the motor 610 and/or 3308, rotational output to the wire 30. In some examples, the method further includes rotating, via the rotational output, the wire 30. According to some examples, the method further includes abrading, via rotating the wire 30, the first treatment segment 55. The method may further include abrading, via rotating the wire 30, the second treatment segment 55.

In some examples, the wire 30 is electrically coupled to a motor 610 and/or 3308. According to some examples, an LED 912 and/or 3310 is electrically coupled to the motor 610 and/or 3308. The method may further include powering the LED. In some examples, the method further includes indicating, via powering the LED, that the motor 610 and/or 3308 is receiving power.

According to some examples, the method further includes extending the sheath 40 about the wire 30. The method may further include at least partially enclosing the distal wire end 1204 in response to retracting the sheath 40 about the wire 30.

In some examples, the wire 30 is electrically coupled to a motor 610 and/or 3308. According to some examples, a limit switch 3306 is electronically coupled to the motor 610 and/or 3308. The method may further include preventing, via the limit switch 3306, the motor 610 and/or 3308 from receiving power in response to the sheath 40 being at least partially extended. In some examples, the method further includes preventing the motor 610 and/or 3308 from providing rotational output. According to some examples, the method further includes preventing a rotation of the wire 30 in response to preventing the motor 610 and/or 3308 from providing rotational output.

An LED 912 and/or 3310 may be electrically coupled to the motor 610 and/or 3308. In some examples, the method further includes preventing the LED 912 and/or 3310 from receiving power. According to some examples, the method further includes indicating, via preventing the LED 912 and/or 3310 from receiving power, that the motor 610 and/or 3308 is not receiving power.

A syringe 60 may be fluidly coupled to the catheter 15. In some examples, the method further includes injecting a drug, via the syringe 60, at the first treatment segment 55. According to some examples, the method includes injecting a drug, via the syringe 60, at the second treatment segment 55. The method may further include preventing an injection of a drug while repositioning the catheter 15 to the second treatment segment 55.

In some examples, the sheath 40 includes a first distance marking 3204 and a second distance marking 3204. According to some examples, the method further includes pulling the catheter 15 out of the patient from the first distance marking 3204 to the second distance marking 3204. The method may further include repositioning, via pulling the catheter 15 out of the patient, the distal wire end 1204. In some examples, a distance from the first distance marking 3204 to the second distance marking 3204 is approximately equal to a treatment length of the distal wire end 1204. According to some examples, the method further includes repositioning the distal wire end 1204 by the treatment length.

The catheter 15 may include a warning track 3206. In some examples, the method further includes indicating, via the warning track 3206, that an end of a workable treatment length of the catheter 15 has been reached. According to some examples, the catheter 15 includes a donut 3202 at least partially surrounding the catheter 15. The method may further include indicating, via the donut 3202, a distance to a deep venous system in the patient.

Also included in the present disclosure is a method, including determining a first treatment segment 55 and a second treatment segment 55 in a vascular system of a patient. In some examples, the method includes inserting a catheter 15 into the vascular system of the patient. According to some examples, the method includes positioning the catheter 15 at the first treatment segment 55. The method may include injecting, via a syringe 60, a fluid (such as saline, or a drug such as sclerosant) at the first treatment segment 55. In some examples, the method includes repositioning the catheter 15 to the second treatment segment 55. According to some examples, the method includes injecting, via the syringe 60, the fluid at the second treatment segment 55.

The method may further include preventing an injection of a fluid while repositioning of the catheter 15 to the second treatment segment 55. In some examples, the catheter 15 includes a sheath 40 having a working lumen and a wire 30 extending through the working lumen, the wire 30 including a proximal wire end 1202 and a distal wire end 1204 opposite the proximal wire end 1202. According to some examples, the method further includes abrading, via the distal wire end 1204, the first treatment segment 55. The method may further include repositioning the wire 30 to the second treatment segment 55 in response to repositioning the catheter 15 to the second treatment segment 55. In some examples, the method further includes abrading, via the distal wire end 1204, the second treatment segment 55.

According to some examples, the wire 30 is electrically coupled to a motor 610 and/or 3308. The method may further include rotating, via the motor 610 and/or 3308, the wire 30. In some examples, the method further includes abrading, via rotating the wire 30, the first treatment segment 55. According to some examples, the method further includes abrading, via rotating the wire 30, the second treatment segment 55.

The method may further include retracting the sheath 40 about the wire 30. In some examples, the method further includes exposing the distal wire end 1204 in response to retracting the sheath 40 about the wire 30.

According to some examples, the wire 30 is electrically coupled to a motor 610 and/or 3308. A limit switch 3306 may be electronically coupled to the motor 610 and/or 3308. In some examples, the method further includes permitting, via the limit switch 3306, the motor 610 and/or 3308 to receive power in response to the sheath 40 being fully retracted. According to some examples, the method further includes providing, via the motor 610 and/or 3308, rotational output to the wire 30. The method may further include rotating, via the rotational output, the wire 30. In some examples, the method further includes abrading, via rotating the wire 30, the first treatment segment 55. According to some examples, the method further includes abrading, via rotating the wire 30, the second treatment segment 55.

The wire 30 may be electrically coupled to a motor 610 and/or 3308. In some examples, an LED 912 and/or 3310 is electrically coupled to the motor 610 and/or 3308. According to some examples, the method further includes powering the LED. The method may further include indicating, via powering the LED, that the motor 610 and/or 3308 is receiving power.

In some examples, the method further includes extending the sheath 40 about the wire 30. According to some examples, the method further includes at least partially enclosing the distal wire end 1204 in response to retracting the sheath 40 about the wire 30.

The wire 30 may be electrically coupled to a motor 610 and/or 3308. In some examples, a limit switch 3306 is electronically coupled to the motor 610 and/or 3308. According to some examples, the method further includes preventing, via the limit switch 3306, the motor 610 and/or 3308 from receiving power in response to the sheath 40 being at least partially extended. The method may further include preventing the motor 610 and/or 3308 from providing rotational output. In some examples, the method further includes preventing a rotation of the wire 30 in response to preventing the motor 610 and/or 3308 from providing rotational output.

According to some examples, an LED 912 and/or 3310 is electrically coupled to the motor 610 and/or 3308. The method may further include preventing the LED 912 and/or 3310 from receiving power. In some examples, the method further includes indicating, via preventing the LED 912 and/or 3310 from receiving power, that the motor 610 and/or 3308 is not receiving power.

According to some examples, the sheath 40 includes a first distance marking 3204 and a second distance marking 3204. The method may further include pulling the catheter 15 out of the patient from the first distance marking 3204 to the second distance marking 3204. In some examples, the method further includes repositioning, via pulling the catheter 15 out of the patient, the distal wire end 1204.

According to some examples, a distance from the first distance marking 3204 to the second distance marking 3204 is approximately equal to a treatment length of the distal wire end 1204. The method may further include repositioning the distal wire end 1204 by the treatment length.

In some examples, the catheter 15 includes a warning track 3206. According to some examples, the method further includes indicating, via the warning track 3206, that an end of a workable treatment length of the catheter 15 has been reached.

The catheter 15 may include a donut 3202 at least partially surrounding the catheter 15. In some examples, the method further includes indicating, via the donut 3202, a distance to a deep venous system in the patient.

Also included in the present disclosure is a method, including inserting a catheter 15 into a vascular system of a patient. In some examples, the method includes moving the catheter 15 to a first treatment segment 55. According to some examples, the method includes actuating a motor 610 and/or 3308 and rotating at least a portion of the catheter 15 in response to actuating the motor 610 and/or 3308. The method may include abrading the first treatment segment 55 for a predetermined amount of time in response to rotating at least the portion of the catheter 15. In some examples, the method includes moving the catheter 15 to a second treatment segment 55. According to some examples, the method includes abrading the second treatment segment 55 for the predetermined amount of time in response to rotating at least the portion of the catheter 15.

The method may further include indicating, via a component selected from the group consisting of an LED 912 and/or 3310, a speaker, a display 508, and combinations thereof, that the predetermined amount of time has elapsed. In some examples, the component is electrically coupled to a power supply 606 and/or 3302 that provides electricity to the motor 610 and/or 3308.

According to some examples, the catheter 15 includes a sheath 40 including a working lumen and a wire 30 including proximal wire end 1202 and a distal wire end 1204 opposite the proximal wire end 1202, the wire 30 extending through the working lumen. The method may further include retracting at least a portion of the sheath 40 from the wire 30. In some examples, the method further includes exposing the distal wire end 1204 in response to retracting the portion of the sheath 40 from the wire 30. According to some examples, the method further includes extending the sheath 40 about the wire 30. The method may further include at least partially enclosing the distal wire end 1204 in response to extending the sheath 40 about the wire 30.

In some examples, the wire 30 is operatively coupled to a motor 610 and/or 3308, and a limit switch 3306 is electronically coupled to the motor 610 and/or 3308. According to some examples, the method further includes allowing electricity to flow from a power supply 606 and/or 3302 to the motor 610 and/or 3308, via the limit switch 3306, in response to the sheath 40 being in a fully retracted state. The method may further include rotating the wire 30 in response to allowing electricity to flow from the power supply 606 and/or 3302 to the motor 610 and/or 3308. In some examples, the method further includes preventing electricity to flow from the power supply 606 and/or 3302 to the motor 610 and/or 3308, via the limit switch 3306, in response to the sheath 40 being in a non-fully retracted state. According to some examples, the method further includes terminating a rotation of the wire 30 in response to preventing electricity to flow from the power supply 606 and/or 3302 to the motor 610 and/or 3308.

The catheter 15 may include a sheath 40 having a working lumen, the sheath 40 including a first distance marking 3204 and a second distance marking 3204, and a wire 30 including proximal wire end 1202 and a distal wire end 1204 opposite the proximal wire end 1202, the wire 30 extending through the working lumen. In some examples, the catheter 15 includes a warning track 3206. According to some examples, the method further includes maintaining a longitudinal position of the catheter 15 with respect to the first treatment segment 55, wherein the longitudinal position is defined by a distal end of the catheter 15 with respect to the first treatment segment 55. The method may further include moving the catheter 15 out of the patient a distance approximately equal to a length from the first distance marking 3204 to the second distance marking 3204, wherein the length is approximately equal to a treatment length of the distal wire end 1204. In some examples, the method further includes indicating, via the warning track 3206, that an end of a workable treatment length of the catheter 15 has been reached.

According to some examples, the catheter 15 includes a sheath 40 including a working lumen, the sheath 40 including a first distance marking 3204 and a second distance marking 3204, and a wire 30 including proximal wire end 1202 and a distal wire end 1204 opposite the proximal wire end 1202, the wire 30 extending through the working lumen. The method may further include moving the catheter 15 out of the patient a distance approximately equal to a length from the first distance marking 3204 to the second distance marking 3204, wherein the length is approximately equal to a treatment length of the distal wire end 1204.

In some examples, the catheter 15 includes a warning track 3206. According to some examples, the method further includes indicating, via the warning track 3206, that an end of a workable treatment length of the catheter 15 has been reached.

A syringe 60 may be fluidly coupled to the catheter 15. In some examples, the method further includes injecting a fluid, via the syringe 60, at the first treatment segment 55.

According to some examples, the method further includes terminating an injection of the fluid prior to moving the catheter 15 to the second treatment segment 55. The method may further include injecting the fluid, via the syringe 60, at the second treatment segment 55. In some examples, the method further includes removing the catheter 15 from the vascular system of the patient. According to some examples, the method further includes terminating the injection of the fluid prior to removing the catheter 15 from the vascular system of the patient.

The catheter 15 may include a sheath 40 including a working lumen and a wire 30 including proximal wire end 1202 and a distal wire end 1204 opposite the proximal wire end 1202, the wire 30 extending through the working lumen. In some examples, the wire 30 is operatively coupled to a motor 610 and/or 3308, and a limit switch 3306 is electronically coupled to the motor 610 and/or 3308. According to some examples, the catheter 15 includes a sheath 40 including a working lumen, the sheath 40 including a first distance marking 3204 and a second distance marking 3204, and a wire 30 including proximal wire end 1202 and a distal wire end 1204 opposite the proximal wire end 1202, the wire 30 extending through the working lumen.

The catheter 15 may include a warning track 3206. In some examples, the method further includes maintaining a longitudinal position of the catheter 15 with respect to the first treatment segment 55, wherein the longitudinal position is defined by a distal end of the catheter 15 with respect to the first treatment segment 55. According to some examples, the method further includes retracting at least a portion of the sheath 40 from the wire 30. The method may further include exposing the distal wire end 1204 in response to retracting the portion of the sheath 40 from the wire 30. In some examples, the method further includes allowing electricity to flow from a power supply 606 and/or 3302 to the motor 610 and/or 3308, via the limit switch 3306, in response to the sheath 40 being in a fully retracted state.

According to some examples, the method further includes actuating a motor 610 and/or 3308 and rotating at least a portion of the catheter 15 in response to actuating the motor 610 and/or 3308. The method may further include rotating the wire 30 in response to allowing electricity to flow from the power supply 606 and/or 3302 to the motor 610 and/or 3308. In some examples, the method further includes moving the catheter 15 out of the patient a distance approximately equal to a length from the first distance marking 3204 to the second distance marking 3204, wherein the length is approximately equal to a treatment length of the distal wire end 1204.

In some examples, the method further includes extending the sheath 40 about the wire 30. According to some examples, the method further includes at least partially enclosing the distal wire end 1204 in response to extending the sheath 40 about the wire 30. The method may further include preventing electricity to flow from the power supply 606 and/or 3302 to the motor 610 and/or 3308, via the limit switch 3306, in response to the sheath 40 being in a non-fully retracted state. In some examples, the method further includes terminating a rotation of the wire 30 in response to preventing electricity to flow from the power supply 606 and/or 3302 to the motor 610 and/or 3308. According to some examples, the method further includes indicating, via the warning track 3206, that an end of a workable treatment length of the catheter 15 has been reached.

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1, and embodiments described in other sections may apply to and be combined with embodiments described within the "Topic 1" section.

To increase the clarity of various features, other features are not labeled in each figure.

The various features and processes described above may be used independently of one another or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, parallel, or some other manner Tasks or events may be added to or removed from the disclosed example embodiments. The example systems and components described herein may be configured differently than described. For example, elements may be added to, removed from, or rearranged compared to the disclosed example embodiments.

Specifically, any of the various catheter components and features included in the ablation system 10 described herein and illustrated in the figures may be used independently of one another or may be combined in various ways in any of the examples disclosed herein.

Furthermore, some of the components listed herein use the same number from figure to figure, including but not limited to catheter 15, controller 20, wire 30, sheath 40, syringe 60, proximal wire end 1202 distal wire end 1204, weighted tip 1210, proximal feature 2602, and distal feature 2702. It should be appreciated these components use the same numbers solely for ease of reference and to facilitate comprehension for the reader. While these components may use the same numbers, differences may be present in these components as illustrated in the various figures in which they appear and as described in the specification herein.

Conditional language used herein, such as, among others, "can," "could," "might," "may," "e.g.," and the like, unless expressly stated otherwise, or otherwise understood within the context as used, is generally intended to convey that certain embodiments include, while other embodiments do not include, certain features, elements and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms “comprising,” “including,” “having,” and the like are synonymous and are used inclusively, in an open-ended fashion, and do not exclude additional elements, features, acts, operations, and so forth. Also, the term “or” is used in its inclusive sense (and not in its exclusive sense) so that when used, for example, to connect a list of elements, the term “or” means one, some, or all of the elements in the list. Conjunctive language such as the phrase “at least one of X, Y, and Z,” unless expressly stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term “and/or” means that “and” applies to some embodiments and “or” applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term “and/or” is used to avoid unnecessary redundancy.

While certain example embodiments have been described, these embodiments have been presented by way of example only and are not intended to limit the scope of the inventions disclosed herein. Thus, nothing in the foregoing description implies that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

I claim:

1. A system, comprising:

a controller;

a sheath including an open proximal sheath end, an open distal sheath end, and a working lumen extending from the open proximal sheath end to the open distal sheath end, wherein the open proximal sheath end is coupled to the controller and the open distal sheath end is configured for insertion into a vascular system of a patient, the open distal sheath end located opposite the open proximal sheath end;

a wire extending from the controller through the open proximal sheath end through the working lumen to the open distal sheath end, the wire having a proximal wire end and a distal wire end opposite the proximal wire end, the distal wire end configured to mechanically treat a vessel wall of a treatment segment, whereby a length of the distal wire end defines a length of the treatment segment;

a first distance marking located on the sheath between the open proximal sheath end and the distal wire end;

a second distance marking located on the sheath between the first distance marking and the distal wire end, the first distance marking and the second distance marking separated by a distance approximately equal to the length of the distal wire end;

and a warning track located on the sheath between the second distance marking and the distal wire end, the warning track configured to indicate that an end of a workable treatment length has been reached, wherein the warning track comprises a series of markings, and wherein a distance between the markings is shorter in length than the distance between the first distance marking and the second distance marking, wherein the working lumen is configured to slidably receive the wire and allow for a passage of a fluid about the wire therethrough to chemically treat the treatment segment, and wherein when the system receives a first input the distal wire end mechanically treats the vessel wall, when the system receives a second input, the system delivers the fluid into the treatment segment, and when the system receives a third input, the system delivers the fluid into a subsequent treatment segment.

2. The system of claim 1, wherein the sheath is retractable to expose the distal wire end, and wherein the controller includes a motor, a power supply configured to provide power to the motor, and a limit switch electrically coupled to the motor and the power supply, whereby the limit switch allows electricity to flow from the power supply to the motor when the sheath is fully retracted.

3. The system of claim 1, wherein the sheath is variably retractable to expose at least a portion of the length of the distal wire end.

4. The system of claim 3, wherein the portion of the length of the distal wire end is configured to form a variable treatment length.

5. The system of claim 1, wherein the sheath is extendable to enclose at least a portion of the distal wire end, and wherein the controller includes a motor, a power supply configured to provide power to the motor, and a limit switch electrically coupled to the motor and the power supply, whereby the limit switch prevents electricity to flow from the power supply to the motor when the sheath is at least partially extended.

6. The system of claim 1, further comprising a slidable depth marker at least partially surrounding the sheath, the slidable depth marker slidably coupled to the sheath.

7. The system of claim 6, wherein the slidable depth marker is sized and configured such that it cannot enter an insertion point in the patient, and the slidable depth marker is positioned and configured to maintain a position of the sheath and the wire during a treatment.

8. The system of claim 6, the slidable depth marker is positioned and configured along the sheath to indicate a distance to a deep venous system in the patient.

9. The system of claim 1, wherein the controller includes an actuator configured to receive the first input, a motor, and a power supply configured to provide power to the motor, wherein the proximal wire end is operatively coupled to the motor, the motor configured to rotate the wire, and wherein the distal wire end is configured to rotate in response to the motor rotating the wire.

10. The system of claim 1, further comprising a syringe fluidly coupled to the working lumen, the syringe configured to receive the second input and the third input.

11. The system of claim 1, wherein the distal wire end includes a sinusoidal configuration.

12. The system of claim 11, wherein the distal wire end includes a weighted tip.

13. The system of claim 1, further comprising a T-fitting slidably coupled to the controller and detachably coupled to the sheath, the T-fitting configured to move in a first direction and a second direction opposite the first direction.

14. The system of claim 13, wherein the sheath is variably retractable to expose at least a portion of the length of the distal wire end in response to the T-fitting moving in the first direction.

15. The system of claim 13, wherein the sheath is extendable to enclose at least a portion of the distal wire end in response to the T-fitting moving in the second direction.

16. The system of claim 13, further comprising a tab configured to facilitate movement of the T-fitting.

17. The system of claim 13, further comprising a syringe fluidly coupled to the working lumen, the syringe configured to detachably couple to the T-fitting, wherein when the system receives a second input, the system delivers a fluid into the treatment segment.

18. The system of claim 17, wherein movement of the syringe facilitates movement of the T-fitting.

19. The system of claim 1, further comprising a third distance marking located on the sheath between the second distance marking and the distal wire end, the second distance marking and the third distance marking separated by a distance equal in length to the distance between the first distance marking and the second distance marking.

* * * * *